(12) United States Patent
Myers et al.

(10) Patent No.: US 12,281,976 B2
(45) Date of Patent: Apr. 22, 2025

(54) IN SITU FLUID SAMPLING DEVICE AND METHOD OF USING THE SAME

(71) Applicant: Honeywell International Inc., Charlotte, NC (US)

(72) Inventors: Ronald W. Myers, Dublin, OH (US); Andy Walker Brown, Richardson, TX (US); Stephan Michael Bork, Murphy, TX (US)

(73) Assignee: Honeywell International Inc., Charlotte, NC (US)

( * ) Notice: Subject to any disclaimer, the term of this patent is extended or adjusted under 35 U.S.C. 154(b) by 490 days.

(21) Appl. No.: 17/319,746

(22) Filed: May 13, 2021

(65) Prior Publication Data

US 2022/0364973 A1 Nov. 17, 2022

(51) Int. Cl.
*G01N 1/22* (2006.01)
*G01N 15/00* (2024.01)
(Continued)

(52) U.S. Cl.
CPC ....... *G01N 15/0612* (2013.01); *G01N 1/2208* (2013.01); *G01N 15/0227* (2013.01);
(Continued)

(58) Field of Classification Search
None
See application file for complete search history.

(56) References Cited

U.S. PATENT DOCUMENTS 4,021,117 A * 5/1977 Gohde ............... G01N 15/1456
377/50
4,232,967 A * 11/1980 Grachev ............ G01N 15/0205
356/336
(Continued)

FOREIGN PATENT DOCUMENTS

AU 2018101327 A4 10/2018
CA 2326811 A1 5/2002
(Continued)

OTHER PUBLICATIONS

Notice of Allowance and Fees Due (PTOL-85) Mailed on Jul. 28, 2023 for U.S. Appl. No. 17/805,072, 2 page(s).
(Continued)

*Primary Examiner* — David P Porta
*Assistant Examiner* — Djura Malevic
(74) *Attorney, Agent, or Firm* — Alston & Bird LLP

(57) ABSTRACT

Various embodiments are directed to a device for detecting fluid particle characteristics comprising: a collection fluid dispense assembly configured to selectively dispense a volume of collection fluid onto an absorbent media disposed within an internal sensor portion of a fluid composition sensor, producing a collection media based on interaction between the volume of collection fluid and the absorbent media; and a controller configured to determine, based on a particle image captured by an imaging device, a particle characteristic associated with a particle captured at the collection media. In various embodiments a device is configured to receive therein a collection media comprising a
(Continued)

biologically nutritive substance; and may comprise an imaging device and a controller configured to determine a biological particle characteristic based on a comparison of first particle data and second particle data generated by the imaging device, the second particle data being associated with an incubated particle configuration.

20 Claims, 16 Drawing Sheets

(51) Int. Cl.
    *G01N 15/02*         (2024.01)
    *G01N 15/0227*     (2024.01)
    *G01N 15/06*         (2006.01)
    *G01N 15/075*      (2024.01)
    *G01N 15/1434*     (2024.01)

(52) U.S. Cl.
    CPC ..... *G01N 15/0255* (2013.01); *G01N 15/1434* (2013.01); *G01N 2015/0053* (2013.01); *G01N 2015/0233* (2013.01); *G01N 2015/0261* (2013.01); *G01N 15/075* (2024.01); *G01N 2015/1454* (2013.01)

(56) References Cited

U.S. PATENT DOCUMENTS

| | | | | |
|---|---|---|---|---|
| 4,839,529 | A * | 6/1989 | Fruengel | G01N 15/06 356/339 |
| 5,001,463 | A * | 3/1991 | Hamburger | G01N 1/2205 356/438 |
| 5,040,424 | A | 8/1991 | Marple et al. | |
| 5,257,087 | A * | 10/1993 | Furuya | G01N 15/0205 356/336 |
| 5,404,217 | A | 4/1995 | Janik et al. | |
| 5,426,501 | A * | 6/1995 | Hokanson | G01N 15/1456 250/222.2 |
| 5,646,597 | A * | 7/1997 | Hamburger | G01N 15/0205 340/630 |
| 5,790,246 | A | 8/1998 | Kuhnell et al. | |
| 5,870,189 | A | 2/1999 | Uesugi et al. | |
| 5,870,190 | A * | 2/1999 | Unger | G01N 15/0205 356/336 |
| 5,932,795 | A * | 8/1999 | Koutrakis | G01N 15/0618 73/28.01 |
| 6,101,886 | A | 8/2000 | Brenizer et al. | |
| 6,115,119 | A * | 9/2000 | Sieracki | G01N 21/6458 356/337 |
| 6,435,043 | B1 | 8/2002 | Ferguson et al. | |
| 6,463,814 | B1 | 10/2002 | Letarte et al. | |
| 6,562,583 | B1 | 5/2003 | Herbig et al. | |
| 6,629,449 | B1 | 10/2003 | Kline-Schoder et al. | |
| 6,729,196 | B2 * | 5/2004 | Moler | B01D 45/08 73/863.22 |
| 6,887,710 | B2 * | 5/2005 | Call | B01D 21/2455 436/104 |
| 7,518,710 | B2 * | 4/2009 | Gao | G01N 15/1433 356/417 |
| 7,633,606 | B2 * | 12/2009 | Northrup | G01N 1/2273 356/73 |
| 7,762,677 | B2 | 7/2010 | Lundgren | |
| 7,799,567 | B1 * | 9/2010 | Call | G01N 1/2208 73/863.22 |
| 7,895,000 | B2 | 2/2011 | Chandler et al. | |
| 8,219,249 | B2 * | 7/2012 | Harrod | G06F 8/34 62/155 |
| 8,506,686 | B2 * | 8/2013 | Langle | B03C 3/47 493/194 |
| 8,866,063 | B2 | 10/2014 | Ozcan et al. | |
| 9,007,433 | B2 | 4/2015 | Ozcan et al. | |
| 9,057,702 | B2 | 6/2015 | Ozcan et al. | |
| 9,057,708 | B2 | 6/2015 | Kurosawa et al. | |
| 9,146,246 | B2 * | 9/2015 | Battrell | B01L 3/502776 |
| 9,170,599 | B2 | 10/2015 | Ozcan et al. | |
| 9,202,835 | B2 * | 12/2015 | Ozcan | H01L 27/14625 |
| 9,254,500 | B2 * | 2/2016 | Linnell | B05B 12/082 |
| 9,423,335 | B2 * | 8/2016 | Gabriel | G01N 21/6428 |
| 9,715,099 | B2 * | 7/2017 | Ozcan | G02B 21/365 |
| 9,743,909 | B1 | 8/2017 | Sapozhnikov et al. | |
| 9,772,281 | B2 * | 9/2017 | Bertaux | G01N 15/0612 |
| 9,933,351 | B2 * | 4/2018 | Kent | G01N 33/4925 |
| 9,952,191 | B2 * | 4/2018 | Crisp | G01N 33/18 |
| 10,066,985 | B2 * | 9/2018 | Stephen | B64G 1/10 |
| 10,281,371 | B2 * | 5/2019 | Hong | G01N 1/2205 |
| 10,317,320 | B2 * | 6/2019 | David | G01N 1/2205 |
| 10,684,209 | B1 * | 6/2020 | Manautou | G01N 15/1468 |
| 10,718,703 | B2 * | 7/2020 | Pariseau | G01N 15/1459 |
| 10,794,810 | B1 * | 10/2020 | Brown | G01N 15/0606 |
| 10,816,445 | B2 * | 10/2020 | Kelly | B01L 3/502715 |
| 10,876,949 | B2 * | 12/2020 | Brown | G01N 1/2273 |
| 11,333,593 | B2 * | 5/2022 | Myers | G01N 15/0255 |
| 11,345,723 | B2 * | 5/2022 | Criscione | B01D 71/68 |
| 11,662,542 | B2 * | 5/2023 | Misener | G01N 15/0205 356/335 |
| 2002/0124664 | A1 * | 9/2002 | Call | B01D 21/2455 73/863.22 |
| 2004/0011975 | A1 * | 1/2004 | Nicoli | G01N 15/0227 250/574 |
| 2004/0149634 | A1 * | 8/2004 | Hughes | B01J 20/103 210/500.1 |
| 2004/0237671 | A1 | 12/2004 | Ryan | |
| 2005/0106739 | A1 * | 5/2005 | Cabuz | A61B 5/157 436/63 |
| 2005/0214745 | A1 * | 9/2005 | Ryan | G01N 1/2208 435/5 |
| 2005/0255001 | A1 * | 11/2005 | Padmanabhan | G01N 15/1404 436/63 |
| 2006/0073585 | A1 * | 4/2006 | McDevitt | C12Q 1/24 435/297.2 |
| 2006/0234621 | A1 * | 10/2006 | Desrochers | F24F 3/044 702/50 |
| 2007/0035738 | A1 | 2/2007 | Bordelon | |
| 2007/0159627 | A1 | 7/2007 | Johnson | |
| 2007/0247718 | A1 | 10/2007 | Yoshikawa et al. | |
| 2008/0048874 | A1 | 2/2008 | Northrup et al. | |
| 2008/0221812 | A1 | 9/2008 | Pittaro et al. | |
| 2008/0233636 | A1 | 9/2008 | Ryan | |
| 2009/0027674 | A1 * | 1/2009 | Laudo | G01N 1/2208 356/417 |
| 2009/0063078 | A1 | 3/2009 | Chandler et al. | |
| 2009/0066934 | A1 * | 3/2009 | Gao | G01N 1/2273 356/417 |
| 2009/0128810 | A1 * | 5/2009 | Bates | G01N 15/1012 356/336 |
| 2009/0219530 | A1 * | 9/2009 | Mitchell | G01N 15/1433 356/336 |
| 2010/0101301 | A1 * | 4/2010 | McBrady | G01N 33/0011 73/23.21 |
| 2010/0129852 | A1 * | 5/2010 | Putnam | G01N 33/52 435/29 |
| 2010/0285606 | A1 * | 11/2010 | Phillips | G01N 33/54333 436/526 |
| 2011/0031394 | A1 | 2/2011 | Knowles et al. | |
| 2011/0136165 | A1 * | 6/2011 | Vojnovic | G03H 1/0443 435/39 |
| 2011/0195857 | A1 * | 8/2011 | Selinfreund | C12Q 1/40 506/9 |
| 2011/0286884 | A1 | 11/2011 | Eickhoff et al. | |
| 2012/0096925 | A1 * | 4/2012 | Hansen | G01N 1/2205 73/28.04 |
| 2012/0255375 | A1 * | 10/2012 | Kwok | G01N 1/40 73/863.22 |
| 2012/0312072 | A1 | 12/2012 | Stringham et al. | |
| 2012/0315666 | A1 * | 12/2012 | Fujioka | G01N 15/0612 435/39 |
| 2013/0142708 | A1 * | 6/2013 | Battrell | B01L 3/50273 422/430 |

(56) References Cited

U.S. PATENT DOCUMENTS

| | | | | |
|---|---|---|---|---|
| 2013/0220034 | A1* | 8/2013 | Peters | G01N 1/2273 |
| | | | | 73/863.22 |
| 2013/0244225 | A1* | 9/2013 | Kshirsagar | C12Q 1/06 |
| | | | | 435/5 |
| 2013/0260370 | A1* | 10/2013 | Kshirsagar | C12M 47/02 |
| | | | | 435/7.1 |
| 2013/0280752 | A1 | 10/2013 | Ozcan et al. | |
| 2013/0293873 | A1 | 11/2013 | Bentien | |
| 2014/0123730 | A1* | 5/2014 | Yamasaki | G01N 15/0618 |
| | | | | 96/400 |
| 2014/0227723 | A1* | 8/2014 | Ingber | A61P 31/04 |
| | | | | 530/387.3 |
| 2014/0234865 | A1* | 8/2014 | Gabriel | G01N 21/6428 |
| | | | | 356/338 |
| 2014/0268105 | A1* | 9/2014 | Bills | G02B 21/0052 |
| | | | | 356/450 |
| 2015/0099272 | A1* | 4/2015 | Hwang | C12Q 1/04 |
| | | | | 435/34 |
| 2015/0143929 | A1 | 5/2015 | Volckens et al. | |
| 2015/0177143 | A1* | 6/2015 | Fujita | G01N 15/0612 |
| | | | | 250/206 |
| 2015/0186842 | A1 | 7/2015 | Daniarov | |
| 2015/0260617 | A1* | 9/2015 | Ketcham | G01N 15/0255 |
| | | | | 73/863.22 |
| 2015/0323941 | A1* | 11/2015 | Pariseau | G05D 23/19 |
| | | | | 236/1 C |
| 2015/0330879 | A1* | 11/2015 | Mai | G01N 1/4077 |
| | | | | 422/69 |
| 2015/0355000 | A1* | 12/2015 | Bates | G01F 1/36 |
| | | | | 73/861.73 |
| 2015/0355084 | A1* | 12/2015 | White | G01N 15/1433 |
| | | | | 506/35 |
| 2016/0116404 | A1 | 4/2016 | Bertaux | |
| 2017/0016824 | A1 | 1/2017 | Tucker et al. | |
| 2017/0200197 | A1 | 7/2017 | Brubaker | |
| 2017/0219464 | A1* | 8/2017 | Houghton | G01N 1/2208 |
| 2017/0242234 | A1* | 8/2017 | Ashcroft | G01N 15/1463 |
| 2017/0370809 | A1* | 12/2017 | Miller-Lionberg | |
| | | | | G01N 1/2202 |
| 2018/0052425 | A1* | 2/2018 | Ozcan | G03H 1/0866 |
| 2018/0054425 | A1* | 2/2018 | Abbott | H04L 63/0428 |
| 2018/0088020 | A1 | 3/2018 | Couderc | |
| 2018/0168490 | A1 | 6/2018 | Jones et al. | |
| 2018/0258469 | A1* | 9/2018 | Johnson-Buck | C12Q 1/6876 |
| 2018/0259429 | A1* | 9/2018 | Adams | B64D 1/00 |
| 2018/0321126 | A1* | 11/2018 | Manautou | G01N 35/00871 |
| 2019/0011349 | A1 | 1/2019 | Bashir et al. | |
| 2019/0095586 | A1* | 3/2019 | McBrady | G16H 40/63 |
| 2019/0265153 | A1* | 8/2019 | Rottenberg | G01N 15/1468 |
| 2019/0293539 | A1* | 9/2019 | Manautou | G06V 20/693 |
| 2019/0294108 | A1* | 9/2019 | Ozcan | G06V 10/82 |
| 2019/0331581 | A1* | 10/2019 | Ikehata | C12M 41/48 |
| 2019/0336050 | A1* | 11/2019 | Deck | A61B 5/1459 |
| 2019/0346356 | A1* | 11/2019 | Karnik | G01N 15/1463 |
| 2020/0030795 | A1* | 1/2020 | Pais | B01L 7/5255 |
| 2020/0071647 | A1* | 3/2020 | Gilboa-Geffen | G01J 3/4406 |
| 2020/0088608 | A1* | 3/2020 | Murray | G01N 1/02 |
| 2020/0103328 | A1* | 4/2020 | Ozcan | G01N 15/0612 |
| 2020/0110018 | A1* | 4/2020 | Ryadinskiy | G01N 1/4077 |
| 2020/0240894 | A1* | 7/2020 | Isaacman-Vanwertz | |
| | | | | G01N 15/0606 |
| 2020/0340901 | A1* | 10/2020 | Ozcan | G06N 3/045 |
| 2020/0353166 | A1* | 11/2020 | Brown | G01N 29/222 |
| 2021/0016339 | A1 | 1/2021 | Takeda | |
| 2021/0090238 | A1* | 3/2021 | Gallagher-Gruber | |
| | | | | G06T 7/0002 |
| 2021/0115494 | A1* | 4/2021 | Reeslev | C12Q 1/04 |
| 2021/0116339 | A1* | 4/2021 | Nishikawa | G01N 1/30 |
| 2021/0164878 | A1* | 6/2021 | Brown | G06T 7/62 |
| 2021/0223155 | A1* | 7/2021 | Brown | G01N 15/0227 |
| 2021/0255014 | A1* | 8/2021 | Speldrich | G03H 1/0005 |
| 2021/0255068 | A1* | 8/2021 | Collins | G01N 1/2208 |
| 2021/0255080 | A1* | 8/2021 | Myers | G01N 15/0612 |
| 2021/0255081 | A1* | 8/2021 | Myers | G01N 15/1404 |
| 2021/0311032 | A1* | 10/2021 | Gilboa-Geffen | |
| | | | | G01N 33/54366 |
| 2021/0389245 | A1* | 12/2021 | Gilboa-Geffen | G01N 21/6456 |
| 2022/0033880 | A1* | 2/2022 | Sina | C12Q 1/6886 |
| 2022/0065780 | A1* | 3/2022 | Myers | G01N 15/0227 |
| 2022/0357261 | A1* | 11/2022 | Brown | G01N 15/14 |
| 2022/0364973 | A1* | 11/2022 | Myers | G01N 15/0643 |

FOREIGN PATENT DOCUMENTS

| | | |
|---|---|---|
| CN | 1695771 A | 11/2005 |
| CN | 103068456 A | 4/2013 |
| CN | 103270404 A | 8/2013 |
| CN | 105829860 A | 8/2016 |
| CN | 106323825 A | 1/2017 |
| CN | 107003246 A | 8/2017 |
| CN | 107208478 A | 9/2017 |
| CN | 107466364 A | 12/2017 |
| CN | 114127537 A | 3/2022 |
| EP | 2239557 A1 | 10/2010 |
| EP | 2413293 A1 | 2/2012 |
| EP | 1904826 B1 | 2/2019 |
| EP | 3444587 A1 | 2/2019 |
| EP | 3771898 A1 | 2/2021 |
| JP | 2003-075353 A | 3/2003 |
| JP | 2005-534946 A | 11/2005 |
| JP | 2007-101331 A | 4/2007 |
| JP | 2007-147437 A | 6/2007 |
| JP | 2009-025191 A | 2/2009 |
| JP | 2010-145310 A | 7/2010 |
| JP | 2011-502256 A | 1/2011 |
| JP | 2011-139656 A | 7/2011 |
| JP | 2012-037237 A | 2/2012 |
| JP | 2014-095571 A | 5/2014 |
| JP | 2019-511707 A | 4/2019 |
| WO | 2006/013573 A2 | 2/2006 |
| WO | 2012/081285 A1 | 6/2012 |
| WO | 2013/118259 A1 | 8/2013 |
| WO | 2014/156797 A1 | 10/2014 |
| WO | 2015/029673 A1 | 3/2015 |
| WO | 2015/049759 A1 | 4/2015 |
| WO | 2016/073745 A2 | 5/2016 |
| WO | 2016/147018 A1 | 9/2016 |
| WO | 2016/201113 A1 | 12/2016 |
| WO | 2017/051180 A1 | 3/2017 |
| WO | 2017/163650 A1 | 9/2017 |
| WO | 2017/196885 A1 | 11/2017 |
| WO | 2017/196995 A1 | 11/2017 |
| WO | 2018/117146 A1 | 6/2018 |
| WO | 2018/165590 A1 | 9/2018 |
| WO | 2018/176060 A1 | 9/2018 |
| WO | 2019/097523 A1 | 5/2019 |
| WO | 2019/165590 A1 | 9/2019 |
| WO | 2019/210375 A1 | 11/2019 |
| WO | 2020/072234 A1 | 4/2020 |
| WO | 2020/160158 A1 | 8/2020 |
| WO | 2021/034948 A1 | 2/2021 |

OTHER PUBLICATIONS

EP Office Action Mailed on Jul. 19, 2023 for EP Application No. 21151236, 8 page(s).

European search report and search opinion Mailed on Jan. 12, 2023 for EP Application No. 22169769.

JP Office Action w/English translation Mailed on May 18, 2023 for JP Application No. 2022117842, 5 page(s).

Communication Pursuant to Article 94(3) issued in European Application No. 20188262.8 on Oct. 7, 2021, 6 pages.

Corrected Notice of Allowability (PTOL-37) for U.S. Appl. No. 16/790,918, mailed on Oct. 18, 2021, 10 pages.

Corrected Notice of Allowability (PTOL-37) received for U.S. Appl. No. 16/748,543, mailed on Oct. 1, 2021, 2 pages.

Corrected Notice of Allowability (PTOL-37) received for U.S. Appl. No. 16/790,918, mailed on Sep. 22, 2021, 2 pages.

Decision to Grant issued in Japanese Application No. 2020-129927 on Sep. 10, 2021, 5 pages.

(56) References Cited

OTHER PUBLICATIONS

European Search Report and Search Opinion received for EP Application No. 21151236.3, mailed on Jul. 26, 2021, 14 pages.
European Search Report and Search Opinion Received for EP Application No. 21154848.2, mailed on Jul. 9, 2021, 14 pages.
European Search Report and Search Opinion Received for EP Application No. 21155330.0, mailed on Jul. 19, 2021, 11 pages.
Non-Final Office Action received for U.S. Appl. No. 16/790,924, mailed on Sep. 30, 2021, 18 pages.
Non-Final Office Action received for U.S. Appl. No. 17/028,635, mailed on Sep. 15, 2021, 13 pages.
Non-Final Office Action received for U.S. Appl. No. 17/247,096, mailed on Nov. 4, 2021, 13 pages.
Notice of Allowance received for U.S. Appl. No. 16/748,543, mailed on Dec. 3, 2021, 2 pages.
Notice of Allowance received for U.S. Appl. No. 16/748,543, mailed on Nov. 8, 2021, 2 pages.
Notice of Allowance received for U.S. Appl. No. 16/790,918, mailed on Aug. 18, 2021, 2 pages.
Office Action issued in Chinese Application No. 202010767051.2 on Jul. 27, 2021, 13 pages.
European search report Mailed on Oct. 10, 2022 for EP Application No. 22169769.
Examiner Interview Summary Record (PTOL-413) Mailed on Apr. 27, 2021 for U.S. Appl. No. 16/748,543.
List of references Mailed on Apr. 27, 2021 for U.S. Appl. No. 16/748,543.
List of references Mailed on Aug. 24, 2021 for U.S. Appl. No. 16/748,543.
Millipore: "Millipore Particle Monitoring Guide," 69 pgs., (1998). [Retrieved from the Internet: <URL: http://www.millipore.com/publications.nsf/dda0cb48c91c0fb685256743006365d6/b76a969e6d73cbd5852568c5006434c9/$FILE/ATTKZK5J/AD030.pdf [retrieved on Sep. 2, 2002]>]., Jan. 1, 1998.
Notice of Allowance and Fees Due (PTOL-85) Mailed on Aug. 24, 2021 for U.S. Appl. No. 16/748,543.
Advisory Action (PTOL-303) Mailed on Jul. 24, 2023 for U.S. Appl. No. 17/314,420, 3 page(s).
Examiner Interview Summary Record (PTOL-413) Mailed on Jul. 24, 2023 for U.S. Appl. No. 17/314,420, 1 page(s).
Air Sampling Filter Cassette Housings, [online], [retrieved Feb. 11, 2020_ <URL: https://www.zefon.com/cassette-housings> (10 pages).
Allergenco-D & Allergenco-D Posi-Track [online], [retrieved Feb. 11, 2020_ <URL: https://www.emssales.net/media/wysiwyg/uploads/ad_peer_reviewed_study.pdf> 9 pages.
Extended European Search Report for Patent Application No. 20170458.2 dated Sep. 10, 2020, 8 pages.
Extended European Search Report issued in European Application No. 20188262.8 on Dec. 8, 2020, 5 pages.
Extended European Search Report issued in European Application No. 21151236.3 on Jul. 26, 2021, 14 pages.
Extended European Search Report issued in European Application No. 21156433.1 on Jul. 14, 2021, 7 pages.
HPM Series Particulate Matter Sensors, [article, online], 2019, [retrieved Jul. 25, 2019] <URL: https://sensing.honeywell.com/sensors/particulate-sensors/hpm-series, 11 pages.
Non-Final Office Action issued in U.S. Appl. No. 16/790,918, filed Jan. 28, 2021.
Non-Final Office Action issued in U.S. Appl. No. 16/790,923, filed Feb. 2, 2021.
Non-Final Rejection Mailed on Apr. 27, 2021 for U.S. Appl. No. 16/748,543.
Notice of Allowance (PTOL-37) Mailed on Jun. 11, 2021 for U.S. Appl. No. 16/790,923.
Notice of Allowance and Fees Due (PTOL-85) Mailed on Sep. 8, 2020 for U.S. Appl. No. 16/396,524.
Notice of Allowance for U.S. Appl. No. 16/530,496 dated Jun. 2, 2020, 25 pages.
Notice of Allowance received for U.S. Appl. No. 16/748,543, mailed on Aug. 24, 2021, 10 pages.
Office Action for U.S. Appl. No. 16/396,524 dated Jun. 1, 2020, 13 pages.
Sampling Cassettes & Supplies, [online], [retrieved Nov. 3, 2020_ <URL:https://www.emssales.net/cassettes-supplies.html> (5 pages).
Schneider et al., Fast Particle Characterization Using Digital Holography and Neural Networks, 2016, [online article] [retrieved on Mar. 25, 2020] retrieved from the Internet URL: https://www.ncbi.nlm.nih.gov/pubmed/26835632, 7 pages.
Unpublished U.S. Appl. No. 62/837,066, filed Apr. 22, 2019, entitled "System and Method For Deep Learning-Based Color Holographic Microscopy".
Unpublished U.S. Appl. No. 62/838,149, filed Apr. 24, 2019, entitled "Label-Free Bio-Aerosol Sensing Using Mobile Microscopy and Deep Learning".
Wu et al., Label-Free Bioaerosol Sensing Using Mobile Microscopy and Deep Learning, [article, online], 2018, [retrieved Jul. 25, 2019], <URL: https://www.semanticscholar.org/paper/Label-Free-Bioaerosol-Sensing-Using-Mobile-and-Deep-Wu-Calis/fff5dc6d661ab985c3d14ec04fb84907d7750ab7>, 16 pages.
Annex to the communication Mailed on Oct. 6, 2021 for EP Application No. 20188262, 3 page(s).
CN Notice of Allowance Mailed on Mar. 17, 2022 for CN Application No. 202010767051, 4 page(s).
CN Office Action, including Search Report, Mailed on Jul. 27, 2021 for CN Application No. 202010767051.2, 13 page(s).
CN Search report Mailed on Aug. 3, 2020 for CN Application No. 202010767051, 2 page(s).
Communication about intention to grant a European patent Mailed on Oct. 12, 2022 for EP Application No. 20170458, 6 page(s).
Corrected Notice of Allowability (PTOL-37) Mailed on Aug. 27, 2021 for U.S. Appl. No. 16/790,923.
English Translation of CN Office Action Mailed on Jan. 6, 2022 for CN Application No. 202010767051.2, 5 page(s).
English translation of JP Decision to Grant dated Apr. 22, 2022 for JP Application No. 2021016701, 2 page(s).
English Translation of JP Office Action dated Dec. 21, 2021 for JP Application No. 2021017841, 2 page(s).
English translation of JP Office Action Mailed on Dec. 13, 2021for JP Application No. 2021017841.
EP Office Action Mailed on Oct. 7, 2021 for EP Application No. 20188262, 6 page(s).
European search report and search opinion Mailed on Jul. 9, 2021 for EP Application No. 21154848, 14 page(s).
European Search Report and Search Opinion Received for EP Application No. 20211654.7, mailed on May 3, 2021, 11 pages.
European Search Report Mailed on Dec 8, 2020for EP Application No. 20188262.8, 5 page(s).
European Search Report Mailed on Jan. 14, 2022for EP Application No. 21193185.2, 10 page(s).
Examiner Interview Summary Record (PTOL-413) Mailed on Oct. 24, 2022 for U.S. Appl. No. 17/805,072, 1 page(s).
Final Rejection Mailed on May 15, 2023 for U.S. Appl. No. 17/314,420, 11 page(s).
JP Decision to grant Mailed on Sep. 10, 2021 for JP Application No. 2020-129927, 5 page(s).
JP Office Action Mailed on Dec. 17, 2021 for JP Application No. 2021016701, 4 page(s).
JP Office Action Mailed on Sep. 30, 2022 for JP Application No. 2021171491, 3 page(s).
JP Search report Mailed on Dec. 13, 2021 for JP Application No. 2021017841, 9 page(s).
Non-Final Office Action Mailed on Apr. 27, 2021 for U.S. Appl. No. 16/748,543.
Non-Final Rejection Mailed on Jan. 23, 2023 for U.S. Appl. No. 17/314,420.
Non-Final Rejection Mailed on Jan. 28, 2021 for U.S. Appl. No. 16/790,918, 14 page(s).
Non-Final Rejection Mailed on Mar. 16, 2023 for U.S. Appl. No. 17/080,344, 11 page(s).
Non-Final Rejection Mailed on Oct. 26, 2022 for U.S. Appl. No. 17/410,682, 7 page(s).
Notice of Allowance and Fees Due (PTOL-85) Mailed on Jun. 11, 2021 for U.S. Appl. No. 16/790,923.

(56) References Cited

OTHER PUBLICATIONS

Notice of Allowance and Fees Due (PTOL-85) Mailed on May 9, 2023 for U.S. Appl. No. 17/805,072, 2 page(s).
Requirement for Restriction/Election Mailed on Apr. 7, 2023 for U.S. Appl. No. 17/247,096, 8 page(s).
Requirement for Restriction/Election Mailed on Sep. 30, 2022 for U.S. Appl. No. 17/314,420.
U.S. Patent Application filed on Apr. 22, 2019 for U.S. Appl. No. 62/837,066.
Wallace, J. Kent, et al., "Robust, compact implementation of an off-axis digital holographic microscope", Optics Express, Jun. 29, 2015, pp. 17367-17378. vol. 23, No. 13.
CN Office Action, including Search Report Mailed on Nov. 20, 2023 for CN Application No. 202110080239, 5 page(s).
English Translation of CN Office Action, including Search Report dated Nov. 20, 2023 for CN Application No. 202110080239, 5 page(s).
English translation of JP Decision to Grant dated Oct. 17, 2023 for JP Application No. 2022117842, 3 page(s).
English Translation of JP Office Action dated Sep. 20, 2023 for JP Application No. 2022180787, 3 page(s).
JP Decision to Grant Mailed on Oct. 17, 2023 for JP Application No. 2022117842, 3 page(s).
JP Office Action Mailed on Sep. 20, 2023 for JP Application No. 2022180787, 3 page(s).
Non-Final Rejection Mailed on Nov. 27, 2023 for U.S. Appl. No. 17/314,420, 9 page(s).
Non-Final Rejection Mailed on Sep. 6, 2023 for U.S. Appl. No. 17/314,420, 10 page(s).
EP Office Action Mailed on Jan. 31, 2024 for EP Application No. 22169769, 7 page(s).
CN Office Action, including Search Report Mailed on Jul 20, 2024 for CN Application No. 202110080239, 6 page(s).
English Translation of CN Office Action, including Search Report dated Jul. 20, 2024 for CN Application No. 202110080239, 6 page(s).
English Translation of JP Office Action dated Jul 11, 2024 for JP Application No. 2023130726, 2 page(s).
JP Office Action Mailed on Jul. 11, 2024 for JP Application No. 2023130726, 2 page(s).
JP Decision to Grant Mailed on Mar. 1, 2024 for JP Application No. 2022180787, 5 page(s).
Intention to grant Mailed on Oct. 17, 2024 for EP Application No. 22182866, 8 page(s).
CN Notice of Allowance Mailed on Nov. 29, 2024 for CN Application No. 202110080239, 2 page(s).
English translation of CN Notice of Allowance dated Nov. 29, 2024 for CN Application No. 202110080239, 2 page(s).
JP Office Action dated Nov. 8, 2024 for JP Application No. 2023195065, w/English translation, 8 page(s).
CN Office Action Mailed on Jan. 19, 2025 for CN Application No, 202210453976, 8 page(s).
Communication about intention to grant a European patent Mailed on Feb. 17, 2025 for EP Application No. 22169769, 6 page(s).
Decision to grant a European patent Mailed on Feb. 20, 2025 for EP Application No. 22182866, 2 page(s).
English Translation of CN Office Action dated Jan. 19, 2025 for CN Application No. 202210453976, 13 page(s).

\* cited by examiner

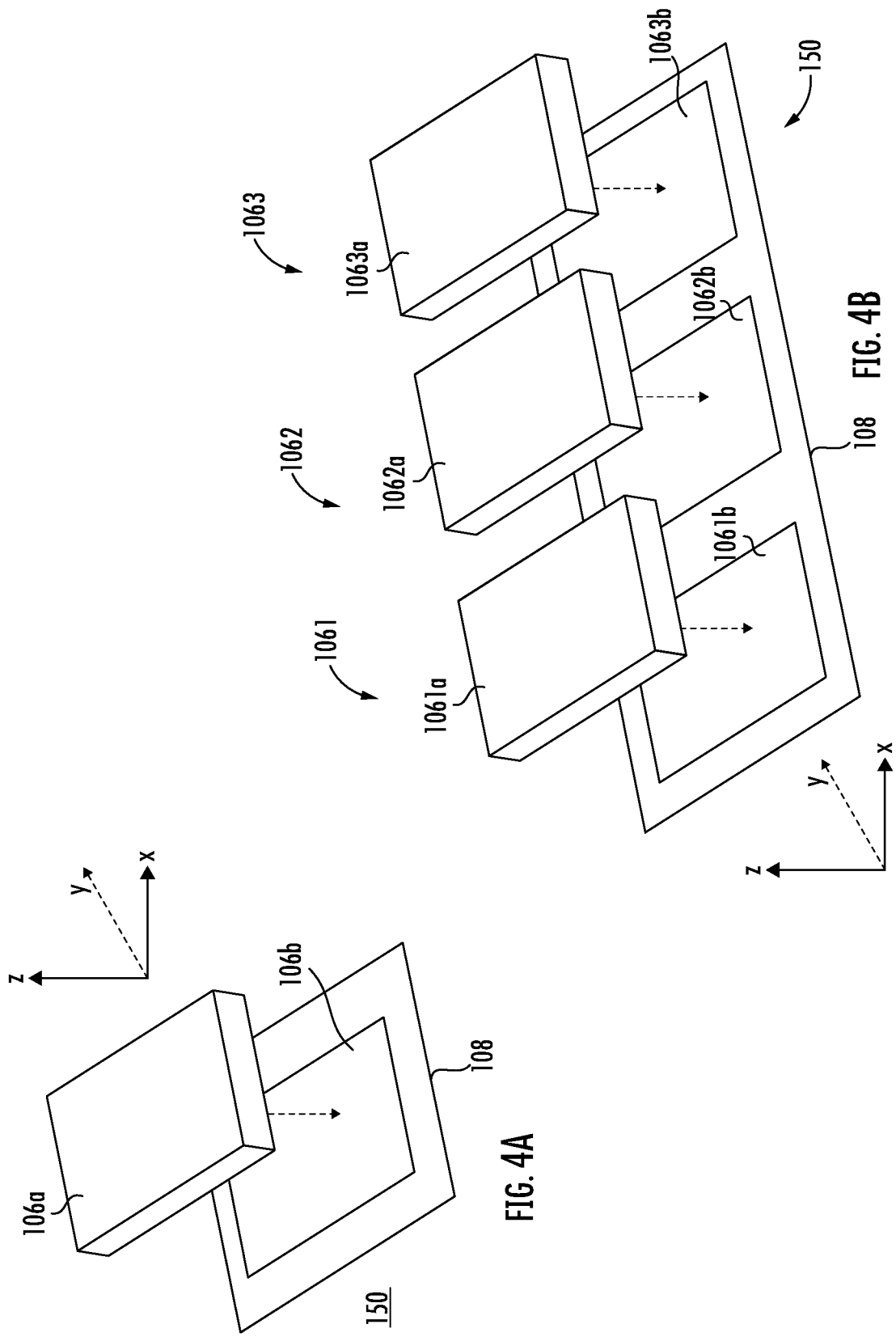

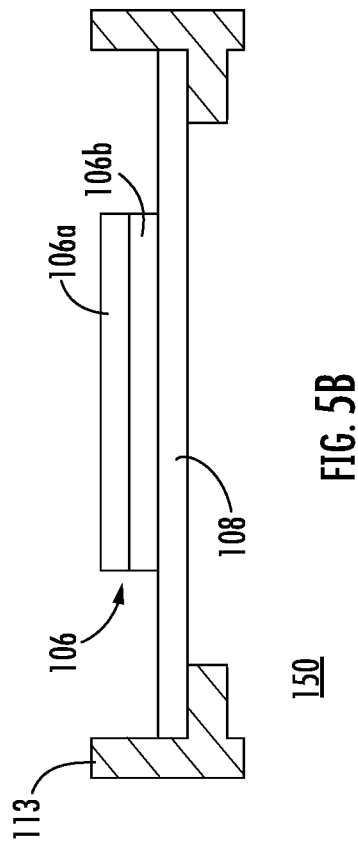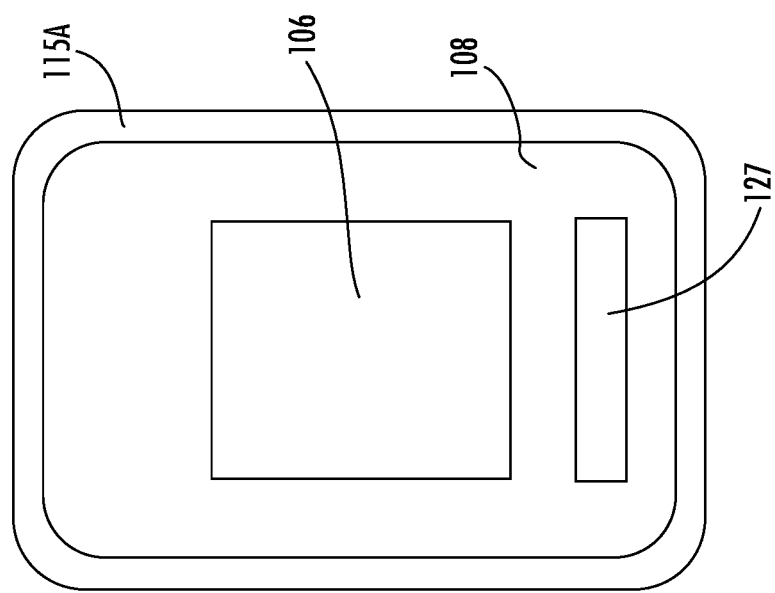

IN SITU FLUID SAMPLING DEVICE AND METHOD OF USING THE SAME

TECHNOLOGICAL FIELD

An example embodiment relates generally to devices for generating a collection media on-demand at a fluid sensor in an in situ configuration, and devices used to detect one or more colony-forming units (CFUs) within the air of an ambient environment.

BACKGROUND

Sensors and devices may be utilized to characterize various aspects of fluids in a wide variety of applications. As just one example, sensor devices may be utilized for monitoring air conditions, such as monitoring and characterizing the particulate content of a flow of air. However, existing fluid sensor devices provide limited functionality in generating data indicative of certain characteristics of fluids, such as the unique identity and concentration of individual particles contained within a fluid flow. Fluid sensor devices can use holographic imaging methods to characterize particle identity and/or distribution throughout a fluid sample. It is desirable to improve various aspects of particle sampling and analysis. In general, it can be advantageous for a fluid sampling device to utilize a sampling media that enables rapid, automated, and/or simplified sequential sampling of particles. For devices utilizing a particle imaging operation (such as lensless holography) to generate particle data associated with particles captured within a collection media, it is desirable to avoid device inefficiencies and/or failures caused by the use of a collection media that is contaminated and/or materially compromised in order to achieve optimal image quality. Further, for it can be advantageous for a such fluid sampling devices to identify and characterize colony-forming units (CFUs) present within the air in an environment to facilitate the avoidance of exposure to dangerous pathogens and other harmful materials.

Accordingly, a need exists for an improved fluid sensor device capable of providing an uncompromised collection media for particle collection in a consistent and easily repeatable manner. Further, a need exists for an improved fluid flow device capable of accurately collecting and analyzing the particle content of a sample volume of fluid from an ambient environment in order to detect the presence of CFUs within the air.

BRIEF SUMMARY

Various embodiments described herein relate to apparatuses and methods for collecting and characterizing particles suspended within a fluid. Various embodiments are directed to a device for detecting fluid particle characteristics comprising: a fluid composition sensor configured to receive a volume of fluid, the fluid composition sensor comprising: a collection fluid dispense assembly configured to selectively dispense a volume of collection fluid onto an absorbent media disposed at least partially within an internal sensor portion of the fluid composition sensor so as to cause a collection media to be produced based at least in part on an interaction between the volume of collection fluid and the absorbent media; wherein the collection media is configured to receive one or more particles of a plurality of particles within the volume of fluid; and an imaging device configured to capture a particle image of at least a portion of the one or more particles received by the collection media; and a controller configured to determine, based at least in part on the image, at least one particle characteristic of the plurality of particles of the volume of fluid.

In various embodiments, the collection fluid dispense assembly may be configured to selectively dispense a plurality of volumes of collection fluid respectively onto a plurality of absorbent media, each of the plurality of absorbent media defining at least a portion of a respective collection media assembly; wherein the fluid composition sensor is configured to sequentially receive the plurality of collection media assemblies within the internal sensor portion at least substantially in series. In various embodiments, wherein the imaging device may be configured to capture the particle image using lensless holography. In various embodiments, the collection fluid dispense assembly may be configured to selectively dispense the volume of collection fluid onto the absorbent media disposed at a first position within the internal sensor portion; and wherein the wherein the collection media may be configured to receive the one or more particles from within the volume of fluid at a second position within the internal sensor portion. In certain embodiments, the fluid composition sensor may further comprise a housing that defines the internal sensor portion and is selectively configurable between a first housing configuration and a second housing configuration; wherein the first housing configuration may enable a reconfiguration of the collection media between the first position and the second position; and wherein the second housing configuration may provide a secured seal so as to isolate the at least a portion of the collection media disposed within the internal sensor portion from a volume of ambient fluid. In certain embodiments, the absorbent media may be attached to a substrate tape defined at least in part by a substrate tape length extending in a first direction, wherein the collection media produced based at least in part on the interaction between the dispensed volume of collection fluid and the absorbent media may be disposed upon the substrate tape; and wherein the substrate tape may be configured such that a reconfiguration of the collection media from the first position to the second position within the internal sensor portion is defined by a shift of the substrate tape along a linear travel path extending in the first direction so as to cause the collection media to move relative to the internal sensor portion.

In various embodiments, the volume of collection fluid may comprise Triacetin. In various embodiments, the collection media may dispense assembly comprises a collection fluid cartridge configured to store one or more volumes of collection fluid therein, the collection fluid cartridge being fluidly connected to a dispense header configured to direct a flow of the volume of collection fluid dispensed from the collection fluid cartridge in a dispense direction. In various embodiments, the controller may be configured to generate one or more control signals configured to cause the device to reposition the collection media from the first position to the second position upon determining that the volume of collection fluid has been dispensed from the collection fluid dispense assembly.

Various embodiments are directed to a device for detecting fluid particle characteristics comprising: a fluid composition sensor configured to receive a fluid sample comprising a plurality of particles, the fluid composition sensor comprising: an internal sensor portion configured to receive a collection media assembly comprising a collection media, the collection media comprising a biologically nutritive substance and being configured to receive at least a portion of the plurality of particles from within the fluid sample; and an imaging device configured to generate first particle data using a particle imaging operation, the first particle data being associated with an initial particle configuration defined by the plurality of particles at a first instance; a controller configured to determine a biological particle characteristic associated with the fluid sample based at least in part on a comparison of the first particle data and second particle data, the second particle data being associated with an incubated particle configuration defined by the plurality of particles at a second instance, wherein the second instance is subsequent an incubation operation wherein at least a portion of the plurality of particles are exposed to an incubation environment.

In various embodiments, the biological particle characteristic may be defined at least in part by a detected particle type characteristic associated with one or more particles of the plurality of particles received by the fluid composition sensor, wherein the detected particle type characteristic corresponds to a determination that one or more of the plurality of particles comprises a colony-forming unit (CFU). In various embodiments, the particle imaging operation may comprise lensless holography. In various embodiments, the biologically nutritive substance may comprise one or more of an agar substance and a gelatin-based gel substance, the biologically nutritive substance being defined at least in part by one or more nutritional characteristics configured to facilitate biological development of one or more particles engaged therewith. In various embodiments, the collection media may comprise a non-nutritive substance layer disposed on top of a receiving face of the collection media.

In various embodiments, the fluid composition sensor may be configured to receive a second fluid sample, and wherein the fluid composition sensor is further configured to at determine a second biological particle characteristic associated with the second fluid sample via one or more sequential operations executed at least substantially in series in an at least substantially automated configuration. In various embodiments, the device may further comprise an incubation chamber comprises an internal chamber portion configured to define the incubation environment; wherein the incubation chamber is configured to receive the collection media assembly comprising the collection media within the internal chamber portion; and wherein the device is configured to execute the incubation operation by exposing the plurality of particles disposed within the collection media to the incubation environment within the incubation chamber such that one or more of the plurality of particles disposed within the collection media comprises one or more incubated particles defining the incubated particle configuration. In various embodiments, the incubation chamber may be in electronic communication with the controller, and wherein the controller is further configured to selectively control one or more incubation environment conditions defining the incubation environment such that the incubation operation may define an at least partially automated operation.

In various embodiments, the imaging device may be further configured to generate the second particle data associated with the incubated particle configuration at the second instance. In various embodiments, the fluid composition sensor may comprise a second imaging device configured to generate the second particle data associated with the incubated particle configuration at the second instance. In various embodiments, one or both of the controller and the imaging device may be configured to read one or more identification elements disposed on the collection media assembly so as to identify the collection media assembly, wherein the one or more identification elements are configured to uniquely identify the collection media assembly.

BRIEF DESCRIPTION OF THE DRAWINGS

Reference will now be made to the accompanying drawings, which are not necessarily drawn to scale, and wherein:

FIGS. 4A and 4B illustrate various exploded views of collection media assemblies in accordance with exemplary embodiments described herein.

FIGS. 5A-5B illustrate various views of a collection media assembly in accordance with various embodiments described herein.

DETAILED DESCRIPTION

Figure 1:
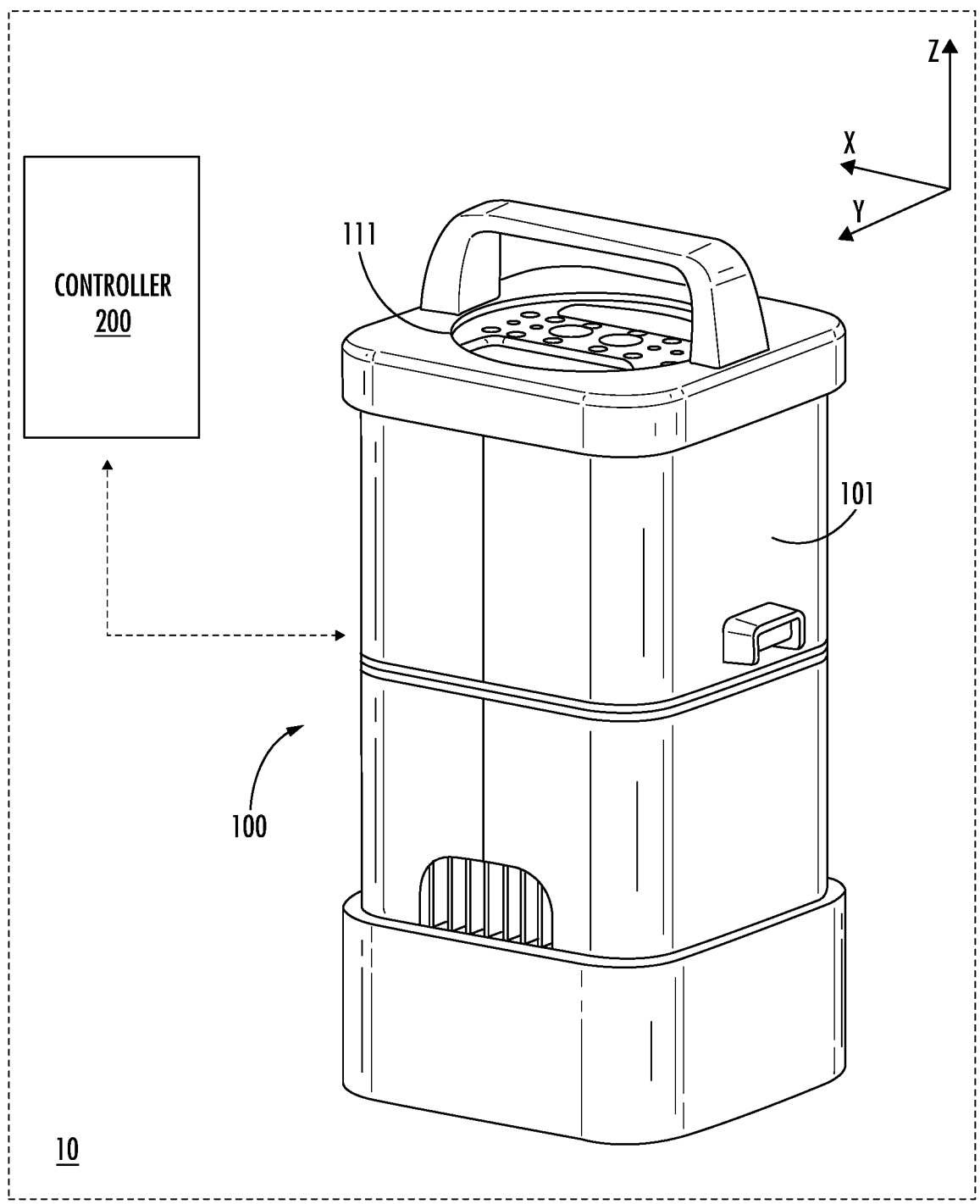
FIG. 1 illustrates a perspective view of an exemplary fluid composition sensor in accordance with various embodiments.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

While values for dimensions of various elements are disclosed, the drawings may not be to scale.

The words "example," or "exemplary," when used herein, are intended to mean "serving as an example, instance, or illustration." Any implementation described herein as an "example" or "exemplary embodiment" is not necessarily preferred or advantageous over other implementations. As used herein, a "fluid" may be embodied as a gas, a liquid, or a combination of a gas and a liquid in a single flow. Thus, the term "fluid" encompasses various materials subject to flow, such as, but not limited to, liquids and/or gases (e.g., air, oil, or the like). Thus, various embodiments are directed to fluid sensing systems, such as gas sensing systems (e.g., certain embodiments being specifically configured for operation with air; other embodiments being configured for operation with other gases, such as inert gases, volatile gases, and/or the like), liquid sensing systems, and/or the like.

Described herein is a device (which may be referred to as a fluid composition sensor, a fluid particulate sensor, a gas particulate sensor, or an air particulate senor as discussed herein) configured to characterize and/or monitor particulate matter within a volume of fluid. The device discussed herein may be configured to quantify and classify the particles within a volume of fluid based at least in part on the imaging of particles received by a collection media of a fluid composition sensor. Further, the device discussed herein may be configured to characterize the particle composition within the volume of fluid by directly identifying the particle size and particle type of each of the particles received by the collection media of the fluid composition sensor. By directly determining the particle size and particle type, the device as described herein may be configured to detect a change in particle composition within a volume of fluid over time and/or location. Further, the device as described herein may be configured to detect, identify, and/or characterize various biological matter present within a fluid sample received by the device by detecting one or more changes in particle composition (e.g., particle characteristics) between a first instance and a second instance.

Further, in addition to executing both a particle collection function and a particle analysis function in one or more at least substantially automated operations, the device described herein may be configured to execute a collection media generation function on-demand through an at least substantially in situ process within an internal sensor portion. In various embodiments, the present device may facilitate an on-demand application of a volume of collection fluid (e.g., Triacetin) onto an absorbent media disposed about a substrate element. As described herein, the device may be configured such that the dispensed collection fluid engaging the absorbent media may initiate a reaction therebetween that may produce a resultant collection media disposed upon the substrate element. The resultant collection media generated by the on-demand collection media generation function may be configured to receive a one or more particles from within a fluid sample, so as to facilitate execution a particle collection function of the device. In certain embodiments, such a resultant collection media may be produced within an interior sensor portion of a fluid composition sensor of the present invention in real-time. Such a collection media generation function may thereby minimize the various inefficiencies associated with the leadup time required by remotely manufactured collection media, such as, for example, device measurement inaccuracies caused by collection media contamination, collection media aging (e.g., hardening), collection media repositioning (e.g., transportation), and/or collection media variability. As described herein, the present invention is configured to enable a substantially automated and/or serial in situ production of a plurality of collection media on-demand.

In various embodiments, detect and characterize one or more CFUs present within a volume of fluid (e.g., air) in an environment. In various embodiments, the present invention utilizes one or more sensors configured to receive a fluid sample and generate particle data associated with the particles present within the fluid sample as captured at a first instance and a second instance. As described herein, in various embodiments, the present invention may facilitate execution of an incubation operation at a time in between the first instance and the second instance, such that the particle data captured at the second instance may be associated with an incubated particle configuration defined by the plurality of particles received by the device after the particles were subjected to an incubation environment. As described herein, the present invention may be configured to compare the first particle data captured at the first instance (pre-incubation) and associated with an initial particle configuration with the second particle data captured at the second instance (post-incubation) and associated with the incubated particle configuration in order to identify one or more differences caused by a biological growth of one or more of the incubated particles disposed within the collection media. The present invention is configured to detect, identify, and/or characterize a one or more CFUs present within the fluid sample based at least in part on the comparison between the initial particle data generated prior to the particles being subjected to an incubation environment and the incubated particle data associated with the incubated particles, and detection of one or more differences therebetween. The present invention exploits a robust design to provide a fluid flow device, fluid flow monitoring system, and various related methods of using the same configured to measure the presence of CFUs within an environment.

In various embodiments, an exemplary fluid flow device 10 may comprise a fluid composition sensor 100 configured to receive a volume of fluid flowing therethrough. Specifically, the fluid flow device 10 may be configured to receive a volume of a gas, such as air, flowing therethrough. In various embodiments, the fluid composition sensor 100 may be further configured to capture an image of one or more particles of a plurality of particles present within the received volume of fluid. In various embodiments, as described herein, an exemplary fluid composition sensor 100 may comprise a housing, an impactor nozzle, a collection media, an at least partially transparent substrate, and an imaging device. As illustrated in FIG. 1, the fluid composition sensor 100 may comprise a housing 101 defining an internal sensor portion in which one or more components of an exemplary fluid composition sensor 100 described herein may be at least partially disposed. In various embodiments, the housing may comprise rigid materials (e.g., rigid plastic materials) and/or resilient materials (e.g., resilient polymeric materials forming protective sleeves on an upper and lower end of the housing). In various embodiments, the housing 101 may comprise an upper surface and bottom surface, with one or more sidewalls extending therebetween in a substantially vertical direction. As described herein, the one or more sidewalls of the fluid composition sensor housing 101 may define at least a portion of the height of the fluid composition sensor 100, wherein the height of the sensor 100 extending in the z-direction. Similarly, the bottom surface of the fluid composition sensor housing 101 may extend along an at least substantially horizontal plane defining at least a portion of both the length and the width of the fluid composition sensor 100, wherein the length and the width of the sensor 100 extending in the x-direction and the y-direction, respectively.

In various embodiments, the housing 101 of the fluid composition sensor 100 may comprise a sensor fluid inlet 111 comprising an opening through which the fluid composition sensor 100 may receive a volume of fluid from an ambient environment. For example, in various embodiments, the sensor fluid inlet 111 through which the fluid composition sensor 100 may receive a volume of fluid may embody a device fluid inlet through which the fluid flow device 10 may receive one or more volumes of air from the ambient environment. As described herein, the fluid flow device 10 may comprise a controller 200. In various embodiments, as described in further detail herein, an exemplary fluid composition sensor 100 may comprise and/or be electronically and communicatively connected to the controller 200, such that the fluid composition sensor 100 is configured to transmit one or more signals (e.g., data signals, control signals) to a controller 200. It should be understood that the exemplary configuration of the fluid flow device 10 illustrated in FIG. 1 and/or various exemplary fluid composition sensors 100 described are merely examples, and in various embodiments, a fluid flow device, as described herein, may incorporate fluid composition sensors having other configurations for detection of one or more particle characteristics.

Figure 2:
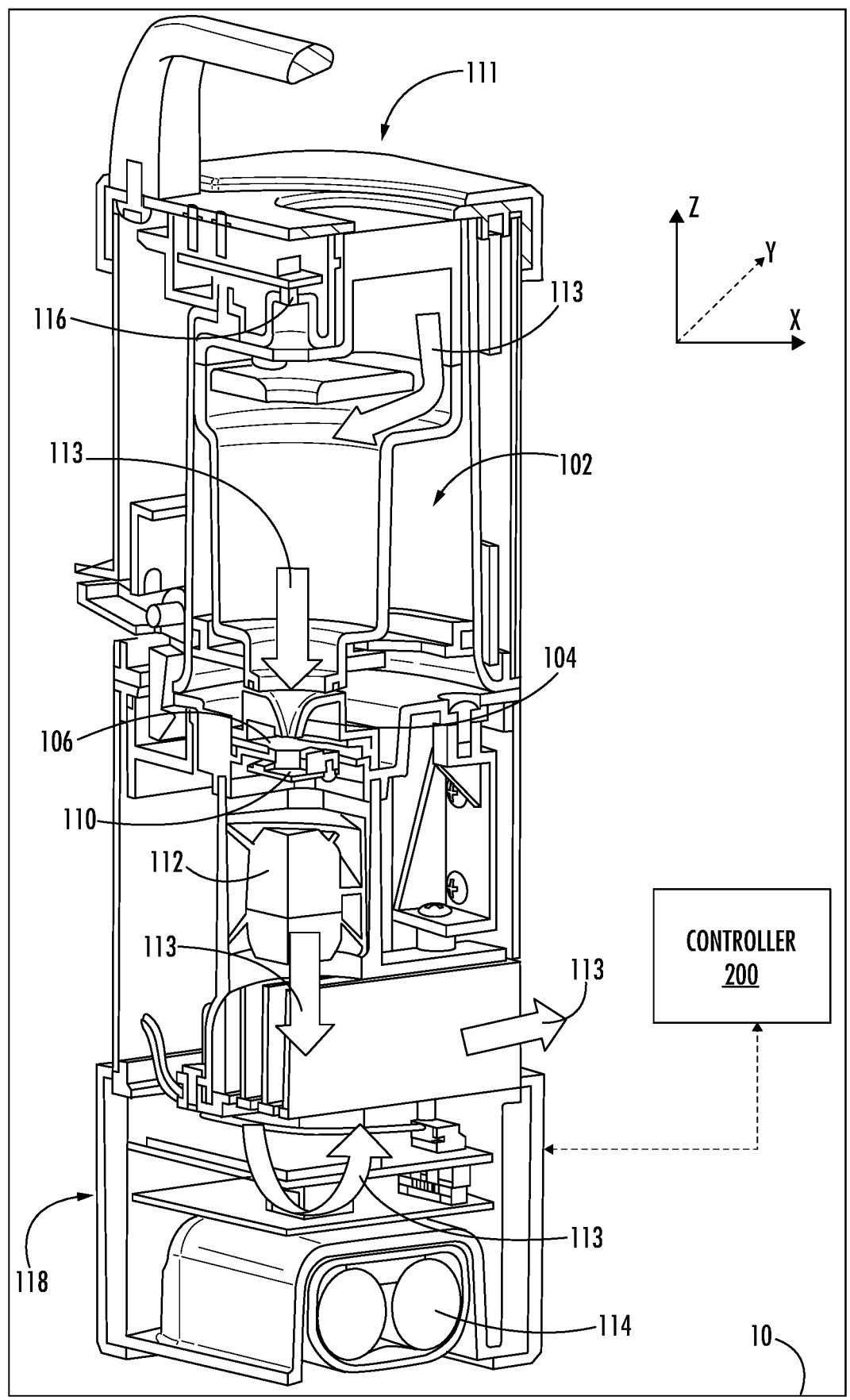
FIG. 2 illustrates a cross-sectional view of an exemplary apparatus in accordance with one embodiment described herein.
Figure 3:
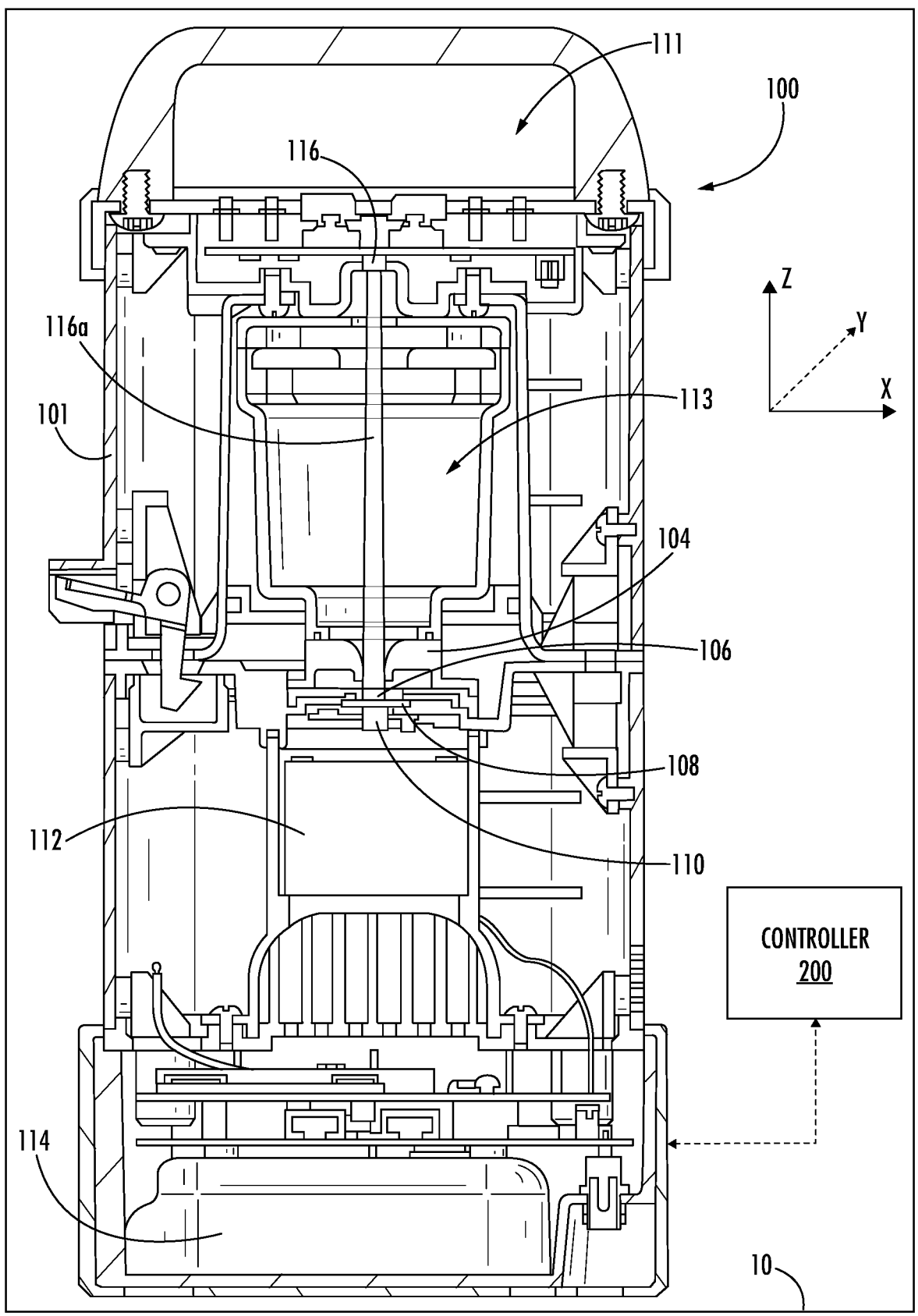
FIG. 3 illustrates a cross-sectional view of an exemplary apparatus in accordance with one embodiment described herein

In various embodiments, as illustrated in FIGS. 2 and 3, an exemplary fluid composition sensor 100 of a fluid flow device 10 may comprise a housing 101, an imaging device 110, and an illumination source 116. Further, in various embodiments, an exemplary fluid composition sensor 100 may further comprise an impactor nozzle 104, a collection media 106, an at least partially transparent substrate 108. For example, in various embodiments, one or more components described herein may be embodied as a replaceable collection media assembly. As a non-limiting example, in various embodiments, a replaceable collection media assembly may embody a replaceable cartridge comprising one or more of an impactor nozzle 104, a collection media 106, an at least partially transparent substrate 108. In such an exemplary circumstance, an exemplary fluid composition sensor 100 may be configured to receive at least a portion of the replaceable collection media assembly in order to facilitate the execution of one or more of the particle collection and particle imaging operations of the sensor, as described in further detail herein. Further, in various embodiments, the fluid composition sensor 100 may further comprise a power supply 114 configured to power the fluid composition sensor 100 and a fan or pump 112 configured to pull the volume of fluid into and through the fluid composition sensor 100. In various embodiments, the fan or pump 112 may be calibrated, such that the flow rate of fluid moving through the device is known/determined based at least in part on the operating characteristics (e.g., operating power) of the fan or pump 112.

In various embodiments, a fluid composition sensor 100 comprising a collection media 106 may be configured so as to direct at least a portion of a fluid sample received through by the fluid composition sensor 100 via a housing fluid inlet 111 along a fluid flow path 113 within an internal sensor portion 102 of the sensor housing 101 in a direction perpendicular to a receiving surface of the collection media 106, such that the fluid sample (e.g., one or more of a plurality of particles therein) may interact with the collection media 106. As illustrated, at least a portion of the fluid flow path 113 may be defined by a fluid flow conduit within the sensor housing 101 that is positioned downstream from the housing fluid inlet 111 and/or upstream from a collection media 106. As described in further detail herein, the collection media 106 may be configured to receive one or more the plurality of particles within a fluid sample via the interaction with the first fluid sample as the sample flows along the fluid flow path 113. In various embodiments, an exemplary collection media may comprise a biologically nutritive substance, such as, for example, agar, gelatin-based gels, and/or the like, that includes a nutritional component and/or a collection media moisture characteristic that is sufficient to facilitate biological growth of one or more particles disposed therein, such as, for example, during an incubation operation, as described herein. In various embodiments, for example, an exemplary fluid composition sensor 100 may be configured to utilize a collection media 106 comprising a biologically nutritive substance in order to facilitate the detection, identification, and/or characterization of one or more CFUs present within a fluid sample received by the sensor 100. For example, a collection media 106 comprising a biologically nutritive substance may facilitate the culturing of the plurality of particles disposed therein over a period of time (e.g., between a first instance and a second instance). In such an exemplary circumstance, one or more CFUs within the plurality of particles received by the sensor 100 that may be below an optical resolution of the sensor 100 at a first instance, and therefore, may be at least substantially undetectable by the sensor 100. Further, for example such an exemplary circumstance, one or more particles within the plurality of particles received by the sensor 100 may be resolved (e.g., imaged) by the sensor 100 at a first instance, but may be unidentifiable as a CFU based solely on an analysis of the particle data captured at the first instance, In various embodiments, based at least in part on a culturing facilitated by a biologically nutritive substance present within the collection media 106, the one or more previously undetectable CFUs may undergo a biological growth such that the particle size, particle shape, particle volume, particle mass matter concentration, and/or the like, may evolve (e.g., grow) over the period of time such that they may be detected and/or identified as a CFU by the fluid composition sensor 100 at the second instance. In various embodiments, as described herein, such a biological growth may be further facilitated by one or more incubation operations executed between the first instance and the second instance.

In various embodiments, a collection media 106 comprising a biologically nutritive substance may further comprise a non-nutritive substance layer disposed on top of a receiving face of the collection media. In such an exemplary circumstance, the non-nutritive substance layer may be configured to cover a receiving face of the biologically nutritive substance so as to receive the plurality of particles from a fluid sample prior to the particles interacting with the biologically nutritive substance. In various embodiments, a non-nutritive substance layer, as described herein, may be configured to enhance the particle capturing efficiency. Further, in various embodiments, the non-nutritive substance layer may be configured to enhance one or more optical characteristics, such as, for example, a transparency characteristic, an index of refraction, and/or the like, related to the collection media 106. Further still, in various embodiments, the non-nutritive substance layer may be configured to prevent dehydration of the biologically nutritive substance.

In various embodiments, as described herein, the fluid composition sensor 100 may be configured to execute at least both of a particle collection function and a particle analysis function. FIG. 2 illustrates a perspective sectional view of an exemplary fluid composition sensor 100 according to various embodiments described herein. In particular, the exemplary fluid composition sensor 100 illustrated in FIG. 2 is shown as executing at least a portion of the particle collection function of the sensor 100. As described herein, the particle collection function of the fluid composition sensor 100 may correspond to the fluid composition sensor 100 receiving from an ambient environment a volume of fluid (e.g., a fluid sample) comprising a plurality of particles and directing the volume of fluid along a fluid flow path 113 to an impactor nozzle 104 disposed within the internal sensor portion 102. As described herein, in various embodiments, an impactor nozzle 104 may be arranged relative to a collection media 106 such that the impactor nozzle 104 may direct the volume of fluid traveling along the fluid flow path 113 toward a collection media 106 disposed within sensor 100. The impactor nozzle 104 may comprise a nozzle inlet configured to receive the volume of fluid traveling along an upstream portion of the fluid flow path 113, and a nozzle outlet defined at least in part by a cross-sectional area that is smaller than that of the nozzle inlet. The impactor nozzle 104 may be configured such that the fluid sample containing the plurality of particles passes therethrough in a fluid flow direction at least substantially perpendicular to the collection media 106. As described, the cross-sectional areas of the impactor nozzle 104 may be configured to increase the velocity of the volume of fluid flowing through the nozzle 104 (e.g., the plurality of particles therein) and induce laminar flow such that at least a portion of the particles of the plurality of particles within the volume of fluid comprise a momentum sufficient to impact the collection media 106 and become disposed therein. For example, the volume of fluid may travel from the outlet of the impactor nozzle 104 and pass across at least a portion of a surface of the collection media 106 such that at least a portion of the plurality of particles within the volume of fluid become disposed within the collection media 106.

In various embodiments, the collection media 106 may be embodied as a portion of a collection media assembly. For example, the collection media assembly may be embodied as a replaceable slide (as illustrated in FIGS. 5A-8B), within which a replaceable collection media 106 may be disposed. In other embodiments, the entirety of the replaceable slide may be disposable, and the collection media 106 may be permanently secured therein. However, in other embodiments, the collection media assembly may comprise a collection media tape 106 (e.g., the collection media tape may be embodied as an elongated collection media 106 that may be moved through the fluid composition sensor 100 such that a fresh (e.g., unused) portion of the collection media tape may be exposed to the fluid flowing through the impactor nozzle 104). As yet another example, the collection media 106 may be disposed on and/or as a portion of a rotatable disc, such that the collection media 106 may be rotated relative to the fluid composition sensor 100 such that a fresh (e.g., unused) portion of the collection media disc may be exposed to the fluid flowing through the impactor nozzle 104. It should be understood that the collection media 106 may be embodied in any of a variety of forms. In yet other embodiments, the collection media 106 may be permanently affixed within the composition sensor 100, such that the entire composition sensor 100 may be disposable once the collection media 106 is sufficiently filled with particles from a fluid flowing through the composition sensor 100.

In various embodiments, upon passing across the surface of the collection media 106, the fluid sample may continue to travel within an internal sensor portion 102 along a fluid flow path 113. At least a portion of the fluid sample may be directed (e.g., by the fan and/or pump 112) to an outlet of the fluid composition sensor 100 (e.g., one or more exhaust slots) whereby the fluid sample may be dispensed back into the ambient environment. In various embodiments, the fluid composition sensor 100 may be configured such that prior to being dispensed from the sensor 100, at least a portion of the volume of fluid may be directed toward various internal circuitry 118 within the internal sensor portion 102 and circulated so as to facilitate the cooling of the internal circuitry 118 by passing the volume of fluid over at least a portion thereof. In such a circumstance, the fluid composition sensor 100 may be configured such that the portion of the volume of fluid used to cool the internal circuitry 118 may be subsequently dispensed from the outlet of the sensor 100. In various embodiments, the internal circuitry 118 of an exemplary fluid composition sensor 100 may comprise, define, and/or be electronically and communicatively connected to at least part of a controller 200, such that the fluid composition sensor 100 is configured to transmit one or more signals (e.g., data signals, control signals) to the controller 200.

FIG. 3 illustrates a cross-sectional view of an exemplary fluid composition sensor 100 according to various embodiments described herein. In particular, the exemplary fluid composition sensor 100 illustrated in FIG. 3 is shown as executing at least a portion of the particle analysis function of the sensor 100. As described herein, the particle analysis function of the fluid composition sensor 100 may correspond to the fluid composition sensor 10 capturing an image of the one or more particles received by—and disposed within—the collection media 106 and determining, based at least in part on the captured image, at least one particle characteristic of the volume of fluid received by the fluid composition sensor 100. For example, in various embodiments, the fluid composition sensor 100 may comprise a lens-free microscope. In various embodiments, a lens-free microscope may utilize one or more techniques, such as, for example, lensless holography, to capture a particle image, as described herein, of the one or more particles of a plurality of particles received by a collection media 106. Alternatively, the fluid composition sensor 100 may comprise a lens-based imaging device or any other apparatus configured to capture an image which may be analyzed by an apparatus as described herein so as to determine a particle size or other particle characteristics of one or more particles captured by the collection media 106. In various embodiments, a lens-based imaging device may utilize one or more imaging techniques, such as, for example, optical microscopy, to capture a particle image, as described herein, of the one or more particles of a plurality of particles received by a collection media 106. In various embodiments, optical microscopy may comprise light transmitted through or reflected from a collection media 106 and/or a plurality of particles disposed therein through one or more lenses to magnify and capture an image of one or more of the particles of the plurality of particles 120 within the collection media 106. As described herein, the fluid composition sensor 100 may be electronically and communicatively connected to a controller 200.

In various embodiments, as illustrated, a fluid composition sensor 100 may comprise an illumination source 116 configured to emit one or more light beams. In various embodiments, the illumination source 116 may be a laser, lamp, light-emitting diode (LED), and/or the like, which may be collectively configured to generate a light beam 116a (e.g., ultraviolet, visible, infrared, white, a single visible color, or multiple color light) that may be emitted toward the collection media 106, as described herein in further detail. For example, an illumination source 116 of the fluid composition sensor 100 may be configured to emit one or more light beams 116a so as to engage the collection media 106 and illuminate the one or more particles disposed therein, as described herein. In various embodiments, as illustrated in FIG. 3, the fluid composition sensor 10 may be configured such that the illumination source 116 is at least substantially aligned with the imaging device 110. Further, for example, the illumination source 116 may be at least substantially aligned with the central axis of the impactor nozzle 112. In such a configuration, the illumination source 116 may be arranged such that the light beam 116a emitted therefrom extends through the internal sensor portion 102 in a direction that is at least substantially aligned with the central nozzle axis, such that at least a portion of the one or more light beams 116a extend through both the nozzle inlet and the nozzle outlet of the impactor nozzle 104 to illuminate the one or more particles disposed in the collection media 106. As described herein, an imaging device 110 disposed within the internal sensor portion 102 may be configured to utilize the light beam 116a emitted from the illumination source 116 in order to capture an image of the one or more particles of the plurality of particles received by the collection media 106 using one or more imaging techniques such as, for example holographic microscopy (e.g., lensless holography) and/or the like.

The fluid composition sensor 100 (e.g., controller 200) may be configured to analyze the captured image, as described herein, so as to determine a particle size and/or other particle characteristics of one or more of the particles captured within the collection media 106. For example, wherein the imaging device 110 is configured to utilize lensless holography analyze one or more particles embedded within the collection media 106, the imaging device 110 may computationally produce an image of the one or more particles received by the collection media 106 by digitally reconstructing one or more microscopic images of one or more particles without using a lens. In executing the particle analysis function as described herein, the fluid composition sensor 100 may detect at least a portion of a plurality of particles within a fluid sample and/or may characterize the particle composition within the fluid sample by directly identifying the particle count, particle size and/or particle type for one or more of the particles (e.g., each of the particles) received by the collection media 106. For example, in various embodiments, the fluid composition sensor 100 may detect a change in particle composition within a volume of fluid over time and/or location. Further, in various embodiments, the fluid composition sensor 100 may detect a change in one or more particle characteristics within one or more particles captured at a collection media 106 upon execution of an incubation operation, as described herein, wherein the collection media 106 is exposed to a controlled environment for a period of time in order to initiate and/or culture a biological development (e.g., growth) of one or more of the captured particles therein.

As described herein, in various embodiments, the particle collection function and the particle analysis function of the fluid composition sensor 10 may be executed in sequence, such that upon determining that an entirety of a sample volume of fluid has passed across a surface of a collection media 106 and/or that a predetermined particle collection time has passed, and thus, that the need for the particle collection functionality of the fluid composition sensor has been at least temporarily exhausted, the fluid composition sensor may be configured to initiate the particle analysis functionality.

In various embodiments, the fluid composition sensor 100 may be connected to a power supply 114 configured to receive power and power the fluid composition sensor 100. As non-limiting examples, the power supply 114 may comprise one or more batteries, one or more capacitors, one or more constant power supplies (e.g., a wall-outlet), and/or the like. In some embodiments the power supply 114 may comprise an external power supply positioned outside of the fluid composition sensor 100 and configured to deliver alternating or direct current power to the fluid composition sensor 100. Further, in some embodiments, as illustrated in FIGS. 2 and 3, the power supply 114 may comprise an internal power supply, for example, one or more batteries, positioned within the housing 101 of the fluid composition sensor 100. In various embodiments, a power supply 114 may be connected to the controller 200 to enable distribution of power through the controller to one or more components of the fluid composition sensor 100, such as, for example, an imaging device, an illumination device, a collection fluid dispense assembly, and/or a collection media motor, as described herein.

As described, the imaging device 110 of the fluid composition sensor 100 may be positioned at least substantially adjacent (e.g., in contact with or spaced a distance away from) the collection media 106 such that the imaging device 110 may effectively capture one or more images of the one or particles embedded within the collection media 106. As discussed herein, the collection media 106 may be replaceable (e.g., as a part of a cassette that may be inserted into and/or removed from the fluid composition sensor 100), and accordingly the fluid composition sensor 100 may define one or more alignment features, support features, and/or the like for maintaining a desired positioning of the collection media 106 relative to the imaging device 110 (e.g., such that a bottom surface of the collection media 106 is in contact with or proximate (e.g., within 5 mm, within 3 mm, within 1 mm and/or the like) an imaging surface of the imaging device 110. Such alignment features and/or support features may comprise one or more grooves, slots, ridges, and/or the like configured to position the collection media 106 in a desired position relative to the imaging device 110. In various embodiments, the fluid composition sensor 100 (e.g., the imaging device 110) may have a designated field of view for capturing, permanently and/or temporarily, an image of multiple particles of the plurality of particles simultaneously. The collection media 106 may be positioned within the fluid composition sensor 100 relative to the imaging device 110 such that at least a portion of the collection media 106 is within the field of view of the imaging device 110.

Further, the collection media 106 may be positioned relative to the imaging device 110 such that the portion (e.g., at least a portion) of the collection media 106 within which the particles from the volume of fluid flowing through the sensor 100 are disposed is visible by the imaging device 110 (i.e. within the field of view). In various embodiments, the field of view of the imaging device 110 may be rectangular and may be configured to comprise an aspect ratio of up to 1:20. The aspect ratio may be selectively configured to optimize the field of view of the imaging device 110 based at least in part on a fluid flow velocity, pressure drop, and/or Reynolds number associated with a volume of fluid traveling along at least a portion of the fluid flow path (e.g., through an impactor nozzle 104), each of which may be optimized in order to maximize flow performance and particle collection.

For example, in various embodiments, the field of view of the imaging device 110 may have an aspect ratio of 3:4. However, it should be understood that other shapes, sizes, and proportions of a field of view may be provided in other embodiments (e.g., round, ovular, rectangular with a different aspect ratio, and/or the like).

As described herein, the field of view of the imaging device 110 on the collection media 106 may correspond to the configuration of the imaging device 110 relative to the collection media 106. In particular, the field of view of the imaging device 110 may be defined at least in part by the distance between the imaging device 110 and the collection media 106 disposed within the sensor 10. Further, as described herein, the area of the collection media 106 that receives particles from an exemplary volume of fluid as the exemplary fluid flows through the sensor 100 may correspond to the configuration of the outlet of the impactor nozzle 104 from which the exemplary volume of fluid is dispensed prior to impacting the collection media 106. For example, the area of the collection media 106 that receives particles from a volume of fluid may be defined at least in part by the shape of the outlet of the impactor nozzle 104 and the distance between the nozzle outlet and the collection media 106. Accordingly, the outlet of the impactor nozzle 104 may be configured so as to comprise a shape that corresponds with the shape of the field of view of the imaging device 110 of the sensor 100. Specifically, the outlet of the impactor nozzle 104 may be configured so as to define a shape that is at least substantially similar to the size and shape of the field of view of the imaging device 110 of the sensor 100. As described herein, in various embodiments, the field of view of the imaging device 110 may have an aspect ratio of up to 1:20, so as to optimize the field of view based at least in part on one or more fluid flow characteristics of the volume of fluid. For example, in an exemplary circumstance wherein the field of view is defined by an aspect ratio of 3:4 having a defined size, the outlet of the impactor nozzle 104 may comprise a rectangular cross-section with a length-to-width ratio of 3:4 and having the same defined size (e.g., shape and/or area), corresponding to the configuration of the imaging device 110. For example, the impactor nozzle 104 may comprise a rectangular cross-section with a length of at least substantially between 1 mm and 10 mm (between 3 mm and 3.6 mm) and a width of at least substantially between 1 mm and 10 mm (between 3.9 mm and 4.5 mm).

Further, in various embodiments, the fluid composition sensor 100 may be configured such that a central axis of the impactor nozzle 104 is at least substantially aligned with the field of view of the imaging device 110 in order to facilitate the convergence of the field of view of the imaging device 110 and the portion of the collection media 106 configured to receive particles from the volume of fluid flowing through the sensor 100. As described herein, in order to ensure proper alignment of each of the aforementioned components, the fluid composition sensor 100 may be configured to secure the collection media 106, the impactor nozzle 104, and the imaging device 110 within the internal sensor portion 102 (e.g., temporarily during the execution of the particle collection and/or particle analysis functions) in each of the x-direction, the y-direction, the z-direction, and the angular direction. For example, the fluid composition sensor 100 may be configured such that the collection media 106 is arranged therein at a predetermined distance away from both the imaging device 110 and the outlet of the impactor nozzle 104, respectively, wherein both the distance between the collection media 106 and the imaging device 110 and the distance between the collection media 106 and the and the outlet of the impactor nozzle 104 are calibrated to optimize the particle collection and particle analysis functions of sensor 100, as described herein.

In various embodiments, a device 10 may experience increased inaccuracies over time, for example, as the number of particles collected within the collection media 106 increases (and the resulting physical properties of the collection media 106 changes as a result of the increase number of particles disposed therein. Thus, one or more components of the collection media assembly as described herein may be replaceable. In various embodiments, replacing one or more components of the collection media assembly may comprise removing one or more components from the fluid composition sensor 100 and replacing the one or more components of the collection media assembly with one or more at least substantially similar components. Alternatively, it should be understood that in various embodiments, replacing one or more components of the collection media assembly may comprise cleaning, repositioning, and/or modifying the one or more components of the collection media assembly so as to decrease the number of particles present within a portion of the collection media 106 exposed to the air flow within the composition sensor 100. As a non-limiting example, in various embodiments wherein the collection media assembly may comprise an adhesive tape, at least a portion of the tape may be removed so as to expose a fresh portion of tape positioned thereunder and corresponding to the at least a portion of the tape that was removed. As a further non-limiting example, in various embodiments wherein the collection media assembly may comprise a disc, the disc may be configured to be cleaned such that the characteristics of the disc may be at least substantially similar to those of a new disc. In various embodiments, the fluid composition sensor 100 may in part or in whole be configured to be replaceable and/or disposable.

As described herein, in various embodiments, a fluid composition sensor 100 may be configurable between an open housing configuration and a closed configuration. In various embodiments, the open housing configuration of a fluid composition sensor 100 may facilitate the removal of one or more sensor components from within the internal sensor portion 102. For example, a fluid composition sensor 100 in an open housing configuration may be configured so as to allow for the reconfiguration of a collection media assembly relative to at least a portion of the internal sensor portion 102 of the housing 101. In various embodiments wherein the fluid composition sensor 100 is in an open configuration, a collection media assembly comprising a collection media 106 disposed therein may be removed from a particle collection position within the internal sensor portion 102 of the fluid composition sensor 100. For example, upon determining that at least substantially the entirety of a sample volume of fluid has passed across a surface of the collection media 106 and that the one or more images of the particles needed to enable the particle analysis function of the sensor 100 have been captured, the collection media assembly may be removed from the internal sensor portion 102 and transported to an exemplary secondary location, such as, for example, a storage compartment and/or an incubation chamber, as described in further detail herein. While the fluid composition sensor 100 is in an open configuration, the removed collection media assembly may be replaced with a different, unused replaceable collection media assembly.

FIGS. 4A and 4B illustrate various exploded views of collection media assemblies in accordance with exemplary embodiments described herein. As shown in FIGS. 4A and 4B, an exemplary collection media assembly 150 may comprise one or more collection media 106 disposed upon a transparent substrate 108. In various embodiments, an exemplary collection media 106 may be formed at least in part using an absorbent media and a volume of collection fluid. For example, as illustrated in FIG. 4A, in various embodiments, an absorbent media 106b may be disposed at, on, within, and/or at least substantially adjacent a transparent substrate 108 surface so as to cover at least a portion of the surface area of the transparent substrate 108 surface. In various embodiments, the absorbent media 106b may comprise an at least partially absorbent material configured to receive a volume of collection fluid 106a that may be dispensed onto a absorbent media receiving face of the absorbent media material 106b and at least partially absorb the volume of collection fluid 106a such that at least substantially all of the volume of collection fluid 106a received by the absorbent media 106b is retained within an internal volume thereof. As a non-limiting example, in various embodiments, the absorbent media 106b may comprise a filter media, such as, for example, a Mixed Cellulose Ester (MCE) filter paper. For example, the physical configuration of an absorbent media 106b may be defined at least in part by a absorbent media receiving surface area, a absorbent media shape, a absorbent media thickness, and an absorbent media volume. For example, in various non-limiting embodiments, an exemplary substrate 108 may be defined at least in part by an at least substantially continuous absorbent media 106b such that a resultant collection media 106 may be formed by selectively dispensing the volume of collection fluid 106a at one or more predefined surface portions of the at least substantially continuous absorbent media 106b. In such an exemplary circumstance, for example, one or more predefined surface portions of the at least substantially continuous absorbent media 106b may be pre-treated using one or more chemical agents and/or other treatment means so as to disproportionately increase the uptake capacity of the at least substantially continuous absorbent media 106b at the one or more predefined surface portions, thereby minimizing the variance associated with the positioning of one or more resultant collection media 106 generated by a dispensed volume of collection fluid 106a.

In various embodiments, the absorbent media receiving surface area of an exemplary absorbent media 106b may be defined by the surface area of a absorbent media receiving face through which the absorbent media 106b may receive a volume of collection fluid. For example, in various embodiments, the absorbent media receiving surface area of an exemplary absorbent media 106b may be at least substantially between 0.0001 inches$^2$ and 50.0 inches$^2$ (e.g., between 0.001 inches$^2$ and 1.0 inch). Further, various embodiments, the absorbent media thickness of an exemplary absorbent media 106b may be defined by the perpendicular distance between the absorbent media receiving surface and the surface of the transparent substrate 108 arranged at least substantially adjacent the absorbent media 106B. For example, in various embodiments, the absorbent media thickness of an exemplary absorbent media 106b may be at least substantially between 0.00004 inches and 0.04 inches (e.g., between 0.0004 inches and 0.008 inches). Further, in various embodiments, the absorbent media thickness of an exemplary absorbent media 106b may at least partially define an absorbent media volume. For example, in various embodiments, the absorbent media volume of an exemplary absorbent media 106b may be at least substantially between 0.00006 inches$^3$ and 2.0 inches$^3$ (e.g., between 0.0001 inches$^3$ and 0.002 inches$^3$). In various embodiments, an exemplary absorbent media 106b may comprise any applicable shape (e.g., circular, rectangular, polygonal, and/or the like) or form configured to receive a volume of collection fluid 106a that may be dispensed thereon, as described herein. In various embodiments, at least a portion of an absorbent media 106b may be pre-treated (e.g., at an instance prior to a volume of collection fluid 106a being applied thereto) using one or more chemical agents so as to at least substantially maximize a retention capacity of the absorbent media 106b with respect to the collection media 106a.

Further, in various embodiments, the volume of collection fluid 106a may comprise a volume of fluid, such as, for example, a liquid, configured to be dispensed and/or applied to the absorbent media 106b. As described herein, an exemplary collection fluid 106a may comprise a fluid configured to, upon engaging the absorbent media 106b, initiate a reaction with the absorbent media 106b so as to produce a resultant collection media 106 that is disposed upon the transparent substrate 108 and configured to receive a one or more particles from within a fluid sample. As a non-limiting example, in various embodiments, the volume of collection fluid 106a may comprise a volume of Triacetin. Further, in various embodiments, a volume of collection fluid 106a may comprise a volume of a biological nutrient fluid configured to react with an absorbent media 106b so as to generate a resultant collection media 106 that comprises a biologically nutritive substance, such as, for example, agar, gelatin-based gels, and/or the like, that includes a nutritional component and/or a collection media moisture characteristic that is sufficient to facilitate biological growth of one or more particles disposed therein during an incubation operation, as described herein. In various embodiments, as described in further detail herein, an exemplary collection fluid 106a may be configured to facilitate the selective dispense thereof by a collection fluid assembly of an exemplary fluid composition sensor 100. As illustrated, in various embodiments, a volume of collection fluid 106a may be provided in an at least substantially downward vertical direction (e.g., at least substantially along a z-axis) to an upward-facing absorbent media receiving face of an absorbent media 106b disposed on a transparent substrate 108. In various embodiments, the amount of collection fluid 106a within a dispensed volume of collection fluid may be based at least in part on one or more filter characteristics of the absorbent media 106b onto which the volume of collection fluid 106a is to be dispensed, such as, for example, an absorbent media material, a absorbent media thickness, an absorbent media volume, and/or the like. As described in further detail herein, in various embodiments, the dispensed volume of collection fluid 106a that may be received by an absorbent media 106b so as to initiate a reaction sufficient to produce a collection media 106 may be at least substantially between 0.001 mL and 5.0 mL (e.g., between 0.01 mL and 1.0 mL).

In various embodiments, an exemplary collection media 106 formed by a volume of collection fluid 106a applied to an absorbent media 106b may be configured to receive one or more particles of a plurality of particles within a fluid sample via interaction with the fluid sample. In various embodiments, such an exemplary collection media 106 may comprise a receiving surface, a backside, and a thickness defined by the distance between the receiving surface and the backside. For example, the receiving surface of a collection media 106 may face an at least substantially upward direction (e.g., along the z-axis), while the backside may be positioned at least substantially adjacent (e.g., secured directly to) a transparent substrate 108. In various embodiments, the thickness of such an exemplary collection media 106 may be at least substantially between about 10 and about 1000 microns, (e.g., 100 microns). In various embodiments, such an exemplary collection media 106 may comprise a material suitable to stop one or more particles (e.g., received from within a fluid sample) traveling at a velocity into the receiving surface before the particle reaches the backside, such that the one or more received particles are disposed within the collection media at a distance along the thickness of the collection media 106. For example, in various embodiments, an exemplary collection media formed upon a reaction between an absorbent media 106b and a volume of collection fluid 106a received therein may comprise an adhesive (i.e. sticky) material, such as a gel.

In various embodiments, as described in further detail herein, a plurality of collection media assemblies 150 may each be disposed about respective portions of the same transparent substrate 108. In such an exemplary embodiment, the plurality of collection media assemblies 150 disposed upon a singular transparent substrate 108 may be defined at least in part by a plurality of collection media 106 disposed about a surface of the singular transparent substrate 108. In various embodiments wherein a plurality of collection media assemblies 150 comprising a plurality of collection media 106 are disposed upon a singular transparent substrate 108, the plurality of collection media 106 may be formed by a plurality of absorbent media disposed at, on, within, and/or at least substantially adjacent the transparent substrate 108 surface so as to cover respective portions of the surface area of the transparent substrate 108. In such an exemplary circumstance, each of the plurality of absorbent media may be configured to receive a respective volume of collection fluid, as described in further detail herein. For example, as illustrated in FIG. 4B, a plurality of collection media assemblies 150 disposed upon a singular transparent substrate 108 may comprise a first collection media 1061, a second collection media 1062, and a third collection media 1603. As illustrated, each of the plurality of collection media 1061, 1062, 1063 may be formed by a respective absorbent media 1061b, 1062b, 1063b arranged about the transparent substrate 108 surface. In such an exemplary circumstance, each of the plurality of absorbent media 1061b, 1062b, 1063b may be configured to receive a respective volume of collection fluid 1061a, 1062a, 1063a. For example, the respective volumes of collection fluid 1061a, 1062a, 1063a may be provided to the respective absorbent media 1061b, 1062b, 1063b in an at least substantially downward vertical direction (e.g., at least substantially along a z-axis).

In various embodiments, the plurality of absorbent media 1061b, 1062b, 1063b may be spaced apart from one another about the transparent substrate 108 so as to define an at least substantially even distribution. As a non-limiting example, the plurality of absorbent media 1061b, 1062b, 1063b may be at least substantially evenly spaced apart from one another along a length of the transparent substrate 108. As described in further detail herein, the first, second, and third absorbent media 1061b, 1062b, 1063b may be arranged about a substrate 108 so as to facilitate one or more sequential collection fluid dispense operations, wherein the first, second, and third absorbent media 1061b, 1062b, 1063b may receive a first volume of collection fluid 1061a, a second volume of collection fluid 1062a, and a third volume of collection fluid 1063a, respectively, sequentially from a singular collection fluid dispense assembly (e.g., dispense nozzle) as the transparent substrate 108 and/or the plurality of collection media assemblies 150 are moved (e.g., linearly shifted) relative to the collection fluid dispense assembly.

FIGS. 5A-5B illustrate various views of a collection media assembly in accordance with various embodiments as described herein. As shown in FIGS. 5A and 5B, the collection media assembly 150 may comprise at least one collection media 106 disposed upon a transparent substrate 108. In various embodiments, as described herein, an exemplary collection media 106 may comprise an absorbent media portion and a collection fluid portion. For example, an exemplary collection media 106 may be formed at least in part using an absorbent media that may be disposed at, on, within, and/or at least substantially adjacent a transparent substrate 108 and may comprise an at least partially absorbent material configured to receive and/or at least partially absorb a volume of collection fluid 106 that may be dispensed thereon. In various embodiments, an absorbent media that defines the absorbent media portion of an exemplary collection media 106 may be configured to retain the volume of collection fluid dispensed thereon within an internal volume thereof, and may be further configured to react with the retained volume of collection fluid so as to produce and a collection media 106, as described herein. In such an exemplary circumstance, the collection fluid portion of an exemplary collection media 106 may be defined by the volume of collection fluid retained within the absorbent media so as to react with the absorbent media to produce the collection media 106.

In various embodiments, as illustrated in FIG. 5A, an exemplary collection media assembly 150 may further comprise an air seal engagement portion 115A surrounding the collection media 106 and the transparent substrate 108. In various embodiments, the transparent substrate 108 may be defined by a replaceable slide, as described herein. In various embodiments, the air seal engagement portion 115A may define at least a portion of a perimeter of the collection media assembly 150, such as a portion of the collection media assembly 150 that surrounds one of the at least one collection media 106 corresponding thereto. In various embodiments, the air seal engagement portion 115A may be used to prevent or limit exposure of adjacent or nearby collection media 106 sections to a volume of collection fluid being dispensed (e.g., by a collection fluid dispense assembly within a collection fluid dispense chamber) and/or to a volume of fluid being sampled (e.g., by a fluid composition sensor via an impaction nozzle). In certain embodiments, the air seal engagement portion 115A may be embodied as a rigid, at least substantially smooth component configured to interact with a gasket (or other flexible sealing component) of an air seal component of a device as discussed herein. As another example, the air seal engagement portion 115A may comprise one or more flexible components (e.g., a resilient gasket) configured to interact with corresponding components of an air seal component of a device so as to form an at least substantially fluid tight seal therebetween. In various embodiments, a collection media assembly 150 may include one or more orifice extending through a thickness of transparent substrate 108 and disposed at least substantially adjacent a collection media 106 so as to facilitate a continuous flow of a fluid sample over the collection media 106 and along a fluid flow path in an otherwise fluidly sealed (e.g., air-tight) environment. For example, the air seal engagement portion 115A may be configured to receive and/or engage an air seal component of the fluid composition sensor such that at least substantially all of a volume of fluid flowing through the fluid composition sensor flows through the one or more orifice surrounded by the at least one seal engagement portion 115A. As shown in FIG. 5A, the air seal engagement portion 115A may comprise a portion of a surface of the transparent substrate 108. In various embodiments, as described herein, the air seal engagement portion 115A may comprise a plurality of air seal engagement portions, each corresponding to a respective collection media 106 of the at least one collection media corresponding thereto.

In various embodiments, an exemplary collection media assembly 150 may further comprise one or more identification elements configured to uniquely identify the particular collection media 106 corresponding thereto. The identification element 127 may comprise, for example, a bar code, QR code, serial number, and/or the like. In various embodiments, the identification element 127 may be disposed upon and/or within the transparent substrate 108 of the collection media assembly 150. In such a configuration, the identification element 127 may be positioned about the collection media assembly 150 such that the identification element 127 may be captured and/or identified by an imaging device disposed either within or external to the fluid composition sensor, as described herein. Further, in various embodiments, a controller of the fluid composition sensor, as described herein, may be used in combination with the aforementioned imaging device to facilitate the identification and/or processing of the collection media assembly 150 based at least in part on the identification element 127. For example, in various embodiments, first particle data comprising first timestamp data and second particle data comprising second timestamp data, as described herein, may each be captured by an exemplary fluid composition sensor 100 (e.g., via an imaging device) and associated with the same identification element 127. In various embodiments, an exemplary fluid composition sensor 100 may be configured to determine that the first particle data and the second particle data each relate to the same collection media assembly (e.g., the same collection media 106) based at least in part on an identification of the identification element 127.

FIG. 5B illustrates a cross-sectional view of an exemplary collection media assembly in accordance an embodiment described herein. As shown, the collection media assembly 150 may comprise a collection media housing 113. In various embodiments, the collection media housing 113 may be configured to at least partially surround the transparent substrate 108 so as to embody an outer frame of the collection media assembly 106. In various embodiments, as described herein, the at least one seal engagement portion (e.g., seal engagement portion 115A) of the collection media assembly 150 may comprise a portion of the collection media housing 113. In various embodiments, the collection media housing 113 may be configured to facilitate the collective storage (e.g., stacking) and subsequent dispensing of each of a plurality of collection media assemblies 150 into an internal sensor portion of a fluid composition sensor. For example, as described herein, the collection media housing 113 of each of the plurality of collection media assemblies 150 may be configured to receive a force from one or more components of the exemplary device described herein (e.g., an actuator element) such that each collection media assembly 150 may be consecutively transmitted in series from an initial storage location to one or more downstream configurations within an exemplary fluid composition sensor, such as, for example, a collection fluid dispense chamber, an internal sensor portion, an incubation chamber, a storage chamber, and/or the like. As illustrated in FIG. 5B, the exemplary collection media 106 may comprise an absorbent media portion defined by absorbent media 106b disposed about the substrate 108 and a collection fluid portion defined by a volume of collection fluid 106a applied to the absorbent media 106b. It should be understood that, although FIG. 5B illustrates the volume of collection fluid 106a and the absorbent media 106b of the collection media as being arranged in a stacked configuration wherein the volume of collection fluid 106a is disposed on top of the absorbent media 106b and remains distinct from the absorbent media 106b, such a configuration has been included for illustrative purposes and should not be interpreted as a limiting embodiment in any way. For example, as described herein, in various embodiments, an absorbent media 106b may be configured to receive and/or at least partially absorb the volume of collection fluid 106 applied thereto such that the volume of collection fluid 106a is retained within an internal volume of the absorbent media 106b and the exemplary collection media 106 is defined at least in part by the fluid interaction between the collection fluid 106a and the absorbent media 106b.

Figure 6:
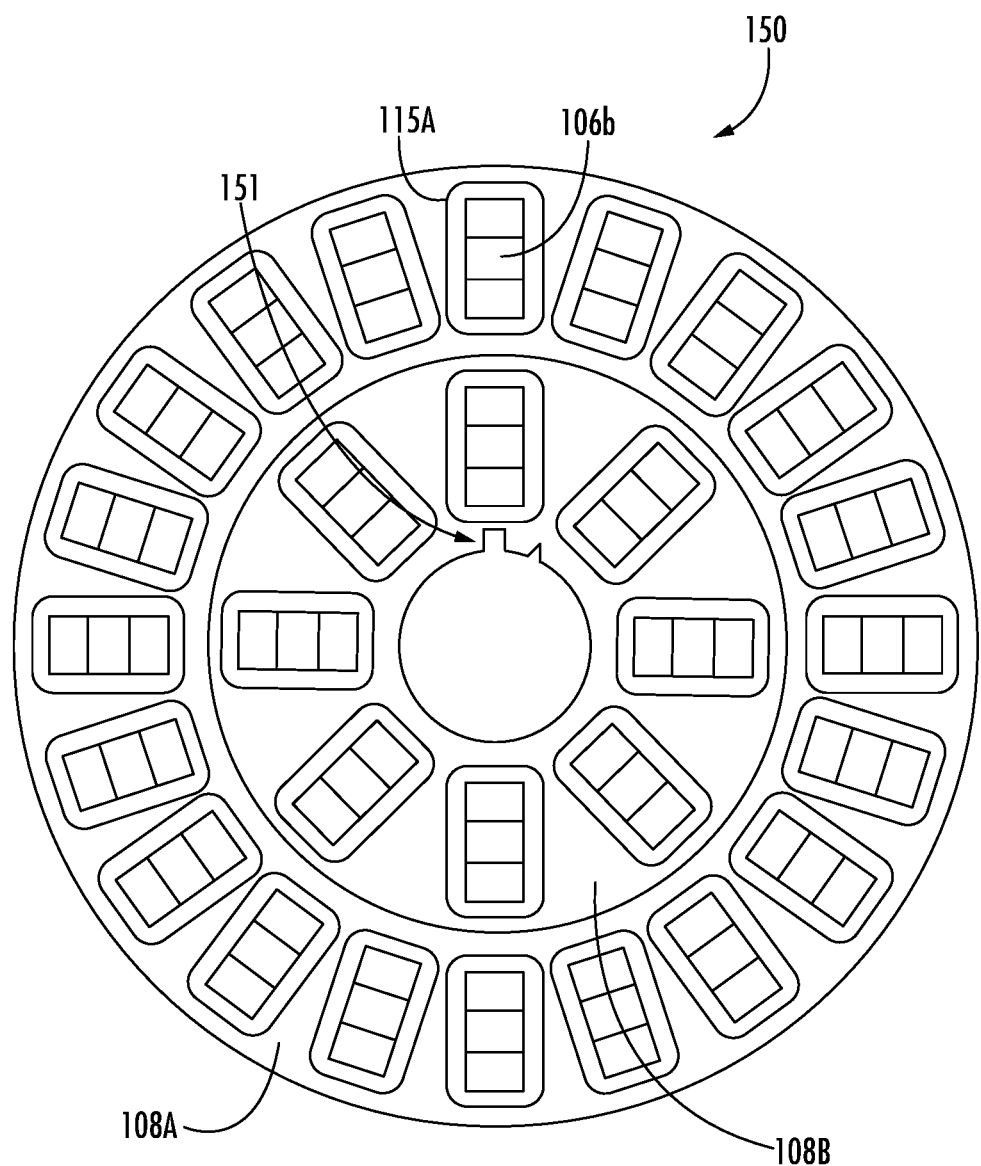
FIG. 6 illustrates a top view of a collection media assembly in accordance with an exemplary embodiment described herein.
Figure 7:
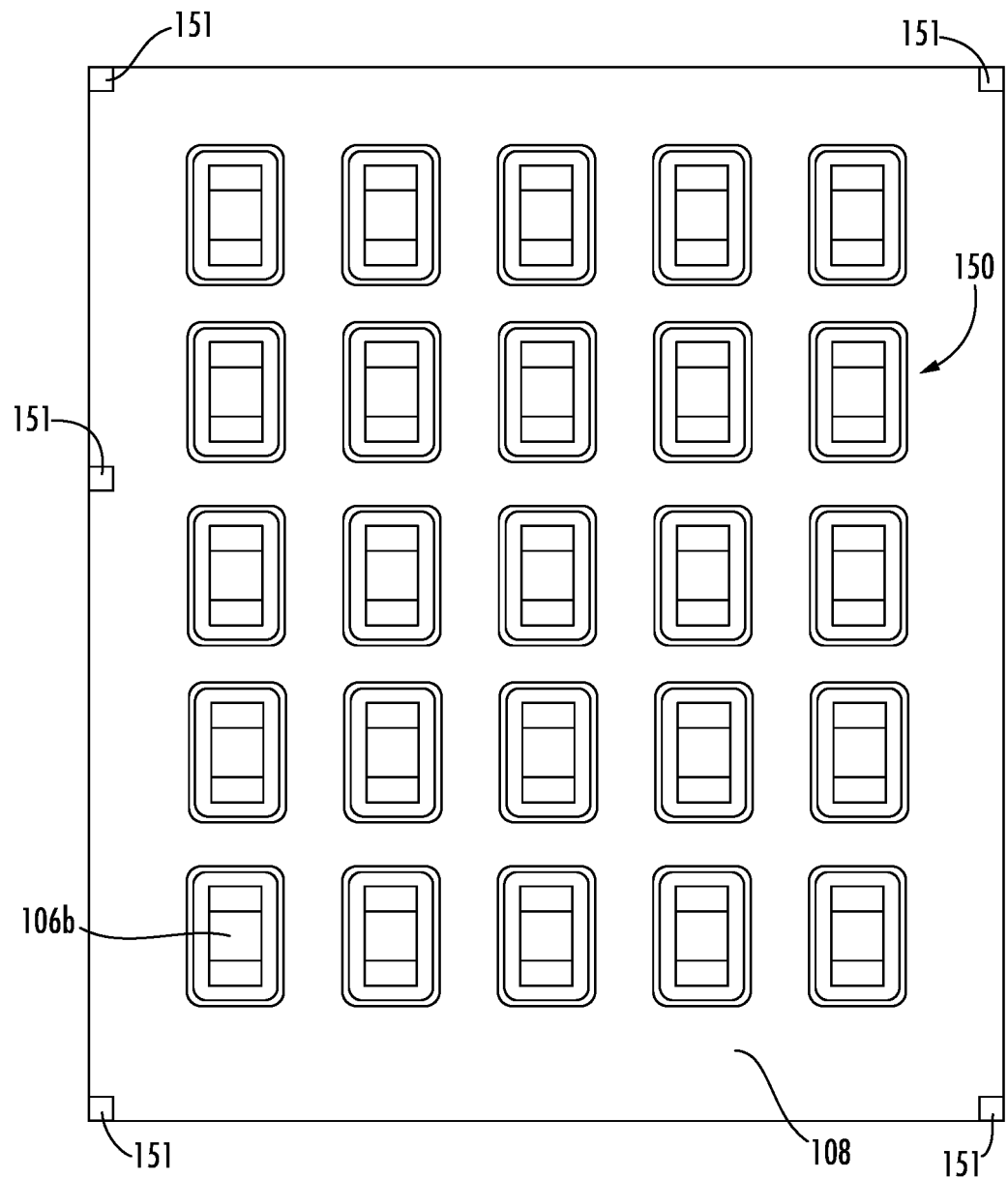
FIG. 7 illustrates a top view of a collection media assembly in accordance with an exemplary embodiment described herein.
Figure 8:
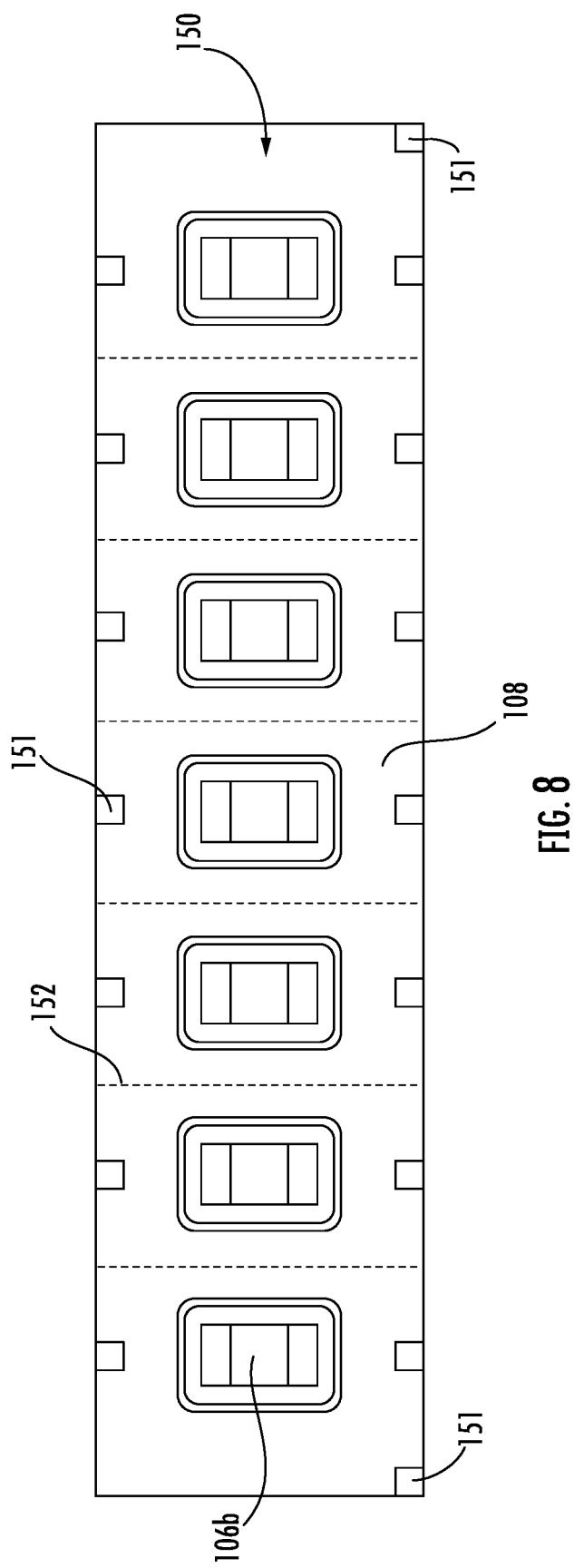
FIG. 8 illustrates a top view of a collection media assembly in accordance with an exemplary embodiment described herein.

FIGS. 6-8 illustrate various collection media assemblies in accordance with exemplary embodiments described herein. FIG. 6 illustrates a top view of a plurality of collection media assemblies disposed upon a rotatable disc in accordance with an exemplary embodiment. In various embodiments, a plurality of collection media assemblies 150 may be disposed upon a rotatable disc that may be rotatable about an axis such that the plurality of collection media assemblies 150 (e.g., comprising a plurality of collection media 106) may move relative to an internal sensor portion of a housing of a fluid composition sensor. In various embodiments, the plurality of collection media assemblies 150 disposed upon a rotatable disc may comprise a plurality of absorbent media 106b disposed about the rotatable disc such that, upon rotation of the rotatable disc, the plurality of absorbent media 106b may move relative to a collection fluid dispense chamber within an internal sensor portion of an exemplary fluid composition sensor. As a non-limiting example, the plurality of collection media assemblies 150 may be disposed upon a rotatable disc that may be rotatable about an axis such that at least a portion of the plurality of collection media 106 (e.g., one or more of a plurality of absorbent media 106b) of the collection media assemblies 150 may move relative to a collection fluid dispense chamber. In various embodiments, the rotatable disc may be configured such that one or more absorbent media 106b disposed thereon may be moved (e.g., rotated) relative to the fluid composition sensor such that a fresh (e.g., unreacted) absorbent media 106b of the plurality of collection media assemblies 150 may be exposed to a volume of collection fluid selectively dispensed within a collection fluid dispense chamber in order to produce a collection media 106 disposed on the rotatable disc, as described herein. Further, the rotatable disc may be configured such that the plurality of collection media 106 may be moved (e.g., rotated) relative to the fluid composition sensor such that a fresh (e.g., unused) collection media 106 of the plurality of collection media assemblies 150 may be exposed to a volume of fluid flowing through an impactor nozzle, as described herein.

In various embodiments, the rotatable disc may comprise a coplanar and concentric plurality of disc portions, each of the disc portions comprising portion of the rotatable disc upon which one or more of the plurality of collection media assemblies 150 may be disposed. For example, as illustrated in FIG. 6, the rotatable disc may comprise a first disc portion 108A and a second disc portion 108B, upon each of which is a plurality of collection media assemblies 150 (e.g., a plurality of absorbent media 106b). Each of the disc portions may be defined at least in part by a corresponding radial distance between the disc portion and the central axis of the rotatable disc, wherein the radial distance corresponding to each of the disc portions comprises a distinct value such that the plurality of disc portions may define a plurality of circumferential layers extending radially outwardly from the central axis of the rotatable disc. The plurality of disc portions may be configured to increase the capacity of rotatable disc with respect to the number of collection media 106 disposed thereon. In various embodiments, the exemplary device described herein may be configured such that the rotatable disc may be rotated and/or moved linearly (e.g., in a radial direction relative to the disk) relative to the fluid composition sensor so as to position an unused absorbent media 106b of the plurality of collection media assemblies 150 at least substantially adjacent an outlet of a collection fluid dispense nozzle of the fluid composition sensor, as described herein. Further, in various embodiments, the exemplary device described herein may be configured such that the rotatable disc may be rotated and/or moved linearly (e.g., in a radial direction relative to the disk) relative to the fluid composition sensor so as to position an unused collection media 106 of the plurality of collection media assemblies 150 at least substantially adjacent an outlet of an impactor nozzle of the fluid composition sensor, as described herein.

As described herein, each of the plurality of collection media 106 (e.g., the plurality of absorbent media 106b) of the plurality of collection media assemblies 150 may be disposed upon a transparent substrate. In various embodiments, at least a portion of the rotatable disc upon which the plurality of collection media 106 is disposed may comprise a transparent substrate, however opaque or translucent materials may be utilized for defining portions of the disk between included collection media assemblies 150. For example, in various embodiments, the entirety of the rotatable disc may comprise a transparent substrate. Further, in various embodiments, the rotatable disc may comprise one or more alignment keys 151 configured to assist with the manual and/or mechanical installation and/or alignment of an absorbent media 106b and/or a collection media 106 disposed upon the rotatable disc in a position such that a volume of collection fluid dispensed from the collection fluid dispense assembly (e.g., within the collection fluid dispense chamber) may be applied to a surface of the absorbent media 106b and/or such that a volume of fluid flowing through the fluid composition sensor (e.g., through the impactor nozzle) may be passed across a surface of the collection media 106. In various embodiments, each of the plurality of collection media assemblies 150 may comprise an air seal engagement portion 115A surrounding a corresponding one of the plurality of collection media 106 and one or more orifices positioned adjacent thereto. In such a configuration, a volume of fluid flowing through the sensor may be passed across a surface of the collection media 106 surrounded by an air seal engagement portion 115A engaged with an air seal component of the fluid composition sensor, as described herein. For example, the collection media 106 surrounded by an air seal engagement portion 115A engaged with an air seal component of the fluid composition sensor may be fluidly isolated from each of the other collection media of the plurality of collection media disposed upon the rotatable disc.

FIG. 7 illustrates a top view of a plurality of collection media assemblies disposed upon an alignment plate in accordance with an exemplary embodiment. In various embodiments, a plurality of collection media assemblies 150 may be disposed upon an alignment plate that may be moveable about a plane such that the plurality of collection media assemblies 150 (e.g., comprising a plurality of collection media 106) may move relative to an internal sensor portion of a housing of a fluid composition sensor. In various embodiments, the plurality of collection media assemblies 150 disposed upon a rotatable disc may comprise a plurality of absorbent media 106b disposed about the alignment plate such that, upon a movement of the alignment plate, the plurality of absorbent media 106b may move relative to a collection fluid dispense chamber within an internal sensor portion of an exemplary fluid composition sensor. As a non-limiting example, the plurality of collection media assemblies 150 may be disposed upon an alignment plate that may move relative to a collection fluid dispense chamber such that at least a portion of the plurality of collection media 106 (e.g., one or more of a plurality of absorbent media 106b) of the collection media assemblies 150 may move relative to a collection fluid dispense chamber. In various embodiments, an exemplary device described herein may be configured such that the alignment plate may be moved (e.g., linearly shifted) along at least two directional axes (e.g., an x-axis and a y-axis existing within a plane) relative to the fluid composition sensor such that a fresh (e.g., unused) absorbent media 106b of the plurality of collection media assemblies 150 may be exposed to a volume of collection fluid dispensed within a collection fluid dispense chamber of the fluid composition sensor, as described herein. Further, the alignment plate may be configured such that the plurality of collection media 106 may be moved (e.g., linearly shifted) along at least two directional axes (e.g., an x-axis and a y-axis existing within a plane) relative to the fluid composition sensor such that a fresh (e.g., unused) collection media 106 of the plurality of collection media assemblies 150 may be exposed to a volume of fluid flowing through an impactor nozzle, as described herein. As illustrated in FIG. 7, in various embodiments, the plurality of collection media assemblies 150 (e.g., a plurality of absorbent media 106b) disposed upon the alignment plate may be arranged so as to define an array comprising plurality of rows and columns.

As described herein, each of the plurality of collection media 106 (e.g., one or more of a plurality of absorbent media 106b) of the plurality of collection media assemblies 150 may be disposed upon a transparent substrate. In various embodiments, at least a portion of the alignment plate upon which one or more absorbent media 106b is disposed may comprise a transparent substrate. For example, in various embodiments, the entirety of the alignment plate may comprise a transparent substrate (however, portions of the alignment plate between the collection media assemblies may comprise opaque or translucent materials in certain embodiments). Further, in various embodiments, the alignment plate may comprise one or more alignment keys 151 configured to assist with the manual and/or mechanical installation and/or alignment of an absorbent media 106b and/or a collection media 106 disposed upon the alignment plate in a position such that a volume of collection fluid dispensed from the collection fluid dispense assembly (e.g., within the collection fluid dispense chamber) may be applied to a surface of the absorbent media 106b and/or such that a volume of fluid flowing through the fluid composition sensor (e.g., through the impactor nozzle) may be passed across a surface of the collection media 106. In various embodiments, the one or more alignment keys 151 may be arranged about the alignment plate so as to correspond to a particular row and a particular column of the array defined by the plurality of collection media assemblies 150.

FIG. 8 illustrates a top view of a plurality of collection media assemblies disposed upon an alignment tape in accordance with an exemplary embodiment. In various embodiments, a plurality of collection media assemblies 150 may be disposed upon an alignment plate that may be moveable in a direction at least substantially parallel with a linear axis extending along the length of the alignment tape such that the plurality of collection media assemblies 150 (e.g., comprising a plurality of collection media 106) disposed thereon may move relative to an internal sensor portion of a housing of a fluid composition sensor. In various embodiments, the plurality of collection media assemblies 150 disposed upon a rotatable disc may comprise a plurality of absorbent media 106*b* disposed about the length of the alignment tape such that, upon a movement of the alignment tape in a direction at least substantially parallel with the linear axis extending along the length of the alignment tape, the plurality of absorbent media 106*b* may move relative to a collection fluid dispense chamber within an internal sensor portion of an exemplary fluid composition sensor. As a non-limiting example, the plurality of collection media assemblies 150 may be disposed upon an alignment tape that may move relative to a collection fluid dispense chamber such that at least a portion of the plurality of collection media 106 (e.g., one or more of a plurality of absorbent media 106*b*) of the collection media assemblies 150 may move relative to a collection fluid dispense chamber. In various embodiments, an exemplary device described herein may be configured such that the alignment tape may be moved (e.g., linearly shifted) in a direction at least substantially parallel with the linear axis extending along the length of the alignment tape relative to the fluid composition sensor such that a fresh (e.g., unused) absorbent media 106*b* of the plurality of collection media assemblies 150 may be exposed to a volume of collection fluid dispensed within a collection fluid dispense chamber of the fluid composition sensor, as described herein. Further, the alignment tape may be configured such that the plurality of collection media 106 may be moved (e.g., linearly shifted) relative to the fluid composition sensor such that a fresh (e.g., unused) collection media 106 of the plurality of collection media assemblies 150 may be exposed to a volume of fluid flowing through an impactor nozzle, as described herein. As illustrated in FIG. 8, in various embodiments, the plurality of collection media assemblies 150 (e.g., a plurality of absorbent media 106*b*) disposed upon the alignment tape may be arranged so as to define a row of collection media assemblies 150 extending along the length of the alignment tape.

In various embodiments, at least a portion of the alignment tape upon which the plurality of collection media 106(e.g., one or more of a plurality of absorbent media 106*b*) is disposed may comprise a transparent substrate 108. In various embodiments, at least a portion of the alignment tape upon which one or more absorbent media 106*b* is disposed may comprise a transparent substrate. For example, in various embodiments, the entirety of the alignment tape may comprise a transparent substrate 108 (although it should be understood that portions of the alignment tape between collection media assemblies 150 may comprise an opaque or translucent material). Further, in various embodiments, the alignment tape may comprise one or more alignment keys 151 configured to assist with the manual and/or mechanical installation and/or alignment of an absorbent media 106*b* and/or a collection media 106 disposed upon the alignment tape in a position such that a volume of collection fluid dispensed from the collection fluid dispense assembly (e.g., within the collection fluid dispense chamber) may be applied to a surface of the absorbent media 106*b* and/or such that a volume of fluid flowing through the fluid composition sensor (e.g., through the impactor nozzle) may be passed across a surface of the collection media 106. In various embodiments, the one or more alignment keys 151 may be arranged about the alignment tape so as to correspond to a particular collection media assembly 150 of the row defined by the plurality of collection media assemblies 150.

In various embodiments, each of the plurality of collection media assemblies 150 may comprise an air seal engagement portion surrounding a corresponding one of the plurality of collection media 106 (e.g., one of the plurality of absorbent media 106*b*) and an at least one orifice positioned adjacent thereto. In such a configuration, a volume of collection fluid dispensed by a collection fluid dispense assembly within a collection fluid dispense chamber may be applied to and/or received at a surface of an absorbent media 106*b* that is surrounded by an air seal engagement portion 115A engaged with the a substrate surface 108 and/or an air seal component of the fluid composition sensor, as described herein. Further, in various embodiments, a volume of fluid flowing through the sensor may be passed across a surface of the collection media 106 surrounded by an air seal engagement portion 115A engaged with an air seal component of the fluid composition sensor, as described herein. For example, the collection media 106 surrounded by an air seal engagement portion that is engaged with an air seal component of the fluid composition sensor may be fluidly isolated from each of the other collection media of the plurality of collection media disposed upon the alignment tape. As described herein, in various embodiments, the alignment tape may comprise a non-rigid (e.g., flexible, bendable, foldable, and/or the like) material. For example, each of the plurality of collection media assemblies 150 (e.g., each of the plurality of absorbent media 106*b*) may be separated by a fold line 152, along which the alignment tape may be folded. In various embodiments, the non-rigid material of the alignment tape may facilitate the plurality of collection media assemblies 150 (e.g., unused absorbent media 106*b*, used collection media 106, and/or the like) being arranged so as to define a compact incubation configuration and/or a compact storage configuration, such that the capacity and operational efficiency of the fluid composition sensor may be increased.

Figure 9:
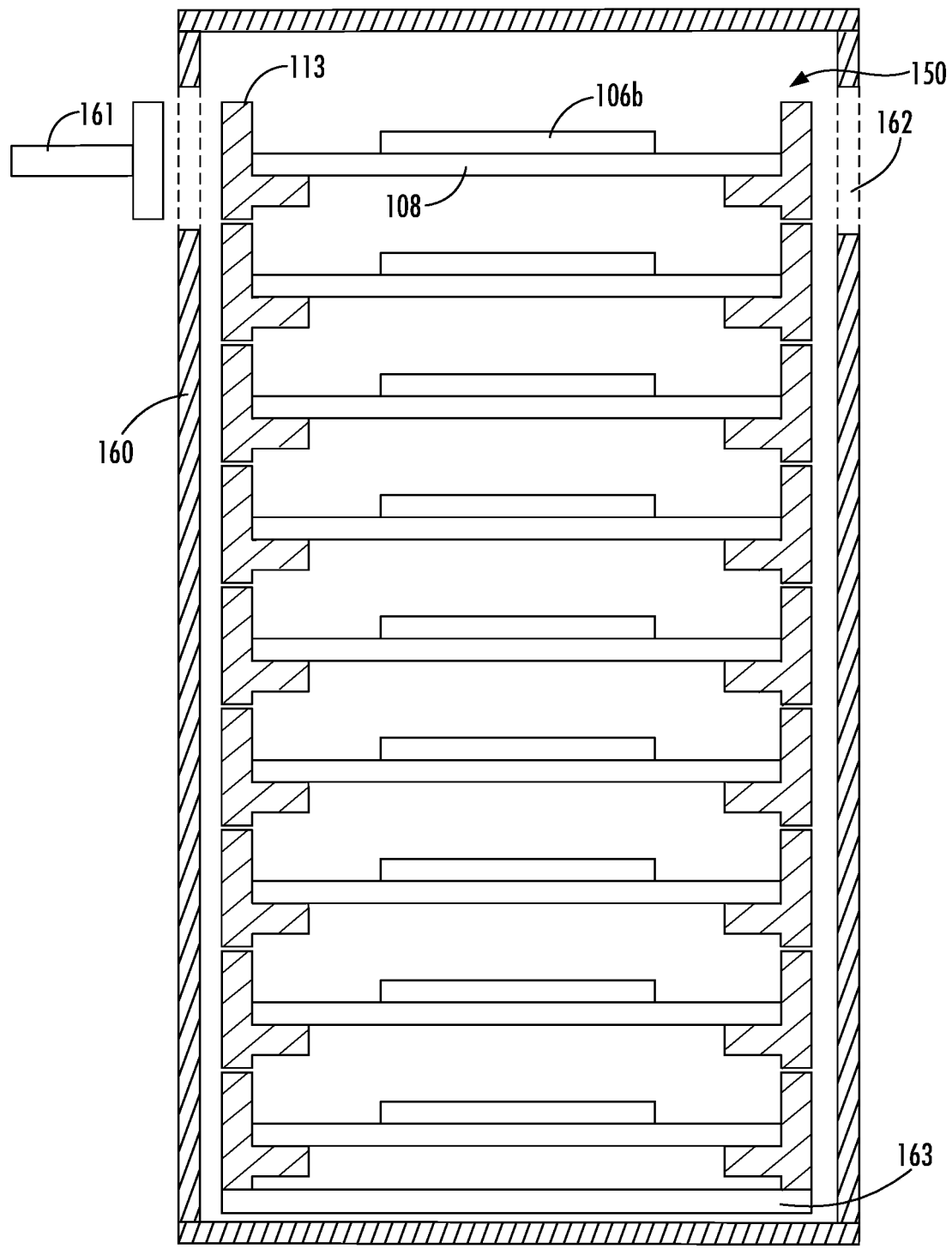
FIG. 9 illustrates a cross-sectional view of an exemplary apparatus in accordance with an exemplary embodiment described herein.

FIG. 9 illustrates a cross-sectional view of an exemplary apparatus in accordance with an embodiment described herein. In particular, FIG. 9 illustrates an exemplary collection media assembly storage chamber 160 configured to house at least a portion of a plurality of collection media. As described herein, in various embodiments, an exemplary collection media assembly 150 may comprise a replaceable cartridge, cassette, and/or the like configured so as to facilitate the collective storage (e.g., stacking) and subsequent dispensing of each of a plurality of collection media assemblies 150 into an internal sensor portion (e.g., into a collection fluid dispense chamber) of a fluid composition sensor. As illustrated in FIG. 9, a plurality of exemplary collection media assemblies 150 may be disposed within the collection media assembly storage chamber 160. In various embodiments, the collection media assembly storage chamber 160 may store a plurality of unused collection media assemblies prior to the plurality of collection media assemblies being respectively used in sequence for particle collection within a fluid composition sensor. For example, in various embodiments, the collection media assembly storage chamber 160 may store a plurality of unused collection media assemblies that each comprise a respective absorbent media 106b disposed upon a respective substrate 108 prior to the plurality of absorbent media 106b being selectively and/or sequentially dispensed from the collection media assembly storage chamber 160 for interaction with a collection fluid dispense assembly (e.g., one or more dispensed volumes of collection fluid) within a fluid composition sensor. In various embodiments, the collection media assembly storage chamber 160 may be configured so as to at least substantially minimize the exposure of each of the collection media assemblies 150 stored therein to an ambient environment in order to avoid a contamination of the corresponding absorbent media 106b. Further, the collection media assembly storage chamber 160 may be configured so as to facilitate the initial arrangement and/or ordering, and the subsequent repositioning of a plurality of absorbent media 106b so as to enable an automated and/or serial collection fluid dispense operation functionality within the fluid composition sensor.

As described herein, the collection media assembly storage chamber 160 may be further configured to consecutively transmit each of the plurality of collection media assemblies 150 stored therein in series to an internal sensor portion of a fluid composition sensor. For example, the collection media assembly storage chamber 160 may be configured to consecutively transmit each of a plurality of collection media assemblies 150 comprising respective absorbent media 106b stored therein in series to a collection fluid dispense chamber positioned operationally between the collection media assembly storage chamber 160 and a particle collection position within the fluid composition sensor. In various embodiments, the collection media assembly storage chamber 160 may comprise an actuator element 161 configured to selectively apply a force to one of the plurality of collection media assemblies stored within the collection media assembly storage chamber so as to reposition a collection media assembly 150 comprising an unused absorbent media 106b from the collection media assembly storage chamber 160 towards a collection fluid dispense chamber of the fluid composition sensor. For example, the actuator element 161 may be configured to move from a compressed position, as illustrated in FIG. 9, to an extended position. As the actuator element 161 moves from the compressed position to the extended position, the actuator element 161 may be configured to apply a force to a collection media assembly 150. In various embodiments, the force applied to the collection media assembly 150 as the actuator element 161 moves from the compressed position to the extended position may cause the collection media assembly and, thus, an unused absorbent media 106b disposed on a corresponding substrate 108, to be repositioned such that, when the actuator element 161 is in a first extended position, the absorbent media 106b of the displaced collection media assembly 150 may be in a collection fluid receiving position within the collection fluid dispense chamber of the fluid composition sensor. In various embodiments, a collection fluid receiving position may be defined by an arrangement of a collection media assembly 150 at least partially within a collection fluid dispense chamber wherein the corresponding absorbent media 106b is at least substantially aligned with a collection fluid dispense nozzle such that a volume of collection fluid dispensed from the collection fluid dispense assembly (e.g., via the collection fluid dispense nozzle) may be received by the absorbent media 106b in the collection fluid receiving position. In various embodiments, upon extending from a compressed position to a first extended position (e.g., so as to position a collection media assembly 150 in a collection fluid receiving position), the actuator element 161 may be configured to retract from the first extended position back to the compressed position. Alternatively, or additionally, upon extending from a compressed position to a first extended position, the actuator element 161 may be configured to extend further from the first extended position to a second extended position.

In such an exemplary circumstance, as the actuator element 161 moves from the first extended position to a second extended position, the actuator element 161 may be configured to apply a force to a collection media assembly 150. In various embodiments, the force applied to the collection media assembly 150 as the actuator element 161 moves from the compressed position to the extended position may cause the collection media assembly and, thus, a collection media 106 disposed on the corresponding substrate that was generated by a reaction between the volume of collection fluid dispensed from the collection fluid dispense assembly and the absorbent media 106b arranged in the collection fluid receiving position, to be repositioned such that, when the actuator element 161 is in a second extended position, the collection media 106 of the displaced collection media assembly 150 may be in a particle collection position within an internal sensor portion of the fluid composition sensor. In various embodiments, a particle collection position may be defined by an arrangement of a collection media assembly 150 within the internal sensor portion of the fluid composition sensor wherein the corresponding collection media 106 is positioned such that a volume of fluid flowing through the fluid composition sensor (e.g., through an impactor nozzle) may be passed across a surface thereof. In various embodiments, upon extending from a compressed position to an extended position (e.g., so as to position a collection media assembly 150 in a particle collection position), the actuator element 161 may be configured to retract from the second extended position back to the compressed position. Further, in various embodiments, the actuator element 161 may comprise a gear drive mechanism and/or a lever arm mechanism that may be configured to operate according to one or more embodiments described herein.

As illustrated, the collection media assembly storage chamber 160 may comprise a dispense opening 162 within one or more walls of the chamber, the dispense opening 162 being configured to allow one or more of the collection media assemblies 150 stored within the collection media assembly storage chamber 160 to pass therethrough as the one or more of the collection media assemblies 150 are being transmitted to the collection fluid dispense chamber of the fluid composition sensor. In various embodiments, the dispense opening 162 may comprise a dispense door that may be selectively opened and closed to facilitate the selective dispense of a collection media assembly 150. For example, in the exemplary embodiment illustrated in FIG. 9, the actuator element 161 may be configured to apply a transverse (e.g., horizontal) force on a collection media assembly 150 positioned in a loading position (e.g., at an uppermost position in a stack of collection media assemblies) so as to dispense the collection media assembly 150 from the collection media assembly storage chamber 160 through the dispense opening 162. As described herein, the collection media assembly storage chamber 160 may be positioned proximate a housing of the fluid composition sensor such that the housing is configured to receive the at least a portion of collection media assembly 150 dispensed from the collection media assembly storage chamber 160 via the dispense opening 162. Accordingly, the dispense opening 162 may be at least substantially coplanar with a collection fluid dispense chamber (e.g., a position of an absorbent media 106*b* when arranged to receive a volume of collection fluid dispensed from the collection fluid dispense assembly). As described above, the collection media assembly storage chamber 160 may be configured to dispense a collection media assembly 150 through a dispense opening 162 (e.g., using an actuator element 161) so as to deliver the collection media assembly 150 to a collection fluid receiving position within the collection fluid dispense chamber of the fluid composition sensor.

The collection media assembly storage chamber 160 may be configured to arrange the plurality of collection media assemblies 150 (e.g., the respective plurality of absorbent media 106*b*) within the storage chamber relative to one another such that they may be consecutively transmitted in series from a storage location to a collection fluid receiving position within the collection fluid dispense chamber of the fluid composition sensor, as described herein. For example, the collection media assembly storage chamber 160 may define a loading position arranged proximate and/or at least substantially planar with the actuator element 161 and/or the dispense opening 162, wherein a collection media assembly 150 positioned in a loading position may be the next collection media assembly 150 of the plurality disposed within the collection media assembly storage chamber 160 to be transmitted to a fluid composition sensor (e.g., sequentially before each of the other collection media assemblies stored within the collection media assembly storage chamber 160). As illustrated in FIG. 9, the plurality of collection media assemblies 150 stored within the collection media assembly storage chamber 160 may be arranged in a stack. As shown, the loading position may comprise the position proximate the actuator element 161 and/or the dispense opening 162 (e.g., the top of the stack). In various embodiments, the collection media assembly storage chamber 160 may comprise a loading element 163 configured to arrange the plurality of collection media assemblies 150 disposed within the collection media assembly storage chamber 160 such that, upon the dispense of a first collection media assembly, a second collection media is moved within the collection media assembly storage chamber 160 into a loading position. For example, the loading element 163 may comprise a plate configured to which a bias force may be applied such that the plate transmits a corresponding loading force to one or more of the plurality of collection media assemblies 150. In such an exemplary circumstance, a bias force may be applied (e.g., via a spring) to a bottom surface of the loading element 163 so as to push a subsequently stacked collection media assembly 150 of the plurality into the loading position. In various embodiments, the bias force applied to the loading element 163 and/or the loading force applied from the loading element 163 to one or more of the plurality of collection media assemblies 150 may be either a constant force or an intermittent force selectively applied between subsequent collection media assembly 150 dispenses in order to arrange the plurality of collection media assemblies such that at least one collection media assembly 150 is in a loading position.

FIGS. 10A-10D illustrate an exemplary fluid composition sensor in accordance with various embodiments. As described herein, a fluid composition sensor may comprise a housing 101, an illumination source 116, an impactor nozzle 104, and an imaging device 110. In various embodiments, as described herein, an exemplary fluid composition sensor 100 may be configured to receive at least a portion of a plurality of collection media assemblies 150 at one or more positions within an internal sensor portion defined within the sensor housing 101 in order to facilitate execution of one or more functions of an exemplary sensor 100, such as, for example, a collection media generation function, a particle collection function, a particle analysis function, a sample incubation function, and/or the like. In various embodiments, an exemplary fluid composition sensor 100 may be configured to execute one or more operations and/or functions of the sensor in an at least substantially in situ configuration. For example, in various embodiments, an exemplary fluid composition sensor 100 may comprise a collection fluid dispense chamber 170 disposed within an internal sensor portion of the housing 101 of the fluid composition sensor 100.

Figure 10A:
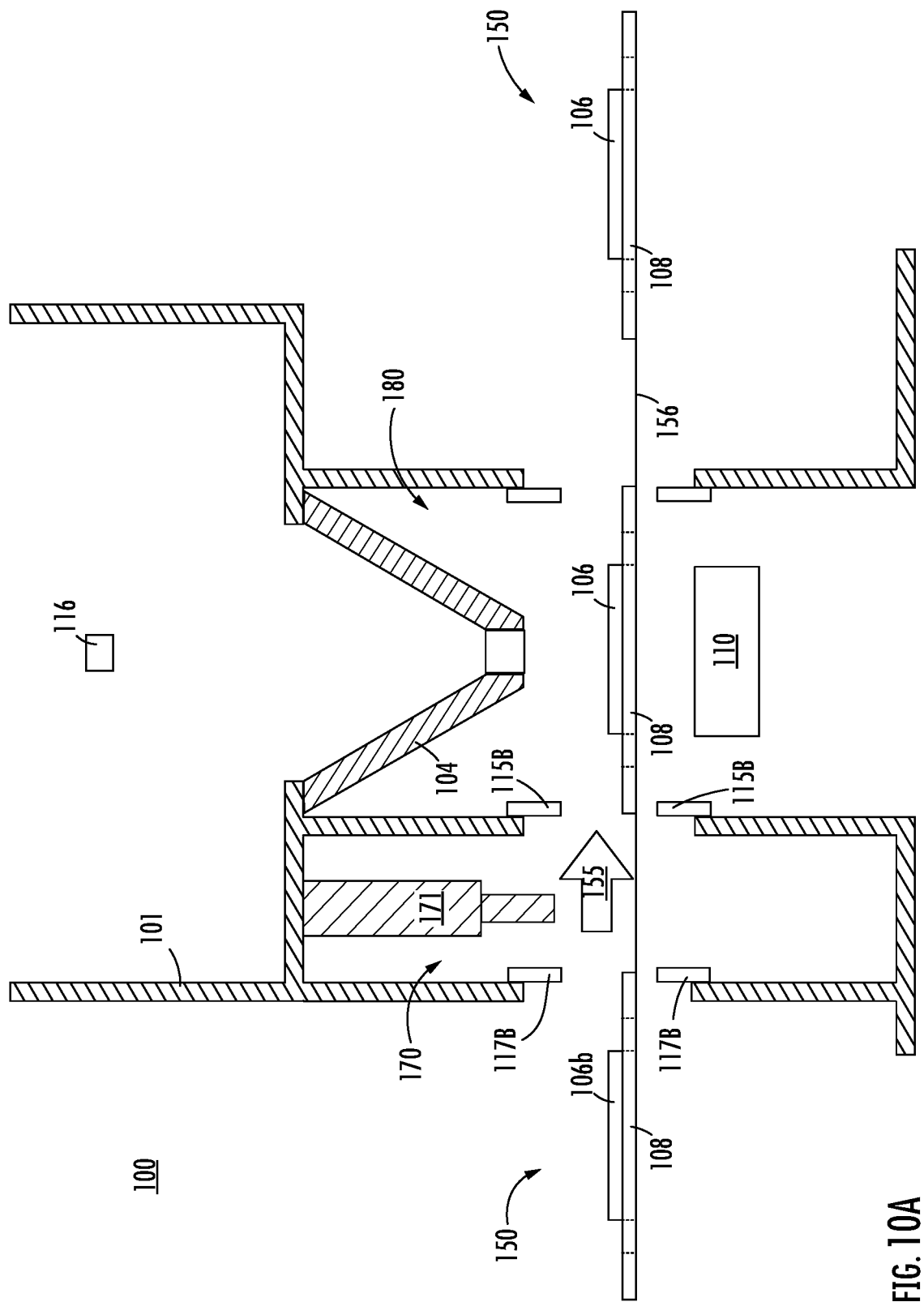
FIGS. 10A-10D illustrate a cross-sectional view of an exemplary apparatus in accordance with one embodiment described herein.

As illustrated in FIG. 10A, the fluid composition sensor 100 may comprise a collection fluid dispense assembly 171 arranged within a collection fluid dispense chamber 170. In various embodiments, as described in further detail herein, a collection fluid dispense assembly 171 may facilitate execution of at least a portion of a collection media generation function of the sensor 100 by being configured to store a volume of collection fluid, as described herein, and selectively dispense at least a portion of the stored collection fluid onto an unused absorbent media positioned in a collection fluid receiving position within the collection fluid dispense chamber 170. In various embodiments, a collection fluid dispense chamber 170 may be positioned within a fluid composition sensor 100 such that a collection fluid receiving position is defined as being operationally upstream relative to a particle collection position. For example, an exemplary fluid composition sensor 100 may be configured to position a collection media assembly 150 comprising an unused absorbent media 106*b* within the collection fluid dispense chamber 170 (e.g., at a collection fluid receiving position) prior to the collection media assembly 150 being arranged in a particle collection position (e.g., adjacent an impaction nozzle 104 outlet), such that the absorbent media 106*b* may first, in a collection fluid receiving position, receive a volume of collection fluid dispensed from the collection fluid dispense assembly 171, and subsequently, upon generation of a collection media 106 (e.g., via a combination of the dispensed volume of collection fluid and the absorbent media 106*b*) may be transported in a first direction 155 to the particle collection position such that the generated collection media 106 may receive one or more particles from a fluid sample dispensed from the impaction nozzle 104. Further, in various embodiments, a collection fluid dispense chamber 170 may be configured to receive one or more collection media assemblies 150 comprising an unused absorbent media 106*b* from a collection media assembly storage chamber 160, as described herein.

Further, in various embodiments, an exemplary fluid composition sensor 100 may be configured so as to define a particle engagement chamber 180 disposed within an internal sensor portion of the housing 101 of the fluid composition sensor 100. In various embodiments, an exemplary fluid composition sensor 100 may be configured to execute at least a portion of a particle collection functionality and/or a particle analysis functionality within a particle engagement chamber 180. For example, a particle collection position, as described herein, may be defined such that a collection media assembly 150 arranged in such a position comprises a collection media that positioned at least substantially entirely within the particle engagement chamber 180. In various embodiments, as described in further detail herein, a particle engagement chamber 180 may facilitate execution of at least a portion of a particle collection function and/or a particle analysis function of the sensor 100 by being configured to arrange a collection media assembly 150 (e.g., a collection media 106) within the chamber 180 at least substantially adjacent an impactor nozzle 104 outlet and further, by being configurable as a fluidly isolated chamber such that at least substantially all of the volume of fluid that passes through the impactor nozzle 104 outlet is passed over a collection media 106 therein without being diluted and/or diverted by an ambient environment. In various embodiments, a particle engagement chamber 180 may be positioned within a fluid composition sensor 100 such that a particle collection position is defined as being operationally downstream relative to a collection fluid receiving position. For example, an exemplary fluid composition sensor 100 may be configured to position a collection media assembly 150 comprising a unused collection media 106 within the particle engagement chamber 180 (e.g., at a particle collection position) subsequent to the collection media assembly 150 being arranged in a collection fluid receiving position (e.g., within the collection fluid dispense chamber 170), such that the collection media assembly arranged within the particle engagement chamber 180 may comprise a collection media 106 generated via a combination of the dispensed volume of collection fluid and the absorbent media 106*b*. For example, the particle engagement chamber 180 may be configured to receive a collection media assembly 150 that is transported from a collection fluid dispense chamber 170 in a first direction 155.

As described herein, in various embodiments, a fluid composition sensor may be configurable between an open housing configuration and a closed configuration. In particular, FIG. 10A illustrates a cross-sectional view of an exemplary fluid composition sensor 100 in an open configuration, wherein the exemplary fluid composition sensor 100 is configured to receive a plurality of collection media assemblies 150 disposed upon a length of alignment tape 156. For example, in various embodiments, the plurality of collection media assemblies 150 disposed upon the alignment tape 156 may be arranged so as to define a row of absorbent media 106*b* configured to receive respective volumes of collection fluid in series (e.g., sequentially) from a collection fluid dispense assembly 171 as the absorbent media 106*b* each pass through the collection fluid receiving position within the collection fluid dispense chamber 170. As described herein, the fluid composition sensor 100 may be configured such that when the fluid composition sensor 100 is in the open configuration, the alignment tape may be moveable about a transverse plane in a plurality of directions (e.g., in the first direction 155) such that the plurality of collection media assemblies 150—each comprising either an unused absorbent media 106*b* or a collection media 106 formed by the combination of an absorbent media portion and a collection fluid portion—disposed thereon may move relative to one or more internal sensor portions within the housing 101. The alignment tape 156 may be configured such that one or more absorbent media 106*b* disposed thereon may be moved (e.g., linearly shifted and/or rotated) relative to the housing 101 such that a fresh (e.g., unused) absorbent media 106*b* of the plurality of collection media assemblies 150 may be exposed to a volume of collection fluid dispensed from the collection fluid dispense assembly 171. Further, in various embodiments, the alignment tape 156 may be configured such that the plurality of collection media 106 may be moved (e.g., linearly shifted and/or rotated) relative to the housing 101 such that a fresh (e.g., unused) collection media 106 of the plurality of collection media assemblies 150 may be exposed to a volume of fluid flowing through an impactor nozzle 104. As described herein, upon the arrangement of an unused absorbent media 106*b* in a desired position at least substantially adjacent a collection fluid dispense nozzle of the collection fluid dispense assembly 171 (e.g., at a collection fluid receiving position) and/or the arrangement of an unused collection media 106 in a desired position at least substantially adjacent the nozzle outlet of the impactor nozzle 104 (e.g., at a particle collection position), the fluid composition sensor 100 may be reconfigured from an open configuration, as illustrated in FIG. 10A, to a closed configuration, as described in further detail herein, thereby securing the position of one or more collection media assemblies 150 relative to a collection fluid dispense assembly 171, an imaging device 110, and/or impactor nozzle 104 outlet.

Figure 10B:
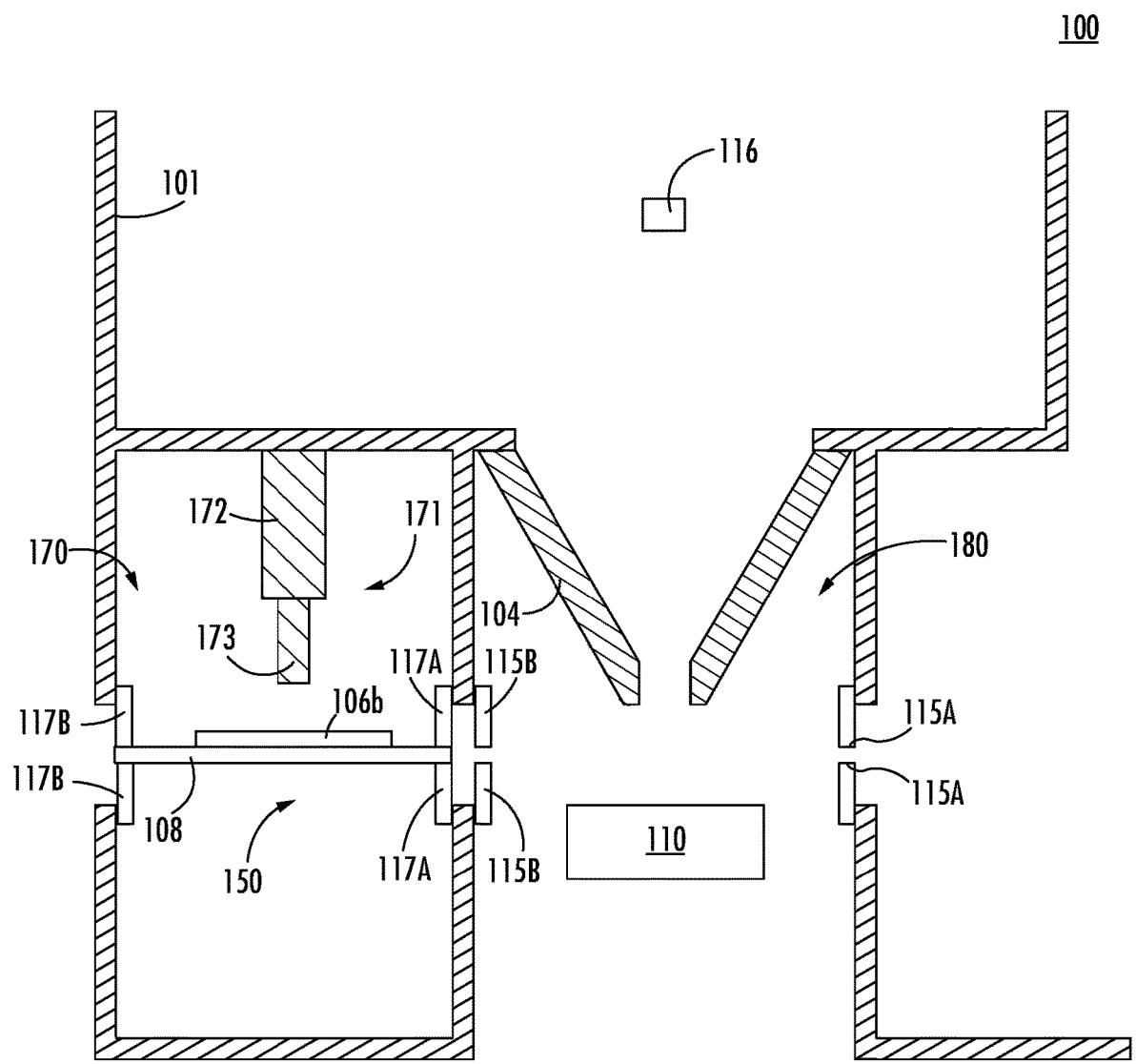

FIG. 10B illustrates a cross-sectional view of an exemplary fluid composition sensor in a closed configuration. In various embodiments, a fluid composition sensor 100 in a closed configuration may be defined at least in part by the engagement of one or more air seal components with a corresponding sensor component, such as, for example, an air seal component, an air seal engagement portion of a collection media assembly, an adjacent interior surface of the sensor housing 101, and/or the like, in order to define a fluidly isolated chamber within at least a portion of the internal sensor portion and, further, to secure the position of the one or more collection media assemblies 150 within the fluid composition sensor 100. As illustrated, the exemplary fluid composition sensor 100 is in a closed configuration with a collection media assembly 150 comprising a fresh (e.g., unused) absorbent media 106*b* secured in a collection fluid receiving position within a collection fluid dispense chamber 170. In various embodiments, the collection fluid dispense chamber 170 of the fluid composition sensor 100 may comprise one or more air seal components 117A, 117B configured to engage one or more corresponding air seal engagement components 117A, 117B disposed at least substantially adjacent one or more openings within the collection fluid dispense chamber 170 and/or a corresponding air seal engagement portions defined along the transparent substrate 108. As described herein, the one or more air seal components 117A, 117B may be configured to generate an at least substantially air-tight seal that surrounds at least the absorbent media 106*b* so as to fluidly isolate the absorbent media 106*b* from an ambient environment and/or to prevent a portion of a volume of collection fluid dispensed from the collection fluid dispense assembly 171 from escaping the collection fluid dispense chamber 170.

In various embodiments, a fluid composition sensor 100 may comprise a collection fluid dispense assembly 171 disposed within a collection fluid dispense chamber 170. For example, in various embodiments, a collection fluid dispense assembly 171 may be positioned within a collection fluid dispense chamber 170 such that such that one or more volumes of collection fluid may be dispensed from the collection fluid dispense assembly 171 onto an absorbent media 106*b* of an exemplary collection media assembly 150 arranged in a collection fluid receiving position, as described herein. In various embodiments, the collection fluid dispense assembly 171 is configured to enable a collection media generation functionality of a fluid composition sensor 100 to be executed via an at least substantially on-demand operation. An exemplary the collection fluid dispense assembly 171 is configured to facilitate the on-demand application of a volume of collection fluid onto an absorbent media 106*b* such that a collection media 106 configured to receive a plurality of particles from within a fluid sample may be produced within an interior sensor portion of a fluid composition sensor 100 in real-time, thereby minimizing the leadup time and resultant inefficiencies associated with remotely manufactured collection media. As described herein, the collection fluid dispense assembly 171 is configured to enable a substantially automated and/or serial production of a plurality of collection media in real-time so as to facilitate the automation of one or more of the exemplary fluid composition sensor's 100 particle collection, particle incubation, and/or particle analysis functionalities.

In various embodiments, an exemplary collection fluid dispense assembly 171 may comprise one or more collection fluid cartridges 172 configured to store one or more volumes of collection fluid therein. For example, in various embodiments, the one or more collection fluid cartridges 172 may comprise a plurality of collection fluid cartridges, each of which may be configured to store a respective volume of a collection fluid therein. In such an exemplary circumstance, a first collection fluid cartridge of the plurality of collection fluid cartridges may be configured to store therein a volume of a first collection fluid that is at least substantially different from a second collection fluid that is stored in a second collection fluid cartridge of the plurality. As a non-limiting example, in various embodiments, the one or more collection fluid cartridges 172 may be configured to store one or more volumes of Triacetin. In various embodiments, a collection fluid cartridge 172 of an exemplary collection fluid dispense assembly 171 may be defined at least in part by a collection fluid cartridge volume of at least substantially between 0.1 mL and 1000 mL (e.g., between 1.0 mL and 100 mL). As described herein, the collection fluid dispense assembly 171 may be configured to facilitate the dispense of one or more volumes of collection fluid from one or more collection fluid cartridges 172 onto an absorbent media 106b so as to produce a resultant collection media 106 having one or more pre-determined collection media characteristics, such as, for example, collection media volume, collection media color, fluorescence, and/or transparency, collection media density, collection media viscosity, and/or the like, or any combination thereof.

In various embodiments, a collection fluid dispense assembly 171 may further comprise one or more dispense headers 173 fluidly connected to a respective collection fluid cartridge 172. As described herein, the one or more dispense headers 173 may be configured to facilitate execution of at least a portion of a collection fluid generation functionality of an exemplary fluid composition sensor 100 by directing a flow of a volume of collection fluid dispensed from a collection fluid cartridge 172 in a dispense direction extending into the collection fluid dispense chamber 170 and at least substantially toward a receiving face of an absorbent media 106b arranged in a collection fluid receiving position. As described herein, an unused absorbent media 106b may be present in the collection fluid dispense chamber 170 (e.g., at a collection fluid receiving position) prior to the one or more volumes of collection fluid being dispensed. In such an exemplary circumstance, a volume of collection fluid dispensed from a collection fluid cartridge 172 via a respective dispense header 173 fluidly connected thereto may be received at the absorbent media 106b and at least substantially retained within an internal volume of the absorbent media 106b so as to facilitate an interaction between the absorbent media 106b and the volume of collection fluid. In various embodiments, a dispense header 173 of an exemplary collection fluid dispense assembly 171 may be configured to dispense a volume of collection fluid at a dispense flow rate such that a flow comprising at least substantially all of the volume of collection fluid dispensed from a collection fluid cartridge travels in a dispense direction to the absorbent media.

In further embodiments, a volume of collection fluid may be dispensed from a dispense header 173 and into a delivery conduit configured to receive the volume of collection fluid from the cartridge 172 and deliver the dispensed collection fluid to an absorbent media 106b. In certain embodiments, a delivery conduit may be fluidly connected to a collection fluid retention funnel or any other suitable collection mechanism configured to capture at least a portion of each of the one or more dispensed volumes of collection fluid and direct them toward an absorbent media 106b arranged in a collection fluid receiving position.

As described herein, an exemplary collection fluid dispensed from a collection fluid dispense assembly 171 may comprise a fluid configured to facilitate and/or initiate one or more reactions (e.g., a chemical reaction, a physical reaction, and/or the like, or any combination thereof) between the fluid and the absorbent media 106b upon engaging the absorbent media 106b. In such an exemplary circumstance, the one or more reactions between the dispensed volume of collection fluid and the absorbent media 106b configured to receive the same may produce a resultant collection media 106, which may comprise, by way of non-limiting illustrative example, a gel, an at least partially adhesive substance, and/or the like, that is configured to receive one or more particles present within a fluid sample upon the sample passing over (e.g., physically engaging) the resultant collection media 106. In various embodiments, the collection fluid dispense assembly 171 may be configured to generate a resultant collection media 106 comprising an absorbent media portion and a collection fluid portion. Further, in various embodiments, based at least in part on an initial configuration of an absorbent media 106b relative to the transparent substrate 108, the collection fluid dispense assembly 171 may be configured to generate a resultant collection media 106 that is disposed upon the transparent substrate 108 of a collection media assembly 150 so as to facilitate at least a portion of one or more downstream operations corresponding to a particle collection functionality and/or a particle imaging (e.g., particle analysis) functionality of an exemplary fluid composition sensor 100, as described herein.

Figure 10C:
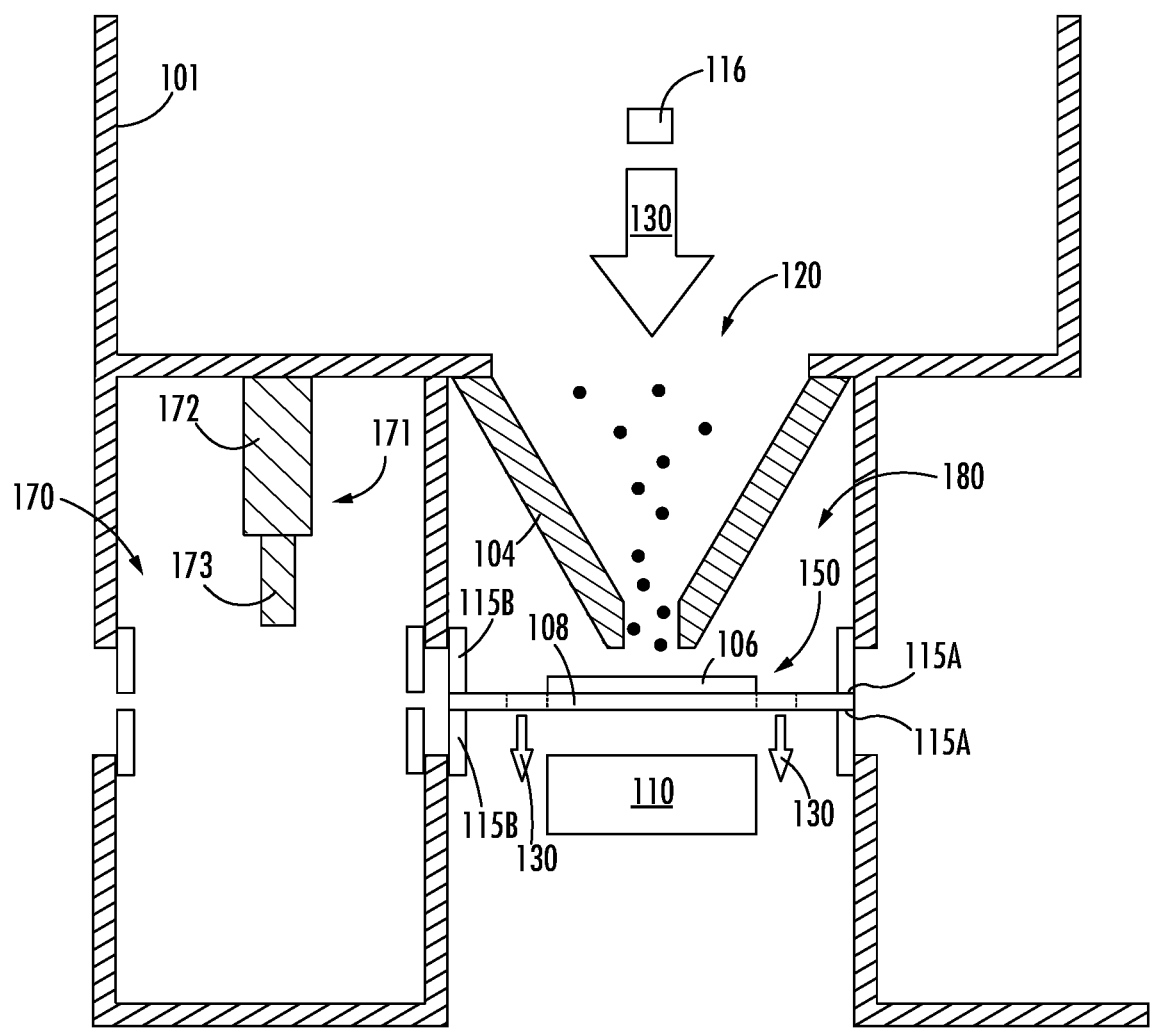

FIG. 10C illustrates a cross-sectional view of an exemplary fluid composition sensor in a closed configuration. As illustrated, the exemplary fluid composition sensor 100 is in a closed configuration with a collection media assembly 150 comprising a collection media 106 secured in a particle collection position within a particle engagement chamber 180. In various embodiments, the particle engagement chamber 180 of the fluid composition sensor 100 may comprise one or more air seal components 115A, 115B configured to engage one or more corresponding air seal engagement components 115A, 115B disposed at least substantially adjacent one or more openings within particle engagement chamber 180 and/or a corresponding air seal engagement portions defined along the transparent substrate 108. As described herein, the one or more air seal components 115A, 115B may be configured to generate an at least substantially air-tight seal that surrounds at least the collection media 106 so as to fluidly isolate the collection media 106 from an ambient environment and/or to prevent a portion of a fluid sample provided into a particle engagement chamber 180 from an impactor nozzle 104 outlet from escaping the particle engagement chamber 180.

In various embodiments, as described herein, the impactor nozzle 104 may be disposed within the internal sensor portion of the housing 101 and may comprise a nozzle inlet configured to receive at least a portion of the volume of fluid received by the fluid composition sensor, a nozzle outlet, and a plurality of sidewalls extending between the nozzle inlet and the nozzle outlet. Each of the plurality of sidewalls of the impactor nozzle may comprise an inner sidewall and an outer sidewall. In various embodiments, the nozzle inlet may comprise a nozzle inlet cross-sectional area defined at least in part by a perimeter formed by each of the inner sidewalls of the plurality of sidewalls at the nozzle inlet. Similarly, the nozzle outlet may comprise a nozzle outlet cross-sectional area defined at least in part by a perimeter formed by each of the inner sidewalls of the plurality of sidewalls at the nozzle outlet. In various embodiments, the impactor nozzle 104 may further comprise a central nozzle axis extending perpendicularly between the nozzle inlet and the nozzle outlet.

As described, the impactor nozzle 104 may receive at least a portion of the volume of fluid received by the fluid composition sensor 100 and may be configured so as to direct the volume of fluid in a flow direction 130 at least substantially perpendicular to and directed toward a receiving surface of a collection media 106. For example, flow direction 130 may be at least substantially aligned and/or parallel with the central nozzle axis of the impactor nozzle 104. The collection media 106 may be disposed about a transparent substrate 108 and configured to receive one or more particles of a plurality of particles 120 within the volume of fluid via interaction with the volume of fluid directed from the impactor nozzle 104. In various embodiments, as described herein, the collection media 106 disposed on the substrate 108 may embody a resultant collection media that was generated as the product of a collection media generation operation executed by the fluid composition sensor 100 (e.g., the collection fluid dispense assembly 171), wherein a volume of a collection fluid is dispensed from a collection fluid dispense assembly 171 onto a fresh absorbent media 106b disposed about the transparent substrate 108, thereby causing a reaction between the absorbent media 106b and the dispensed collection fluid received therein that results in a resultant collection media (e.g., collection media 106) being generated on the substrate 108. For example, in various embodiments, a particle engagement chamber 180 may be positioned within a fluid composition sensor 100 such that a particle collection position is defined as being operationally downstream relative to the collection fluid dispense assembly 171 and/or a corresponding collection fluid receiving position. As such, in various embodiments, the particle engagement chamber 180 may receive the collection media assembly 150 comprising a resultant collection media 106 from the collection fluid dispense chamber 170, within which at least a portion of the collection media generation operations were previously executed. As described herein, the collection media 106 may be a component of a collection media assembly, which may further comprise a transparent substrate 108. As described herein, a collection media assembly 150 may be configured such that at least a portion of the volume of fluid traveling along a fluid flow path 130 may pass through a transparent substrate 108 via one or more orifices extending therethrough so as to continue through the internal sensor portion in flow direction 130.

As described, the fluid composition sensor 100 may comprise an illumination source 116 configured to emit one or more light beams. In various embodiments, the illumination source 116 may be a laser, lamp, light-emitting diode (LED), and/or the like, which may operate in connection with one or more lenses collectively configured to generate a light beam (e.g., ultraviolet, visible, infrared, or multiple color light) that may be emitted toward the collection media 106, as described herein in further detail. In some embodiments, the illumination source 116 may be configured such that a lens is not required, such as, for example, when the fluid composition sensor is configured to execute lensless holography, as described herein. For example, as illustrated in FIG. 10C, the illumination source may be configured to emit the one or more light beams in a light emission direction 130, such that the light beams may engage the collection media 106 and illuminate the one or more particles disposed within the collection media 106. Further, as described herein, the fluid composition sensor may further comprise an imaging device 110 configured to capture an image of the one or more particles of the plurality of particles 120 received by the collection media 106. In various embodiments, the imaging device 110 may be positioned at least substantially adjacent (e.g., in contact with or spaced a distance away from) the transparent substrate 108 such that the imaging device 110 may effectively capture one or more images of the one or particles captured within the collection media 106. The collection media 106 may reside at least partially within the field of view of the imaging device 110, such that the plurality of particles 120 captured by the collection media 106 are visible by the imaging device 110. In various embodiments, the imaging device 110 may be configured to capture the image of one or more particles of the plurality of particles 120 received by the collection media 106 using one or more imaging techniques such as, for example, lensless holography, optical microscopy, and/or the like.

Figure 10D:
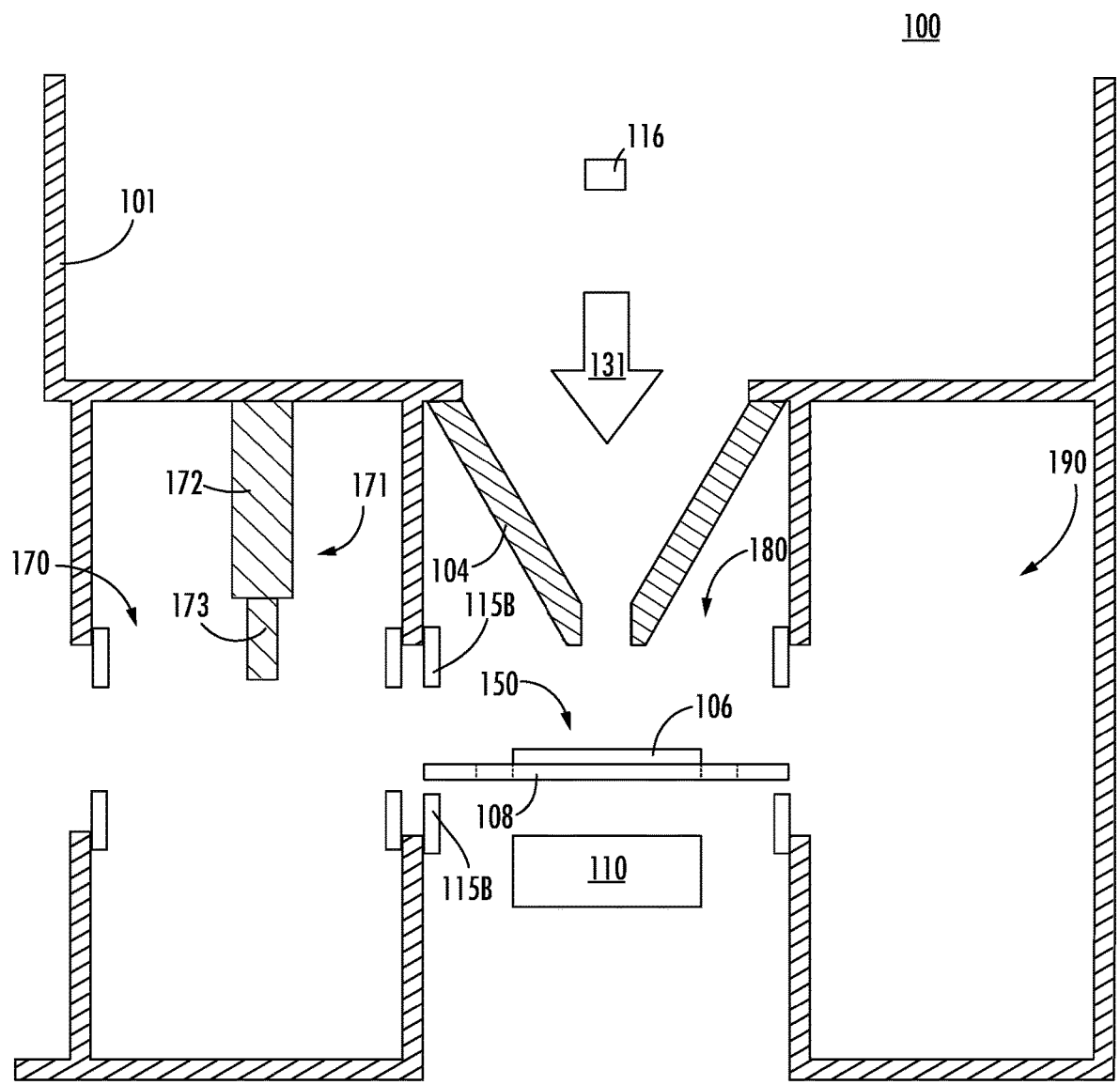

FIG. 10D illustrates a cross-sectional view of an exemplary fluid composition sensor in an open configuration. In various embodiments, a fluid composition sensor in an open housing configuration may be configured so as to allow for the reconfiguration of a collection media assembly relative to at least a portion of the internal sensor portion of the housing 101 (e.g., a collection media dispense chamber 170, a particle engagement chamber 180, and/or the like). In various embodiments wherein the fluid composition sensor 100 is in an open configuration, one or more collection media assemblies 150 comprising a collection media 106 disposed within the internal sensor portion of the fluid composition sensor 100 may be reconfigured such that the collection media 106 is removed from the internal sensor portion. For example, the one or more collection media assembly 150 may be removed from the internal sensor portion and transported to an exemplary secondary location. Further, in various embodiments wherein the fluid composition sensor 100 is in an open configuration, the one or more collection media assemblies 150 (e.g., the corresponding resultant collection media 106 thereof) disposed within the internal sensor portion of the fluid composition sensor 100 may be reconfigured such that the collection media 106 may be removed from a first position within the internal sensor portion and transported to a second position within the internal sensor portion. For example, the collection media assembly 150 may be removed from a collection fluid receiving position within a collection fluid dispense chamber 170 and transported to a particle collection position within a particle engagement chamber 180. As a further non-limiting example, a collection media assembly 150 may be removed from a particle collection position within a particle engagement chamber 180 and transported in a first direction to a particle incubation position within an incubation chamber 190, as described herein. Conversely, as a further non-limiting example described in further detail herein, in various embodiments, wherein the fluid composition sensor 100 is in an open configuration, a collection media assembly 150 may be removed from a particle incubation position within an incubation chamber 190 and transported in a second direction that is at least substantially opposite from the aforementioned first direction back to the particle collection position within the particle engagement chamber 180.

Additionally, wherein the fluid composition sensor is in an open configuration, a collection media assembly comprising a collection media 106 positioned outside of the housing 101 may be reconfigured such that the collection media 106 is deposited into the internal sensor portion of the housing 101. For example, a collection media assembly 150 comprising one or more fresh absorbent media 106b may be rotated and/or shifted relative to an internal sensor portion (e.g., a collection media dispense chamber 170) such that the absorbent media 106b is arranged at a collection fluid receiving position at least substantially adjacent the collection fluid dispense assembly 171. Although illustrated with respect to various exemplary embodiments described herein as comprising a physical opening such that one or more components of the fluid composition sensor disposed within the internal sensor portion of the housing may be exposed to a volume of ambient fluid, it should be understood that, in various embodiments, the internal sensor portion of the fluid composition sensor may remain at least substantially isolated from the ambient environment in an open configuration in order to avoid sensor contamination.

Figure 11:
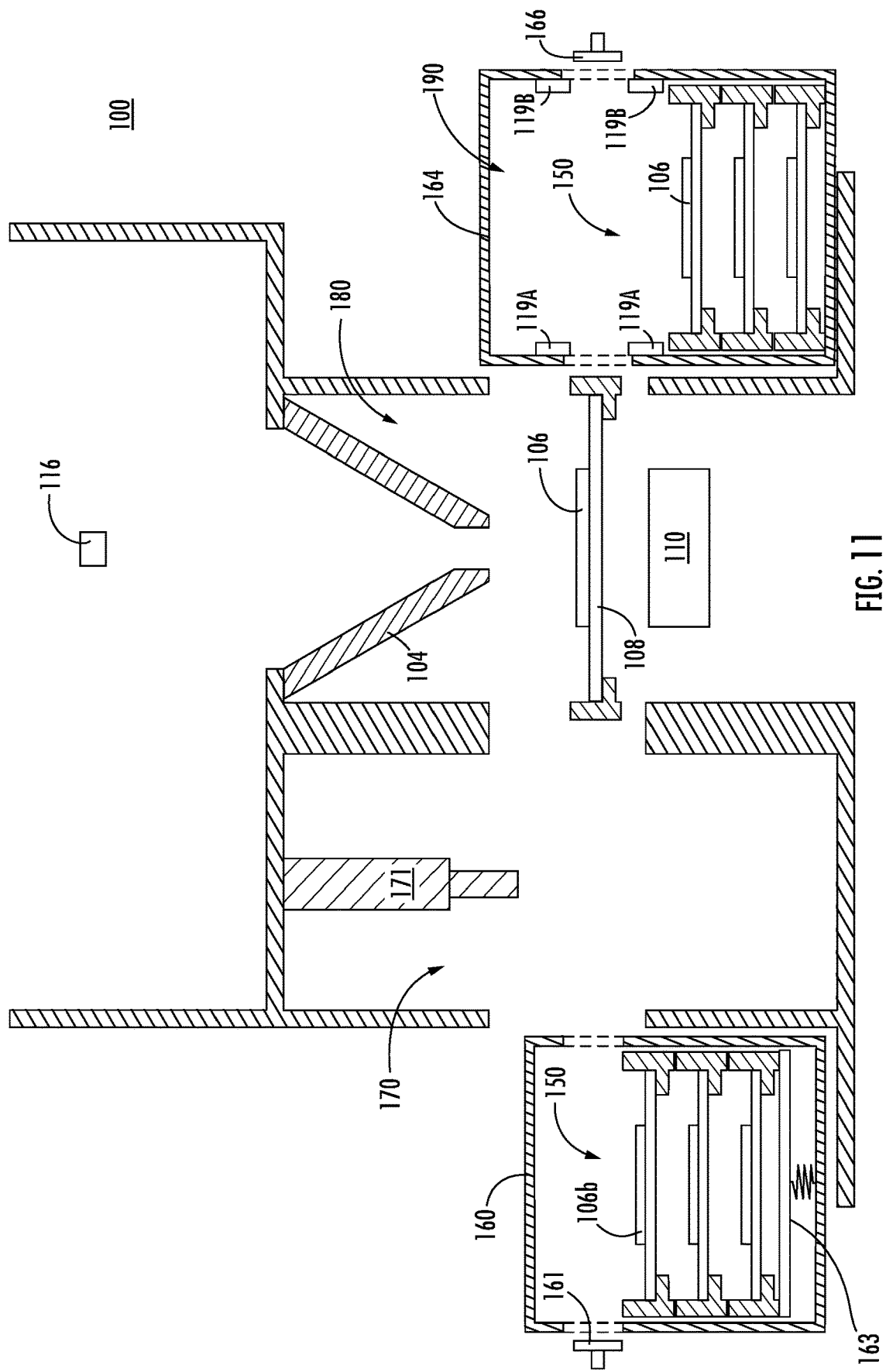
FIG. 11 illustrates a cross-sectional view of an exemplary apparatus in accordance with one embodiment described herein.
Figure 12:
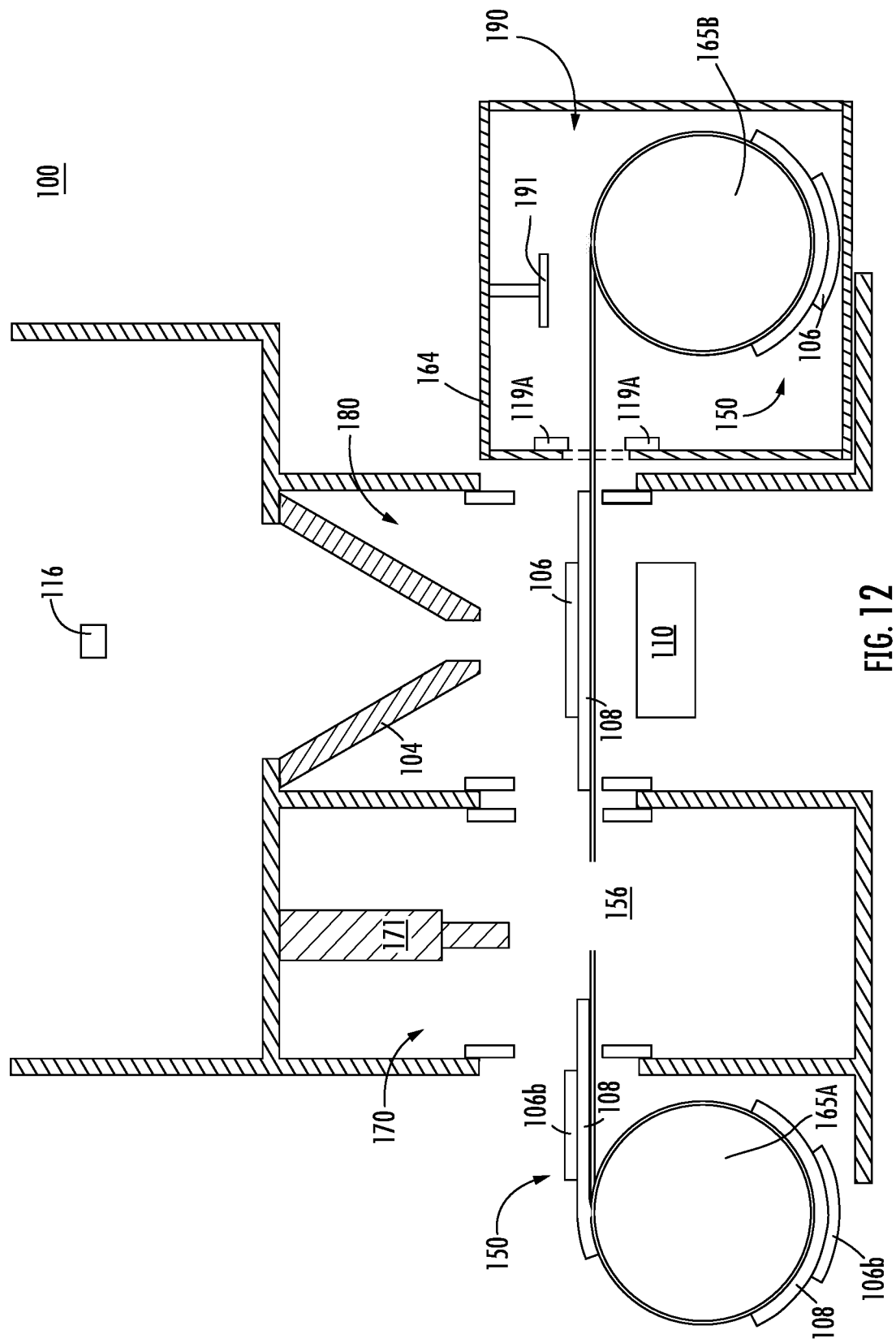
FIG. 12 illustrates a cross-sectional view of an exemplary apparatus in accordance with one embodiment described herein.
Figure 13:
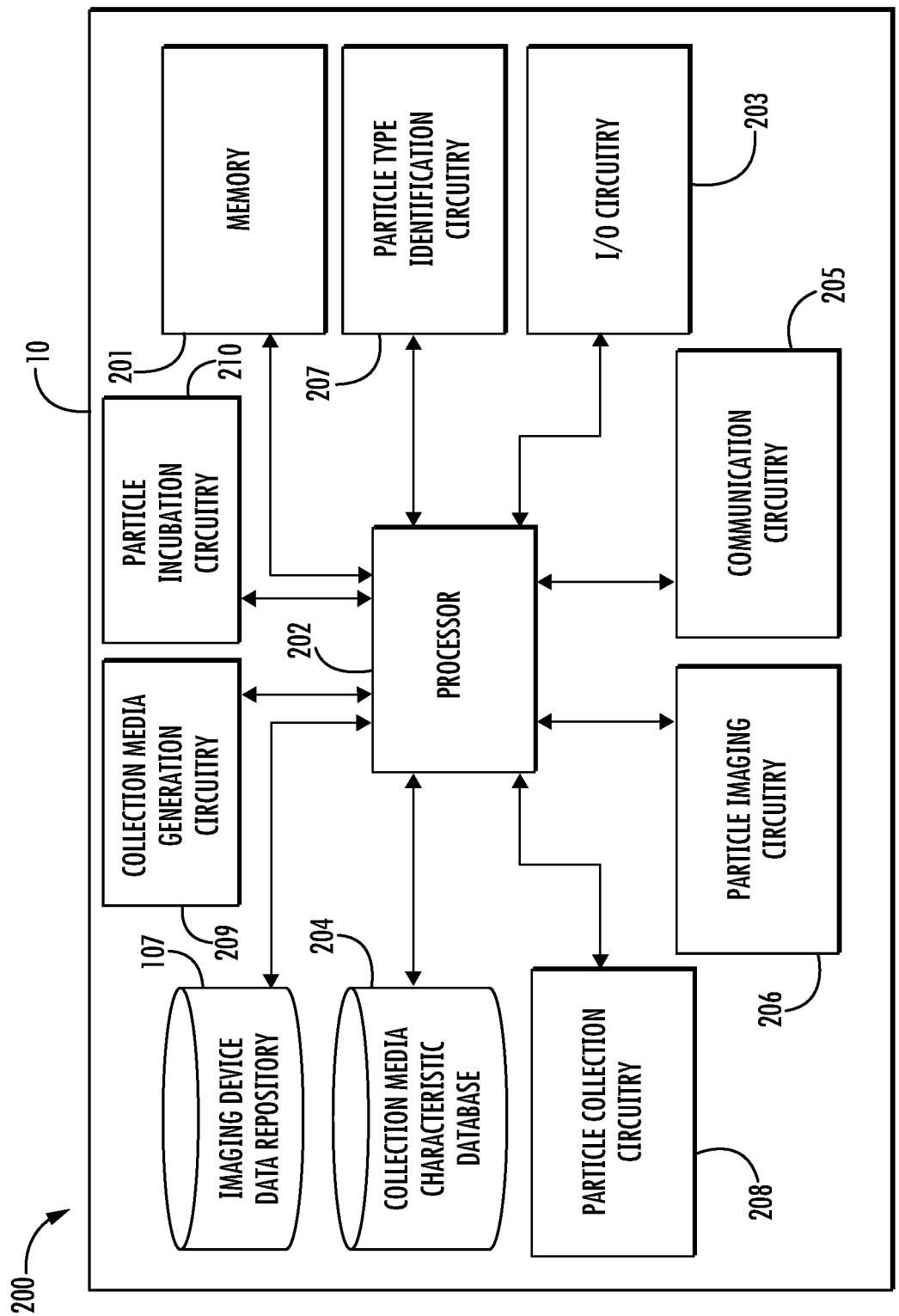
FIG. 13 schematically illustrates an exemplary apparatus for implementing various embodiments of the present disclosure.

FIGS. 11 and 12 illustrate various cross-sectional views of exemplary apparatuses in accordance with embodiments described herein. FIG. 11 illustrates a cross-sectional view of an exemplary fluid composition sensor in an open configuration, wherein the exemplary fluid composition sensor comprises a plurality of independently moveable collection media assemblies 150 each being configured to be consecutively disposed within the internal sensor portion of the fluid composition sensor in series. In various embodiments, the fluid composition sensor 100 may comprise one or more collection media assembly storage chambers configured to store at least a portion of the plurality of collection media assemblies 150. Further, in various embodiments, each of the at least one collection media assembly storage chambers may be configured to dispense into and/or receive from the housing 101 one or more of the plurality of collection media assemblies 150. For example, as illustrated, the fluid composition sensor may comprise a first collection media assembly storage chamber 160 and a second collection media assembly storage chamber 164. In various embodiments, as described in further detail herein, the second collection media assembly storage chamber 164 of an exemplary fluid composition sensor 100 may embody an incubation chamber 190 configured to receive one or more collection media assemblies 150 from within a particle engagement chamber 180 that have previously been used to facilitate execution of a particle collection operation, such that the collection media assemblies 150 received by the incubation chamber 190 comprises a plurality of particles from a fluid sample disposed within the collection media 106 thereof.

As illustrated in FIG. 11, the exemplary plurality of collection media assemblies 150 may each comprise a collection media and/or an absorbent media disposed upon a transparent substrate and a collection media housing (e.g., a frame element). As described herein, in various embodiments, each of a plurality of collection media assemblies 150 may be configured so as to facilitate the collective storage thereof in a collection media assembly storage chamber. For example, as illustrated, at least a portion of the plurality of the collection media assemblies 150 may be organized in a stacked configuration the corresponding collection media housings may be stacked relative to one another so as to minimize unwarranted contamination of a collection media through physical engagement of the collection media with one or more components of an adjacent collection media assembly (e.g., a corresponding collection media housing).

In various embodiments, the first collection media assembly storage chamber 160 may store a plurality of unused collection media assemblies prior to the plurality of collection media assemblies being respectively used for particle collection within a fluid composition sensor. For example, the first collection media assembly storage chamber 160 may store a plurality of collection media assemblies 150 comprising a fresh (e.g., unused) absorbent media 106b prior to the plurality of collection media assemblies 150 each receiving at the respective absorbent media 106b a volume of collection fluid dispensed from the collection fluid dispense assembly 171 so as to generate a resultant collection media 106 configured to receive one or more particles from within a fluid sample. Further, for example, the first collection media assembly storage chamber 160 may store a plurality of unused collection media assemblies 150 comprising fresh (e.g., unused) absorbent media 106b prior being positioned within a particle collection position and used for particle collection within the particle engagement chamber 180 of the fluid composition sensor 100. For example, the first collection media assembly storage chamber 160 may be configured to arrange within the chamber 160 the plurality of collection media assemblies 150 such that they may be consecutively transmitted in series from the first collection media assembly storage chamber 160 to an internal sensor portion, such as, for example, a collection fluid dispense chamber 170, of the fluid composition sensor 100. In various embodiments, the collection media assembly storage chamber 160 may comprise an actuator element 161 configured to selectively apply a force to one of the plurality of collection media assemblies 150 stored within the first collection media assembly storage chamber 160 (e.g., in a loading position) so as to reposition the collection media assembly 150 from the collection media assembly storage chamber 160 towards an internal sensor portion of the housing 101 of the fluid composition sensor 100 (e.g., into a collection fluid receiving position, a particle collection position, a particle incubation position, and/or the like. For example, in the exemplary embodiment illustrated in FIG. 11, the actuator element 161 of the first collection media assembly storage chamber 160 may be configured to apply a transverse force to a collection media assembly 150 positioned in a loading position (e.g., at an uppermost position in a stack of collection media assemblies) so as to dispense the collection media assembly 150 from the first collection media assembly storage chamber 160 and into one or more positions within the exemplary fluid composition sensor 100, as described herein.

In various embodiments, the fluid composition sensor 100 may comprise a second collection media assembly storage chamber 164 configured to store a plurality of used collection media assemblies 150 (e.g., a collection media assembly 150 comprising a collection media 106 that has been disposed within the internal sensor portion and comprising a surface that has been passed over by at least one volume of fluid such that one or more particles from the volume of fluid are disposed therein) dispensed from the fluid composition sensor housing 101. For example, the second collection media assembly storage chamber 164 may be configured to receive the plurality of collection assemblies 150 consecutively transmitted in series from the internal sensor portion of the fluid composition sensor 100 to the second collection media assembly storage chamber 164.

The second collection media assembly storage chamber 164 may comprise a deposit opening within one or more walls of the chamber, the deposit opening being configured to allow one or more of the collection media assemblies 150 transported from within a particle engagement chamber 180 to pass therethrough such that the one or more collection media assemblies 150 may be dispensed into to the second collection media assembly storage chamber 164. As a non-limiting example, a collection media assembly 150 may be removed from a particle collection position within a particle engagement chamber 180 and transported in a first direction toward the deposit opening of the second collection media assembly storage chamber 164. In various embodiments, the deposit opening may comprise a deposit door that may be selectively opened and closed to facilitate the selective receipt of a collection media assembly 150. For example, in various embodiments, the second collection media assembly storage chamber 164 may comprise one or more air seal components 119A, 119B configured to engage one or more corresponding air seal engagement components 119A, 119B disposed at least substantially adjacent one or more openings (e.g., a deposit opening, an actuator opening, and/or the like) within the second collection media assembly storage chamber 164 and/or an adjacent wall of the second collection media assembly storage chamber housing. As described herein, the one or more air seal components 119A, 119B may be configured to generate an at least substantially air-tight seal about the entirety of the collection media assembly storage chamber 164 exterior so as to fluidly isolate the interior volume within the collection media assembly storage chamber 164 from an ambient environment. For example, as described herein, in various embodiments wherein the collection media assembly storage chamber 164 comprises an incubation chamber, the fluidly isolated interior volume within the collection media assembly storage chamber 164 may define a local incubation environment defined at least in part by one or more local conditions within an the incubation chamber, such as, for example, a chamber temperature, chamber humidity, chamber pressure, chamber light wavelength spectrum, chamber illumination frequency, chamber gas content, and/or the like.

As described herein, upon determining that at least substantially the entirety of a sample volume of fluid has passed across a surface of a collection media 106, the fluid composition sensor 100 may be configured to dispense the used collection media 106 and repopulate the particle collection position within the particle engagement chamber 180 with an unused collection media 106. In various embodiments, the fluid composition sensor 100 may be configured to dispense the used collection media 106 from the particle collection position within the particle engagement chamber 180 and to the second collection media assembly storage chamber 164. In various embodiments, the particle engagement chamber 180 within the fluid composition sensor 100 may be configured to receive a collection media assembly 150 comprising an unused collection media 106 from a collection fluid dispense chamber 170, the unused collection media 106 having been generated via a collection media generation operation executed by the collection fluid dispense assembly 171, as described herein. In such an exemplary circumstance, the collection fluid dispense chamber 170 within the fluid composition sensor 100 may be configured to receive a collection media assembly 150 comprising an unused absorbent media 106b from the first collection media assembly storage chamber 160. In various embodiments, the fluid composition sensor 100 may be configured to execute a transmission of a used collection media 106 to the second collection media assembly storage chamber 164, a transmission of an unused collection media 106 from the collection fluid receiving position to the particle collection position, and/or a transmission of an unused absorbent media 106b from a first collection media assembly storage chamber 160 to the collection fluid receiving position, at either a substantially similar time (e.g., simultaneously) or a different time (e.g., in sequence) via one or more automated operations.

In various embodiments, an exemplary fluid composition sensor 100 may comprise an incubation chamber configured to receive one or more collection media assemblies therein and facilitate execution of one or more incubation operations so as to culture one or more particles disposed at a collection media of a collection media assembly arranged within the chamber. For example, in various embodiments, an exemplary incubation chamber 190 may be defined at least in part by an internal chamber volume configured to receive one or more used collection media assemblies 150 (e.g., a collection media assembly 150 comprising a collection media 106 that has been disposed within the internal sensor portion at a particle collection position and comprises a surface that has been passed over by at least one volume of fluid such that one or more particles from the volume of fluid may be disposed therein) therein. In various embodiments, an exemplary fluid composition sensor 100 may be configured such that one or more collection media assemblies 150 may be transported to an incubation chamber 190 and disposed within the internal chamber volume thereof upon being dispensed from within a particle engagement chamber 180. For example, as shown in the non-limiting example illustrated in FIG. 11, a second collection media assembly storage chamber 164 may embody the incubation chamber 190 of an exemplary fluid composition sensor 100. In various embodiments, an exemplary incubation chamber may be arranged within an internal sensor portion of an exemplary fluid composition sensor 100, or, alternatively, may be defined by an external chamber positioned remotely relative to the internal sensor portion.

In various embodiments, an exemplary fluid composition sensor 100 may be configured to execute an incubation run within an incubation chamber 190 in order to facilitate a biological growth of one or more particles (e.g., received from within a fluid sample) disposed within a collection media 106. For example, an incubation run carried out within an incubation chamber 190 may include selectively configuring, controlling, and/or maintaining one or more controlled local conditions within the incubation chamber 190, such as, for example, an incubation temperature, incubation humidity, incubation pressure, incubation light wavelength spectrum, an incubation illumination frequency, an incubation local gas composition (e.g., defined at least in part by one or more concentrations of gas present within an internal chamber volume), and/or the like, or any combination thereof. In various environments, a particle incubation configuration of an exemplary incubation chamber 190 during the execution of one or more incubation operations therein (e.g., incubation runs) may be defined at least in part by the one or more controlled incubation environment conditions exhibited within the incubation chamber 190 during an incubation run. In various embodiments, the particle incubation configuration of an incubation environment during an exemplary incubation run may be configured to sufficiently culture at least a portion of the particles embedded in a collection media 106 within the incubation chamber 190, so as to facilitate the biological growth of one or more of the particles within the collection media 106 and enable the detection, identification, and/or characterization of one or more colony-forming units (CFUs) present within the collection media 106. In various embodiments, an amount and/or rate of physical and/or biological growth exhibited by a particle disposed within a collection media 106 and subjected to an incubation environment (e.g., within incubation chamber 190) throughout an incubation run may be based at least in part on a particle incubation configuration and/or one or more particle characteristics, such as, for example, a particle type, a particle viability, and/or the like.

In various embodiments, for example, an exemplary fluid composition sensor 100 may be configured maintain an incubation temperature within the incubation chamber 190 (e.g., the incubation environment) of at least substantially between 1° C. and 50° C. (e.g., between 20° C. and 35° C.) throughout at least a portion of an incubation run. Further, for example, in various embodiments, the fluid composition sensor 100 may be configured to maintain an incubation humidity within the incubation chamber 190 (e.g., the incubation environment) of at least substantially between 10% and 99% (e.g., between 50% and 95%) throughout at least a portion of an incubation run. Further, for example, in various embodiments, the fluid composition sensor 100 may be configured to maintain an incubation light wavelength within the incubation chamber 190 (e.g., the incubation environment) sufficient so as to facilitate biological development of one or more particles disposed therein throughout at least a portion of an incubation run. In various embodiments, the incubation environment may be configured such that the incubation light wavelength within the incubation chamber 190 may vary over time. Further, for example, in various embodiments, the fluid composition sensor 100 may be configured to maintain an incubation illumination frequency within the incubation chamber 190 (e.g., the incubation environment) sufficient so as to facilitate biological development of one or more particles disposed therein throughout at least a portion of an incubation run. In various embodiments, the incubation environment may be configured such that the incubation illumination frequency within the incubation chamber 190 may vary over time. Further, for example, in various embodiments, the fluid composition sensor 100 may be configured to execute an incubation run for a runtime of at least substantially between 1 hour and 500 hours (e.g., between 10 hours and 100 hours).

In various embodiments, as described herein, an exemplary fluid composition sensor 100 may be configured to receive one or more of the plurality of particles within the fluid sample at a collection media disposed therein. Further, in various embodiments, a fluid composition sensor may be configured to capture particle data associated with the one or more of the plurality of particles within the fluid sample. For example, as described herein, the fluid composition sensor may be configured for generating, identifying, calculating, and/or capturing particle data related to the particle composition of one or more particles of the plurality within the fluid sample. In various embodiments, first particle data captured by an exemplary fluid composition sensor may comprise a particle image captured using one or more particle imaging techniques, such as, for example, lensless holography, fluorescent imaging, and/or the like. Further, in various embodiments, a fluid composition sensor may capture further particle data using one or more image focusing techniques, such as a computational technique (e.g., Angular Spectrum Propagation) and/or a mechanical technique (e.g., opto-mechanical adjustment). In various embodiments, the captured particle data may further comprise particle data generated based at least in part on the captured particle image, such as, for example, particle type data, particle matter mass concentration data, particle quantity data, particle size data, and/or the like, associated with one or more of the plurality of particles within the fluid sample. In various embodiments, the particle data may comprise first timestamp data corresponding to a first instance (e.g., a first time) at which the particle data was captured. In various embodiments, an exemplary fluid composition sensor 100 may be configured to generate first particle data associated with an initial particle configuration defined by the plurality of particles captured in a particle image at a first instance. In various embodiments, the fluid composition sensor 100 may be configured to receive from an external sensor and/or generate by an imaging device 110 second particle data associated with an incubated particle configuration defined by the plurality of particles at a second instance, wherein the second instance is subsequent an incubation operation wherein at least a portion of the plurality of particles are exposed to an incubation environment.

In various embodiments, upon capturing first particle data, an exemplary fluid composition sensor may be configured to reconfigure the used collection media assembly so as to facilitate the execution of an incubation operation. For example, as illustrated in FIGS. 11 and 12, an exemplary fluid composition sensor 100 may be configured to transport the used collection media assembly in a first direction to an incubation chamber 190. Alternatively, or additionally, the exemplary fluid composition sensor 100 may be configured to transport the used collection media assembly to a remote external environment for use in an incubation operation. In various environments, as illustrated, an exemplary sensor 100 may comprise a cover application component 191 arranged within an internal sensor portion at least substantially adjacent a sample travel path such that the cover application component 191 may interact with one or more used collection media assemblies 150 upon the collection media assembly 150 being dispensed from a particle engagement chamber 180. In various embodiments, a cover application component 191 may be configured to apply a cover layer to the used collection media assembly 150 so as to at least substantially seal and/or protect the collection media 106 and the particles disposed therein from an ambient environment. For example, a cover layer applied to a used collection media 106 may be configured to cover a receiving face of the collection media 106 so as to prevent one or more contaminants from interacting with the collection media 106. In various embodiments, a cover layer may be configured to prevent the used collection media 106 and/or the particles disposed therein from being compromised, such as, for example, via dehydration, cross-contamination from other fluid samples, and/or collection media, and/or the like.

As described herein, fluid composition sensor 100 may execute an incubation run wherein the used collection media assembly 106 associated with the captured first particle data is exposed to an exemplary incubation environment in order to culture the particles disposed within the collection media 106 and facilitate the physical and/or biological growth of one or more of the particles therein, as described herein. In various embodiments, upon executing an incubation run to incubate the collection media of the used collection media assembly 150 associated with the captured first particle data, fluid composition sensor 100 may be configured to capture second particle data associated with an incubated particle configuration defined by the plurality of particles within the collection media assembly 150 at a second instance subsequent the incubation operation in which at least a portion of the plurality of particles were exposed to the incubation environment. For example, in various embodiments, fluid composition sensor 100 may be configured to transport the used collection media assembly 150 from within an incubation chamber 190 in a second direction that is at least substantially opposite the first direction, so as to transport the collection media assembly 150 back to the particle engagement chamber 180. For example, as illustrated, an exemplary fluid composition sensor 100 may comprise an actuator element 166 configured to selectively apply a force to the used collection media assembly 150 disposed within the incubation chamber 190 so as to reposition the used collection media assembly 150 comprising one or more incubated particles from the incubation chamber 190 to the particle engagement chamber 180. For example, the actuator element 166 may be configured to move from a compressed position, as illustrated in FIG. 11, to an extended position. As the actuator element 166 moves from the compressed position to the extended position, the actuator element 166 may be configured to apply a force to the used collection media assembly 150. In such an exemplary circumstance, the same imaging device 110 utilized by the sensor 100 to capture the first particle data may be configured to capture the second particle data associated with an incubated particle configuration (e.g., a cultured plurality of particles). Alternatively, or additionally, in various embodiments, fluid composition sensor 100 may be configured to transport the used collection media assembly from within an incubation chamber 190 to a second imaging device that is at least substantially different than the imaging device 110 configured to capture the first particle data, as described herein. In various embodiments, the second particle data may comprise second timestamp data corresponding to a second instance (e.g., a second time) at which the second particle data was captured.

In various embodiments, an imaging device 110 may be configured to generate first particle data comprising a first particle image captured at a first time and second particle data comprising a second particle image captured a second time. For example, the first time may correspond to a time approximately immediately following a particle collection operation, wherein a plurality of particles defining an initial particle configuration is disposed within a collection media 106. In such an exemplary circumstance, the second time may be subsequent the first time and further subsequent the execution of a particle incubation operation (e.g., an incubation run), wherein the plurality of particles disposed within the collection media 106 was subjected to an incubation environment throughout an incubation run, such that the plurality of particles define an incubated particle configuration at the second time. In such a configuration, an exemplary device (e.g., a controller 200) may be configured to distinguish between the initial particle configuration and the incubated particle configuration, such as, for example, by identifying at least one particle characteristic associated with one or more of the plurality of particles that is at least substantially different at the second time compared to that at the first time.

FIG. 12 illustrates a cross-sectional view of an exemplary fluid composition sensor in an open configuration, wherein the exemplary fluid composition sensor comprises a plurality of collection media assemblies 150 disposed upon an alignment tape. As illustrated in FIG. 12, the plurality of collection media assemblies 150 disposed upon the alignment tape 156 may be arranged so as to define a row of collection media assemblies 150 extending along the length of the alignment tape. In various embodiments, the alignment tape may be moveable in either a first direction or an opposite second direction, each being at least substantially parallel with a linear axis extending along the length of the alignment tape such that the plurality of collection media assemblies 150 (e.g., comprising a plurality of collection media 106) disposed thereon may move relative to an internal sensor portion (e.g., a collection fluid dispense chamber 170, a particle collection chamber 180, an incubation chamber 190, and/or the like) of a fluid composition sensor 100. In various embodiments, at least a portion of the alignment tape 156 may be wound about both the first alignment tape spool 165A and the second alignment tape spool 165B, which may be collectively arranged such that at least a portion of the alignment tape 156 may extend therebetween. The first alignment tape spool 165A and the second alignment tape spool 165B may be further configured such that the at least a portion of the alignment tape 156 extending therebetween may have at least one collection media assembly 150 disposed thereon. For example, the fluid composition sensor may be configured such that the collection media assembly 150 disposed upon the at least a portion of the alignment tape 156 extending between the first alignment tape spool 165A and the second alignment tape spool 165B may be disposed at one or more positions within a fluid composition sensor 100, such as, for example, a collection fluid receiving position, a particle collection position, a particle incubation position, and/or the like.

In various embodiments, wherein the fluid composition sensor is in an open configuration, as illustrated, the alignment tape 156 may be configured such that the plurality of collection media assemblies 150 disposed on the alignment tape 156 may be moved (e.g., linearly shifted) in a first direction relative to the fluid composition sensor housing such that a fresh (e.g., unused) absorbent media 106b of the plurality of collection media assemblies 150 may be positioned within a collection fluid dispense chamber 170 (e.g., at a collection fluid receiving position), as described herein. Further, in various embodiments, the alignment tape 156 may be further configured such that a collection media assembly 150 disposed on the alignment tape 156 and positioned within the collection fluid dispense chamber 170 may be further moved (e.g., linearly shifted) in the first direction relative to the fluid composition sensor housing such that a fresh (e.g., unused) collection media 106 of the collection media assembly 150 may be positioned within a particle engagement chamber 180 (e.g., at a particle collection position), as described herein. Further, as illustrated, at least a portion of the alignment tape 156, such as, for example, a second alignment tape spool 165B may be disposed at least partially within an incubation chamber 190. In such an exemplary circumstance, the alignment tape 156 may be further configured such that a collection media assembly 150 disposed on the alignment tape 156 and positioned within the collection fluid dispense chamber 180 may be further moved (e.g., linearly shifted) in the first direction relative to the fluid composition sensor housing such that a used collection media 106 of the collection media assembly 150 comprising a plurality of particles received from a fluid sample may be positioned within an incubation chamber 190 (e.g., at a particle incubation position), as described herein. In various embodiments, for example, an exemplary fluid composition sensor 100 may be configured such that, upon execution of an incubation operation wherein the plurality of particles disposed within the used collection media 106 of the collection media assembly 150 was exposed to an incubation environment within the incubation chamber 190, the alignment tape 156 may be further configured such that an incubated collection media assembly 150 (e.g., comprising an collection media 106 including one or more incubated particles disposed therein) disposed on the alignment tape 156 and positioned within the incubation chamber 190 may be further moved (e.g., linearly shifted) in a second direction at least substantially opposite the first direction relative to the fluid composition sensor housing such that the incubated collection media assembly 150 may be positioned within a particle engagement chamber 180 (e.g., at a particle collection position), as described herein. In such an exemplary circumstance, as described herein, the fluid composition sensor may be configured to generate second particle data based at least in part on the one or more incubated particles disposed within the collection media 106 of the incubated collection media assembly 150.

In various embodiments, as described herein, fluid composition sensor 100 (e.g., a controller 200) may be configured to determine a biological particle characteristic associated with a fluid sample based at least in part on a comparison of the first particle data and second particle data. In various embodiments, for example, the biological particle characteristic may be based at least in part on a relative particle characteristic. In various embodiments, as described herein, a relative particle characteristic may be based at least in part on a comparison of the first particle data and the second particle data. For example, in various embodiments, the one or more relative particle characteristic may be defined at least in part by the incubated particle configuration exhibited by the one or more incubated particles. In various embodiments, a relative particle characteristic may comprise one or more comparative data, images, particle characteristics, and/or the like that defines a first particle characteristic associated with an initial particle configuration defined by a plurality of particles at the first instance relative to a corresponding second particle characteristic associated with an incubated particle configuration defined by the plurality of particles at the second instance. For example, a relative particle characteristic may comprise a comparison of one or more particles of the plurality at the first instance to the same one or more particles of the plurality at the second instance, such that a relative particle characteristic may define one or more relationships, differences, similarities, evolutions, and/or the like between the plurality of particles at a first instance (e.g., pre-incubation) and at a second instance (e.g., post-incubation).

In various embodiments, second particle data associated with an incubated particle configuration at a second instance (e.g., post-incubation) may define at least one particle characteristic associated with a particle that is at least substantially different from a corresponding particle characteristic of the same particle as defined by an initial particle configuration at a first instance (e.g., pre-incubation). For example, a detected discrepancy in a first particle characteristic and a second particle characteristic exhibited by a particle at a first instance and second instance, respectively, may be based at least in part on a biological growth and/or evolution of the particle caused by, as non-limiting example, an executed incubation operation and/or a collection media 106 comprising a biologically nutritive substance. For example, in various embodiments, an at least partial biological development (e.g., growth) may affect a change in one or more of a particle matter mass concentration, particle quantity, particle size, and/or the like, associated with one or more of the particles between a first instance and a second instance.

In particular, in various embodiments, an at least partial biological growth of a particle, as described herein, may result in an increase in the particle matter mass concentration and/or particle quantity associated with incubated particle configuration. As a non-limiting example, in various embodiments, as the particle is cultured between the first instance and the second instance, the particle size of the one or more particle (e.g., particle cross-sectional area, particle diameter, particle size category) may increase. Further, in such an exemplary circumstance, the particle size of the one or more particle may increase to a particle size that is above a detectable threshold (e.g., a sensor resolution), such that, at a second instance, one or more previously undetectable particles may be detectable to an exemplary fluid composition sensor. In such an exemplary circumstance, the second particle data associated with the incubated particle configuration may be defined at least in part by an increased particle concentration (e.g., particle matter mass concentration and/or particle quantity), such that a relative particle characteristic may comprise a relative particle concentration defined by a comparison (e.g., a difference) between a first particle concentration associated with the initial particle configuration defined at the first instance and the incubated particle configuration defined at the second instance.

In various embodiments, a biological particle characteristic may be based at least in part on relative particle characteristic defined by a ratio of a second particle characteristic value to a first particle characteristic value, wherein the second particle characteristic value is defined by the second particle data associated with the incubated particle configuration, and wherein the first particle characteristic value is defined by the first particle data associated with the initial particle configuration. Alternatively, or additionally, in various embodiments, a biological particle characteristic may be based at least in part on relative particle characteristic defined by a difference between a second particle characteristic value and a first particle characteristic value, wherein the second particle characteristic value is defined by the second particle data associated with the incubated particle configuration, and wherein the first particle characteristic value is defined by the first particle data associated with the initial particle configuration.

As shown in FIG. 13, an exemplary device 10 (e.g., a fluid composition sensor 100) may comprise a controller 200 configured to control the various operations associated with the particle collection function of a fluid composition sensor 100, as well as the imaging and analysis of the particles collected by the sensor to determine at least one particle characteristic of a volume of fluid received by sensor 100. As illustrated in FIG. 13, the controller 200 may comprise a memory 201, a processor 202, input/output circuitry 203, communication circuitry 205, an imaging device data repository 107, a collection media characteristic database 204, particle imaging circuitry 206, particle type identification circuitry 207, particle collection circuitry 208, collection media generation circuitry 209, and particle incubation circuitry 210. The controller 200 may be configured to execute the operations described herein. Although the components are described with respect to functional limitations, it should be understood that the particular implementations necessarily include the use of particular hardware. It should also be understood that certain of the components described herein may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the controller 200 should therefore be understood to include particular hardware configured to perform the functions associated with the particular circuitry as described herein.

The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the controller 200 may provide or supplement the functionality of particular circuitry. For example, the processor 202 may provide processing functionality, the memory 201 may provide storage functionality, the communications circuitry 205 may provide network interface functionality, and the like.

In some embodiments, the processor 202 (and/or coprocessor or any other processing circuitry assisting or otherwise associated with the processor) may be in communication with the memory 201 via a bus for passing information among components of the apparatus. The memory 201 may be non-transitory and may include, for example, one or more volatile and/or non-volatile memories. For example, the memory 201 may be an electronic storage device (e.g., a computer readable storage medium). In various embodiments, the memory 201 may be configured to store information, data, content, applications, instructions, or the like, for enabling the apparatus to carry out various functions in accordance with example embodiments of the present disclosure. It will be understood that the memory 201 may be configured to store partially or wholly any electronic information, data, data structures, embodiments, examples, figures, processes, operations, techniques, algorithms, instructions, systems, apparatuses, methods, look-up tables, or computer program products described herein, or any combination thereof. As a non-limiting example, the memory 201 may be configured to store particle size data, particle type data, particle impaction depth data, particle image data, particle shape data, particle cross-sectional area data, particle mass data, particle density data, and particulate matter mass concentration data associated with a volume of fluid. In various embodiments, the memory may be further configured to store one or more particle impaction depth-momentum look-up tables.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 202 may be configured to execute instructions stored in the memory 201 or otherwise accessible to the processor. Alternatively, or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present disclosure while configured accordingly. Alternatively, as another example, when the processor is embodied as an executor of software instructions, the instructions may specifically configure the processor to perform the algorithms and/or operations described herein when the instructions are executed.

In some embodiments, the controller 200 may include input-output circuitry 203 that may, in turn, be in communication with the processor 202 to provide output to the user and, in some embodiments, to receive input such as a command provided by the user. The input-output circuitry 203 may comprise a user interface, such as a graphical user interface (GUI), and may include a display that may include a web user interface, a GUI application, a mobile application, a client device, or any other suitable hardware or software. In some embodiments, the input-output circuitry 203 may also include a display device, a display screen, user input elements, such as a touch screen, touch areas, soft keys, a keyboard, a mouse, a microphone, a speaker (e.g., a buzzer), a light emitting device (e.g., a red light emitting diode (LED), a green LED, a blue LED, a white LED, an infrared (IR) LED, an ultraviolet (UV) LED, or a combination thereof), or other input-output mechanisms. The processor 202, input-output circuitry 203 (which may utilize the processing circuitry), or both may be configured to control one or more functions of one or more user interface elements through computer-executable program code instructions (e.g., software, firmware) stored in a non-transitory computer-readable storage medium (e.g., memory 201). Input-output circuitry 203 is optional and, in some embodiments, the controller 200 may not include input-output circuitry. For example, where the controller 200 does not interact directly with the user, the controller 200 may generate user interface data for display by one or more other devices with which one or more users directly interact and transmit the generated user interface data to one or more of those devices. For example, the controller 200, using user interface circuitry may generate user interface data for display by one or more display devices and transmit the generated user interface data to those display devices.

The communications circuitry 205 may be a device or circuitry embodied in either hardware or a combination of hardware and software that is configured to receive and/or transmit data from/to a network and/or any other device, circuitry, or module in communication with the controller 200. For example, the communications circuitry 205 may be configured to communicate with one or more computing devices via wired (e.g., USB, ethernet) or wireless (e.g., Bluetooth, Wi-Fi, cellular, and/or the like) communication protocols.

In various embodiments, the processor 202 may be configured to communicate with the particle imaging circuitry 206. The particle imaging circuitry 206 may be a device or circuitry embodied in either hardware or a combination of hardware and software that is configured to receive, process, generate, and/or transmit data, such as particle data generated by the fluid composition sensor (e.g., a particle image captured by the imaging device 110). In various embodiments, the particle imaging circuitry 206 may be configured to analyze one or more images captured by the imaging device 110 of the fluid composition sensor 100 to identify one or more distinctions between various images of the particles within a collection media 106 as captured by the imaging device 110 at various times. As a non-limiting example, the particle imaging circuitry 206 may be configured to analyze first particle data comprising a first particle image captured by an imaging device 110 of the fluid composition sensor 100 and second particle data comprising a second particle image captured by the imaging device 110 to identify one or more distinctions between the first and second particle images. The particle imaging circuitry 206 may receive from the imaging device a first captured particle image and a second captured particle image, captured at a first time and a second time, respectively, wherein the second is subsequent the first time, and wherein the second time is subsequent the execution of an incubation operation in which at least a portion of the plurality of particles captured by the collection media 106 were exposed to an incubation environment. In various embodiments, the particle imaging circuitry 206 may be further configured to analyze one or more images captured by the imaging device 110 of the fluid composition sensor 10 to determine the size of each of the one or more particles of the plurality of particles within the collection media 106 at various instances both before and after an incubation operation, as described herein. In various embodiments, the size of a particle may be defined by the cross-sectional area of the particle. In various embodiments, the particle imaging circuitry 206 may be configured to determine the particle size of particles with any of a variety of particle sizes. As an example, the particle imaging circuitry 206 may be configured to determine particle sizes of particles having a diameter of between about 0.3 and about 100 microns (e.g., 2.5 microns), and thus, a size category with which the particle may be associated, such as, for example, PM10, PM4, PM2.5, or PM1. In various embodiments, the controller and/or the particle imaging circuitry 206 may be further configured to analyze one or more images captured by the imaging device 110 of the fluid composition sensor 10 to determine the shape of each of the one or more particles of the plurality of particles within the collection media 106 at various instances both before and after an incubation operation, as described herein. In various embodiments, a particle shape may be defined at least in part by a particle cross-sectional area. The particle imaging circuitry 206 may be further configured to determine the particle impaction depth of each of the one or more particles of the plurality of particles within the collection media 106 at various instances both before and after an incubation operation, as described herein, using one or more image focusing techniques.

In various embodiments, the processor 202 may be configured to communicate with the particle type identification circuitry 207. The particle type identification circuitry 207 may be a device or circuitry embodied in either hardware or a combination of hardware and software that is configured to identify a particle type and/or particle species of one or more particles of the plurality of particles received by the collection media 106. In various embodiments, a plurality of particles within a volume of fluid may comprise one or more particles of various particle types, such as, for example, one or more of bacteria, pollen, spores, molds, biological particles, soot, CFUs, inorganic particles, and organic particles. In various embodiments, the particle type identification circuitry 207 may determine the particle type and/or particle species of each of the one or more particles of the plurality of particles received by the collection media 106 using one or more machine learning techniques. In various embodiments, the one or more machine learning techniques used by the particle type identification circuitry 207 to determine the particle type and/or species of each of the one or more particles of the plurality of particles may comprise analyzing an image captured by the imaging device 110, particle size data, particle shape data, and/or any other data generated, transmitted, and/or received by the controller 200. In various embodiments, the particle type identification circuitry 207 may send and/or receive data from the imaging device data repository 107.

In various embodiments, the particle type identification circuitry 207 may be configured to compare a second particle characteristic value defined by the second particle data associated with the incubated particle configuration to a first particle characteristic value defined by the first particle data associated with the initial particle configuration first particle characteristic value in order to identify a relative particle characteristic associated with both the initial particle configuration and the incubated particle configuration, as described herein. In various embodiments, the particle type identification circuitry 207 may be configured to determine a biological particle characteristic associated with a fluid sample based at least in part on the relative particle characteristic associated with both the initial particle configuration and the incubated particle configuration. For example, in various embodiments, the biological particle characteristic may be defined at least in part by a detected particle type characteristic associated one or more particles of a plurality within the fluid sample received by the fluid composition sensor 100, wherein the detected particle type characteristic may correspond to a determination that one or more of the plurality of particles comprises a colony-forming unit (CFU). For example, a determination that one or more of the plurality of particles comprises a colony-forming unit (CFU) may be based at least in part on a detected distinction between the particle size characteristic, particle quantity characteristic, particle mass matter concentration characteristic, and/or the like, exhibited by a particle in a first instance (pre-incubation) and a second instance (post-incubation). Further, in various embodiments, the particle type identification circuitry 207 may be configured to execute a feedback loop, wherein one or more velocity comparison data associated with one or more particles of the plurality of particles received by the collection media 106 may define one or more inputs into a machine learning model in order to increase a rate of machine learning associated with the one or more machine learning techniques, as described herein.

The particle collection circuitry 208 may be a device or circuitry embodied in either hardware or a combination of hardware and software that is configured to control the particle collection functionality of the fluid composition sensor 10, as described herein. For example, the particle collection circuitry 208 may control a fan disposed within the fluid control sensor 100 in order to execute a fluid sample collection process by pulling one or more volumes of fluid (e.g., sequentially) from an ambient environment into and through the fluid composition sensor 100. In various embodiments, the particle collection circuitry 208 may configure the fluid composition sensor between an open configuration and a closed configuration, as described herein. In various embodiments, the particle collection circuitry 208 may be configured to lock the fluid composition sensor 100 in a closed configuration during the fluid sample collection process. Further, the particle collection circuitry 208 may be configured to determine when the collection of the fluid sample is complete (e.g., after a predetermined amount of time, after a number of particles present within the collection media has surpassed a predetermined threshold number of particles, and/or after a percentage of particle coverage within a field of view has surpassed threshold particle coverage percentage). Upon such a determination, the particle collection circuitry 208 may be configured to selectively unlock the fluid composition sensor 100 and configure the sensor 100 in an open configuration. Further, in various embodiments, the particle collection circuitry 208 may facilitate the automated reconfiguration and/or replacement of one or more collection media assemblies, as described herein. For example, in various embodiments, the particle collection circuitry 208 may be configured to facilitate automated reconfiguration of a collection media assembly between one or more positions within an exemplary sensor 100, such as, for example, between a collection fluid receiving position, a particle collection position, and a particle incubation position (e.g., within an incubation chamber), and/or the like. In various embodiments, the particle collection circuitry 208 may communicate with the particle imaging circuitry 206 in order to facilitate the capturing of an image of an identification element disposed upon a replaceable collection media assembly and subsequent identification thereof. In various embodiments, the image of the identification element disposed upon the replaceable collection media assembly may be communicated to one or more components (e.g., internal sensor components and/or external system databases) to facilitate the identification of the particular replaceable collection media assembly captured in the image.

In various embodiments, the fluid composition sensor 10 may be configured with, or in communication with, an imaging device data repository 107. The imaging device data repository 107 may be stored, at least partially on the memory 201 of the system. In some embodiments, the imaging device data repository 107 may be remote from, but in connection with, the fluid composition sensor 100. The imaging device data repository 107 may contain information, such as images relating to one or more potential components of fluids. In some embodiments, the imaging device data repository 107, and/or other similar reference databases in communication with the fluid composition sensor 100, may comprise non-image information used to identify particles (e.g., for florescent particles, a spectrometer may be used by the fluid composition sensor 100 as discussed herein and the fluid composition sensor 100 may receive spectrum information to identify and/or classify the particles). In some embodiments, the fluid composition sensor 100 may also use machine learning for identifying and/or classifying particles, such that the fluid composition sensor 100 may use a reference database, such as the imaging device data repository 107, to initially train the fluid composition sensor 10 and then may be configured to identify and/or classify particles, such as, for example, CFUs, without referencing the imaging device data repository 107 or other reference databases (e.g., a system may not be in active communication with the imaging device data repository 107 during regular operations).

In various embodiments, the processor 202 may be configured to communicate with the collection media generation circuitry 209. The collection media generation circuitry 209 may be a device or circuitry embodied in either hardware or a combination of hardware and software that is configured to receive, process, generate, and transmit data related to the fluid composition sensor's execution of a collection fluid dispense operation and interaction with other components of the sensor 100 via, for example, collection fluid dispense operation commencement and completion signals. In various embodiments, the collection media generation circuitry 209 may be configured to receive a collection fluid dispense operation commencement command based on signals transmitted from, for example, the particle collection circuitry 208. Further, the collection media generation circuitry 209 may be configured to communicate with the memory 204 and process commands related to an absorbent media (e.g., an absorbent media 106b) configuration (e.g., surface area, thickness, material, and/or the like). In various embodiments, the collection media generation circuitry 209 may be configured to transmit a collection fluid dispense operation completion signal to one or more circuitry components of the controller 200.

In various embodiments, the processor 202 may be configured to communicate with the particle incubation circuitry 210. The particle incubation circuitry 210 may be a device or circuitry embodied in either hardware or a combination of hardware and software that is configured to receive, process, generate, and transmit data related to the fluid composition sensor's execution of an incubation operation and interaction with other components of the sensor 100 via, for example, incubation operation commencement and completion signals. In various embodiments, the particle incubation circuitry 210 may be configured to receive an incubation operation commencement command based on signals transmitted from, for example, the particle collection circuitry 208. Further, the particle incubation circuitry 210 may be configured to communicate with the memory 204 and process commands related to an incubation environment configuration (e.g., temperature, humidity, runtime, and/or the like). In various embodiments, the particle incubation circuitry 210 may be configured to transmit an incubation operation completion signal to one or more circuitry components of the controller 200.

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A device for detecting fluid particle characteristics comprising:
   a fluid composition sensor configured to receive a volume of fluid, the fluid composition sensor comprising:
   an absorbent media disposed at least partially within an internal sensor portion of the fluid composition sensor;
   a collection fluid dispense assembly configured to selectively dispense a volume of collection fluid onto the absorbent media so as to cause a collection media to be produced based at least in part on an interaction between the volume of collection fluid and the absorbent media; wherein the collection media is configured to receive one or more particles of a plurality of particles within the volume of fluid, and wherein the volume of collection fluid is based at least in part on one or more filter characteristics of the absorbent media; and
   an imaging device configured to capture a particle image of at least a portion of the one or more particles received by the collection media; and
   a controller configured to determine, based at least in part on the image, at least one particle characteristic of the plurality of particles of the volume of fluid.

2. The device of claim 1, wherein the collection fluid dispense assembly is configured to selectively dispense a plurality of volumes of collection fluid respectively onto a plurality of absorbent media, each of the plurality of absorbent media defining at least a portion of a respective collection media assembly; wherein the fluid composition sensor is configured to sequentially receive a plurality of collection media assemblies within the internal sensor portion at least substantially in series.

3. The device of claim 1, wherein the imaging device is configured to capture the particle image using lensless holography.

4. The device of claim 1, wherein the collection fluid dispense assembly is configured to selectively dispense the volume of collection fluid onto the absorbent media disposed at a first position within the internal sensor portion; and wherein the collection media is configured to receive the one or more particles from within the volume of fluid at a second position within the internal sensor portion.

5. The device of claim 4, wherein the fluid composition sensor further comprises a housing that defines the internal sensor portion and is selectively configurable between a first housing configuration and a second housing configuration; wherein the first housing configuration enables a reconfiguration of the collection media between the first position and the second position; and wherein the second housing configuration provides a secured seal so as to isolate the at least a portion of the collection media disposed within the internal sensor portion from a volume of ambient fluid.

6. The device of claim 4, wherein the absorbent media is attached to a substrate tape defined at least in part by a substrate tape length extending in a first direction, wherein the collection media produced based at least in part on the interaction between the dispensed volume of collection fluid and the absorbent media is disposed upon the substrate tape; and wherein the substrate tape is configured such that a reconfiguration of the collection media from the first position to the second position within the internal sensor portion is defined by a shift of the substrate tape along a linear travel path extending in the first direction so as to cause the collection media to move relative to the internal sensor portion.

7. The device of claim 1, wherein the volume of collection fluid comprises Triacetin.

8. The device of claim 1, wherein the collection fluid dispense assembly comprises a collection fluid cartridge configured to store one or more volumes of collection fluid therein, the collection fluid cartridge being fluidly connected to a dispense header configured to direct a flow of the volume of collection fluid dispensed from the collection fluid cartridge in a dispense direction.

9. The device of claim 1, wherein the controller is configured to generate one or more control signals configured to cause the device to reposition the collection media from a first position to a second position upon determining that the volume of collection fluid has been dispensed from the collection fluid dispense assembly.

10. A device for detecting fluid particle characteristics comprising:
a fluid composition sensor configured to receive a fluid sample comprising a plurality of particles, the fluid composition sensor comprising:
an internal sensor portion configured to receive a collection media assembly comprising a collection media, the collection media comprising: an absorbent media and a biologically nutritive substance dispersed on the absorbent media, wherein a volume of the biologically nutritive substance dispersed on the absorbent media is based at least in part on one or more filter characteristics of the absorbent media, and wherein the collection media is configured to receive at least a portion of the plurality of particles from within the fluid sample; and
an imaging device configured to generate first particle data using a particle imaging operation, the first particle data being associated with an initial particle configuration defined by the plurality of particles at a first instance;
a controller configured to determine a biological particle characteristic associated with the fluid sample based at least in part on a comparison of the first particle data and second particle data, the second particle data being associated with an incubated particle configuration defined by the plurality of particles at a second instance, wherein the second instance is subsequent an incubation operation wherein at least a portion of the plurality of particles are exposed to an incubation environment.

11. The device of claim 10, wherein the biological particle characteristic is defined at least in part by a detected particle type characteristic associated with one or more particles of the plurality of particles received by the fluid composition sensor, wherein the detected particle type characteristic corresponds to a determination that one or more of the plurality of particles comprises a colony-forming unit (CFU).

12. The device of claim 10, wherein the particle imaging operation comprises lensless holography.

13. The device of claim 10, wherein the biologically nutritive substance comprises one or more of an agar substance and a gelatin-based gel substance, the biologically nutritive substance being defined at least in part by one or more nutritional characteristics configured to facilitate biological development of one or more particles engaged therewith.

14. The device of claim 10, wherein the collection media comprises a nonnutritive substance layer disposed on top of a receiving face of the collection media.

15. The device of claim 10, wherein the fluid composition sensor is configured to receive a second fluid sample, and wherein the fluid composition sensor is further configured to at determine a second biological particle characteristic associated with the second fluid sample via one or more sequential operations executed at least substantially in series in an at least substantially automated configuration.

16. The device of claim 10, further comprising an incubation chamber comprises an internal chamber portion configured to define the incubation environment; wherein the incubation chamber is configured to receive the collection media assembly comprising the collection media within the internal chamber portion; and wherein the device is configured to execute the incubation operation by exposing the plurality of particles disposed within the collection media to the incubation environment within the incubation chamber such that one or more of the plurality of particles disposed within the collection media comprises one or more incubated particles defining the incubated particle configuration.

17. The device of claim 16, wherein the incubation chamber is in electronic communication with the controller, and wherein the controller is further configured to selectively control one or more incubation environment conditions defining the incubation environment such that the incubation operation may define an at least partially automated operation.

18. The device of claim 10, wherein the imaging device is further configured to generate the second particle data associated with the incubated particle configuration at the second instance.

19. The device of claim 10, wherein the fluid composition sensor comprises a second imaging device configured to generate the second particle data associated with the incubated particle configuration at the second instance.

20. The device of claim 10, wherein one or both of the controller and the imaging device is configured to read one or more identification elements disposed on the collection media assembly so as to identify the collection media assembly, wherein the one or more identification elements are configured to uniquely identify the collection media assembly.

* * * * *